US012565488B2

(12) United States Patent
Jacobson et al.

(10) Patent No.: US 12,565,488 B2
(45) Date of Patent: Mar. 3, 2026

(54) INHIBITORS OF INFLUENZA VIRUS REPLICATION

(71) Applicant: COCRYSTAL PHARMA, INC., Bothell, WA (US)

(72) Inventors: Irina C. Jacobson, Sammamish, WA (US); Sam Sk Lee, Edmonds, WA (US); Michael D. Feese, Seattle, WA (US)

(73) Assignee: COCRYSTAL PHARMA, INC., Bothell, WA (US)

( * ) Notice: Subject to any disclaimer, the term of this patent is extended or adjusted under 35 U.S.C. 154(b) by 997 days.

(21) Appl. No.: 17/297,312

(22) PCT Filed: Nov. 26, 2019

(86) PCT No.: PCT/US2019/063167

§ 371 (c)(1),
(2) Date: May 26, 2021

(87) PCT Pub. No.: WO2020/112716

PCT Pub. Date: Jun. 4, 2020

(65) Prior Publication Data

US 2022/0048897 A1 Feb. 17, 2022

Related U.S. Application Data

(60) Provisional application No. 62/771,283, filed on Nov. 26, 2018.

(51) Int. Cl.

| | |
|---|---|
| ***C07D 405/12*** | (2006.01) |
| ***A61P 31/16*** | (2006.01) |
| ***C07D 213/69*** | (2006.01) |
| ***C07D 213/89*** | (2006.01) |
| ***C07D 401/12*** | (2006.01) |
| ***C07D 405/06*** | (2006.01) |
| ***C07D 405/14*** | (2006.01) |
| ***C07D 409/12*** | (2006.01) |
| ***C07D 409/14*** | (2006.01) |

(52) U.S. Cl.

CPC ............ *C07D 405/12* (2013.01); *A61P 31/16* (2018.01); *C07D 213/69* (2013.01); *C07D 213/89* (2013.01); *C07D 401/12* (2013.01); *C07D 405/06* (2013.01); *C07D 405/14* (2013.01); *C07D 409/12* (2013.01); *C07D 409/14* (2013.01)

(58) Field of Classification Search

CPC .................................................... C07D 405/12

See application file for complete search history.

(56) References Cited

U.S. PATENT DOCUMENTS

| | | | |
|---|---|---|---|
| 2012/0022251 A1 | 1/2012 | Sumino et al. | |
| 2012/0022255 A1 | 1/2012 | Fujishita et al. | |
| 2013/0197219 A1 | 8/2013 | Takahashi et al. | |
| 2015/0031876 A1 | 1/2015 | Sumino et al. | |
| 2015/0111854 A1 | 4/2015 | Takahashi et al. | |
| 2016/0002211 A1 | 1/2016 | Sumino et al. | |
| 2017/0349587 A1 | 12/2017 | Takahashi et al. | |
| 2019/0248785 A1 | 8/2019 | Takahashi et al. | |

FOREIGN PATENT DOCUMENTS

| | | | |
|---|---|---|---|
| EP | 2412708 A1 * | 2/2012 | ........... A61K 9/0019 |
| EP | 2412709 A1 | 2/2012 | |
| EP | 2421708 A1 * | 2/2012 | ............. B32B 27/06 |
| EP | 2620436 A1 | 7/2013 | |

OTHER PUBLICATIONS

PCT International Search Report issued Mar. 2, 2020, in international application No. PCT/US2019/063167 (3 pages).

Freeman et al., "N-Aralkyl Derivatives of 4-Pyridone and Chelidamic Acid", J. Am. Cancer Society, vol. 69, pp. 858-859 (1947).

* cited by examiner

*Primary Examiner* — John S Kenyon
*Assistant Examiner* — Rehana Ismail
(74) *Attorney, Agent, or Firm* — Venable LLP

(57) ABSTRACT

Methods of inhibiting the replication of influenza viruses in a biological sample or patient, of reducing the amount of influenza viruses in a biological sample or patient, and of treating influenza in a patient, comprises administering to said biological sample or patient a safe and effective amount of a compound represented by Formula I, or a pharmaceutically acceptable salt thereof. A pharmaceutical composition comprises a safe and effective amount of such a compound or pharmaceutically acceptable salt thereof, and a pharmaceutically acceptable carrier, adjuvant or vehicle.

24 Claims, No Drawings

INHIBITORS OF INFLUENZA VIRUS REPLICATION

FIELD OF THE DISCLOSURE

This disclosure relates generally to inhibitors of influenza virus replication, and methods of treating or preventing an influenza infection by administering the inhibitors to a patient in need of treatment thereof.

BACKGROUND

Influenza spreads around the world in seasonal epidemics, resulting in the deaths of hundreds of thousands annually-millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (e.g. within about 6 feet) infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, Isavirus and Thogoto virus.

The Influenza virus A genus is responsible for seasonal flu and pandemic flu epidemics. It has one species, influenza A virus, and wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which has unusual zoonotic potential), H1N2 (endemic in humans and pigs), H9N2, H7N2, H7N3 and H10N7.

The Influenza virus B genus is responsible for season flu, and has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza viruses are very similar in structure. The influenza virus genome consists of eight single-stranded RNAs packed into rod-like structures of varying size, known as the ribonucleoprotein complex (RNP). Each RNP contains a unique viral RNA, multiple copies of the scaffolding nucleoprotein, and a heterotrimeric viral polymerase consisting of the PA, PB1, and PB2 subunits, which catalyzes the transcription and replication of the viral genome. Recent biochemical and structural studies of influenza polymerase complex provide insight into the mechanistic understanding of cap-snatching and RNA synthesis by influenza polymerase. Briefly, the PB2 cap-binding domain first sequesters the host pre-mRNAs by binding to their 5' cap. PA, the endonuclease subunit, then cleaves the captured pre-mRNA 10-13 nucleotides downstream of the cap. The PB2 subunit subsequently rotates about 700 to direct the capped primer into the PB1 polymerase active site. The PB1 subunit directly interacts with both PB2 and PA subunits. These subunits contain highly conserved domains among different influenza strains, and have attracted as an attractive anti-influenza drug target. In addition to the polymerase complex, the influenza genome encodes its own neuraminidase (NA), hemagglutinin (HA), nucleoprotein (NP), matrix proteins, M1 and M2, and non-structural proteins, NS1 and NS2. NA is the target for the antiviral drugs oseltamivir (Tamiflu) and zanamivir (Relenza). These drugs are sialic acid analogues which inhibit the enzymatic activity of NA, thus slowing down the release of progeny virus from infected cells.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Also, because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant-antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with NA inhibitors being particularly effective, but viruses can develop resistance to the approved NA antiviral drugs. Also, emergence of a multidrug-resistant pandemic influenza A viruses has been well documented. Drug-resistant pandemic influenza A becomes a substantial public health threat. In addition to the drug resistant influenza A viruses, the NA inhibitors are approved for the treatment early influenza infection (within 48 hours of influenza symptom onset).

Thus, there is still a need for drugs for treating influenza infections, such as for drugs with expanded treatment window, and/or reduced sensitivity to viral titer.

SUMMARY

The present disclosure generally relates to methods of treating influenza, to methods of inhibiting the replication of influenza viruses, to methods of reducing the amount of influenza viruses, to compounds and compositions that can be employed for such methods.

In one aspect, the disclosure provides compounds of Formula I and pharmaceutically acceptable salts thereof:

(I)

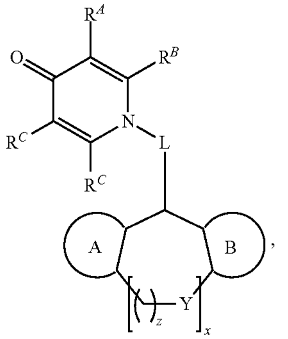

wherein:

Y is O, S, $SO_2$, or $NR^1$;

A and B are each independently null, $C_{6-10}$aryl, or 5-7 membered heteroaryl having 1-3 ring heteroatoms selected from N, O, and S, and the aryl or heteroaryl is optionally substituted with 1-4 $R^2$;

L is a bond, $NR^3$, or $C(R^4)_2$;

$R^A$ is H, OH, —O—$C_{6-10}$aryl, or —O—$C_{1-6}$alkylene-O—$CO_2R^4$;

$R^B$ is H, —OH, $CO_2R^4$, $C(O)NH_2$, C(O)NHOH, C(O)$NHOR^5$, $C(O)NHR^5$, or $CON(R)_2$;

each $R^C$ is independently H, OH, or $CO_2R^4$;

$R^1$ is H, $C_{1-6}$alkyl, $C_{1-6}$alkylene-$C_{6-10}$aryl, or —$CO_2R^4$, and $C_{6-10}$aryl is optionally substituted with $OR^4$;

each $R^2$ is independently H, halo, —OH, $C_{1-6}$ alkyl, $C_{1-6}$alkoxy, —$NH_2$, —NH($C_{1-6}$alkyl), —N($C_{1-6}$ alkyl)$_2$, —CN, —$CO_2R^4$, $C_{6-10}$aryl, or 5-10 membered heterocyclyl having 1-3 ring heteroatoms selected from N, O, and S, and each of $C_{1-6}$alkyl, $C_{1-6}$alkoxy, $C_{6-10}$aryl, and 5-10 membered heterocyclyl is optionally substituted with 1-3 halo;

$R^3$ is H, $C_{1-6}$alkyl, —C(O)$C_{1-6}$alkyl, or $C_{1-6}$alkylene-$C_{6-10}$aryl, each $R^4$ is independently H, $C_{1-6}$alkyl, or $C_{0-6}$alkylene-Ar;

each $R^5$ is independently H, —OH, —$C_{1-6}$ alkyl, $C_{1-6}$alkoxy, —$C_{1-6}$alkoxy-$C_{6-10}$aryl, or —$C_{0-6}$alkylene-$C_{6-10}$aryl, and —$C_{1-6}$ alkyl and $C_{6-10}$aryl are optionally substituted with $R^6$ or $OR^6$;

each $R^6$ is independently H, —$C_{1-6}$alkyl, —$C_{0-6}$alkylene-$C_{6-10}$aryl, —$C_{1-6}$alkylene-O—$C_{1-6}$alkyl, or

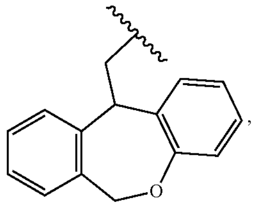 [SMILES: *CC1c2ccccc2COc2ccccc21]

and $C_{1-6}$alkyl and $C_{6-10}$aryl are optionally substituted with one or more $R^7$;

$R^7$ is H, —OH, —$CF_3$, or $C_{6-10}$aryl;

Ar is 5-10 membered heteroaryl comprising 1-3 ring heteroatoms selected from O, N, and S optionally substituted with (i) 1-3 $C_{3-8}$ cycloalkyl or (ii) 5-10 membered heteroaryl comprising 1-3 ring heteroatoms selected from O, N, and S, and each of $C_{3-8}$ cycloalkyl (i) and 5-10 membered heteroaryl (ii) is optionally substituted with 1-3 $R^2$;

x is 0 or 1; and z is 0 or 1, or a pharmaceutically acceptable salt thereof, with the proviso that when z is 0, then Y is $NR^1$, A is null, and L is $NR^3$.

In some cases, the compounds are compounds of any one of Formulas Ia-Ih:

(Ia)

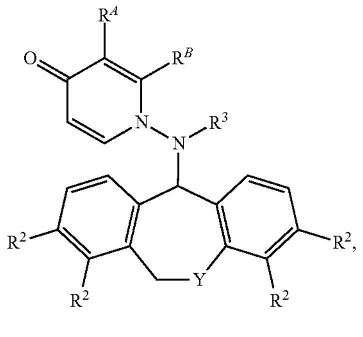

-continued (Ib)

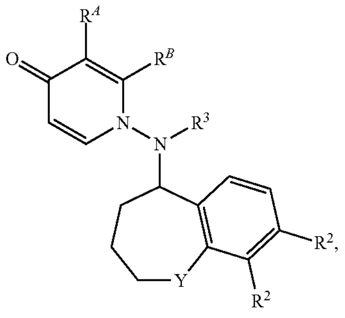

(Ic)

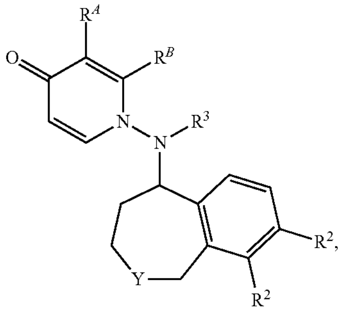

(Id)

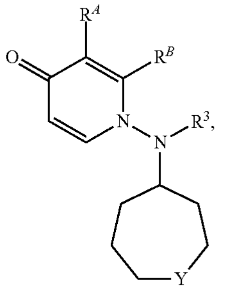

(Ir)

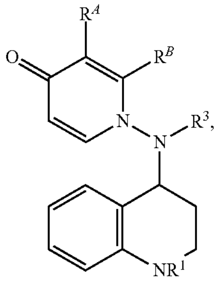

(If)

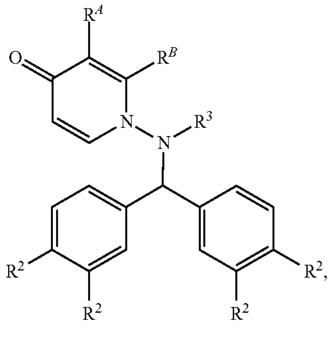

-continued (Ig)

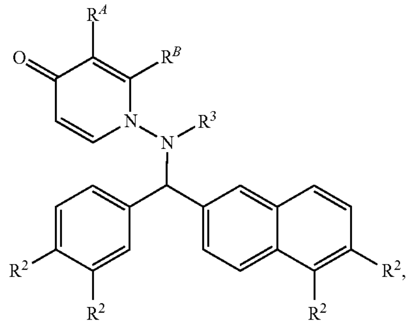

or (Ih)

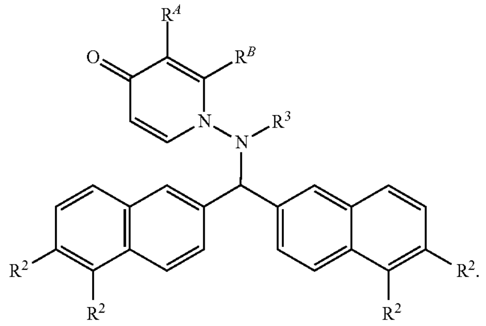

Further provided are methods of administering to a biological sample or patient a safe and effective amount of a compound as disclosed herein, e.g., as represented by Formulas I or Ia-Ih.

Also provided are methods inhibiting of endonuclease activity of influenza polymerase PA in an influenza A or B virus by contacting said virus with a safe and effective amount of a compound as disclosed herein, e.g., as represented by Formulas I or Ia-Ih. In some cases, inhibiting endonuclease activity of influenza polymerase PA in an influenza A or B virus includes administering to a patient a safe and effective amount of a compound as disclosed herein e.g., as represented by Formulas I or Ia-Ih.

Further provided are methods of reducing endonuclease activity of influenza polymerase PA in an influenza A or B virus in a host by administering a safe and effective amount of a compound as disclosed herein, e.g., as represented by Formulas I or Ia-Ih.

Also provided herein are methods of reducing the amount of influenza viruses in a biological sample or in a patient by administering to said biological sample or patient a safe and effective amount of a compound as disclosed herein, e.g., as represented by any of Formulas I or Ia-Ih.

Further provided are methods of treating or preventing an Influenza A or Influenza B infection in a patient, comprising administering to said patient a safe and effective amount of a compound as disclosed herein, e.g., as represented by Formulas I or Ia-Ih.

Also provided are pharmaceutical compositions comprising a compound as disclosed herein, e.g., as represented by any of Formulas I or Ia-Ih, or a pharmaceutically acceptable salt thereof, and a pharmaceutically acceptable excipient, carrier, adjuvant or vehicle.

Also provided are uses of a compound described herein for inhibiting or reducing the replication of influenza viruses in a biological sample or patient, for reducing the amount of influenza viruses in a biological sample or patient, or for treating influenza in a patient.

Further provided herein are uses of a compound described herein for the manufacture of a medicament for treating influenza in a patient, for reducing the amount of influenza viruses in a biological sample or in a patient, or for inhibiting the replication of influenza viruses in a biological sample or patient.

DETAILED DESCRIPTION

Provided herein are compounds, and their for use in treating or preventing an influenza infection. Also provided are uses of the compounds described herein, or pharmaceutically acceptable salts thereof, or pharmaceutically acceptable compositions comprising such a compound or a pharmaceutically acceptable salt thereof, for inhibiting the replication of influenza viruses in a biological sample or in a patient, for reducing the amount of influenza viruses (reducing viral titer) in a biological sample or in a patient, and for treating influenza in a patient.

The present disclosure will be better understood with reference to the following definitions.

Definitions and General Terminology

For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the disclosure may optionally be substituted with one or more substituents, such as illustrated generally below, or as exemplified by particular classes, subclasses, and species of the disclosure. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted. For example, if X is optionally substituted $C_1$-$C_6$alkyl or phenyl; X may be either optionally substituted $C_1$-$C_6$ alkyl or optionally substituted phenyl. Likewise, if the term "optionally substituted" follows a list, said term also refers to all of the substitutable groups in the prior list unless otherwise indicated. For example: if X is $C_1$-$C_6$alkyl or phenyl wherein X is optionally and independently substituted by $R^6$, then both $C_1$-$C_6$alkyl and phenyl may be optionally substituted by $R^6$. As is apparent to one having ordinary skill in the art, groups such as H, halogen, $NO_2$, CN, $NH_2$, OH, or $OCF_3$ would not be substitutable groups.

The phrase "up to", as used herein, refers to zero or any integer number that is equal or less than the number following the phrase. For example, "up to 3" means any one of 0, 1, 2, and 3. As described herein, a specified number range of atoms includes any integer therein. For example, a group having from 1-4 atoms could have 1, 2, 3, or 4 atoms.

Selection of substituents and combinations of substituents envisioned by this disclosure are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "alkyl" or "alkylene" as used herein means a saturated straight or branched chain hydrocarbon. Each of "alkyl" and "alkylene" as used herein can be optionally substituted as set forth below. In some embodiments, the "alkyl" is $C_1$-$C_6$ alkyl or $C_1$-$C_4$ alkyl. Specific examples include, but are not limited to, methyl, ethyl, isopropyl, n-propyl, sec-butyl, and t-butyl.

The term "cycloalkyl" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Cycloalkyl groups can include cycloalkenyl groups. Specific examples include, but are not limited to, cyclohexyl, cyclopentenyl, cyclopropyl, and cyclobutyl.

The term "heterocycle" as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, the heterocycle comprises up to three (e.g., 1 to 3, 1, 2, or 3) ring heteroatoms selected from N, S and O. Heterocycles include monocyclic, bicyclic or polycyclic fused, spiro or bridged heterocyclic ring systems, as well as polycyclic ring systems in which the heterocyclic ring can be fused to one or more cycloalkyl or heterocycle rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrothiophenyl, morpholino (including, for example, 3-morpholino, 4-morpholino), 2-thiomorpholino, 3-thiomorpholino, 4-thiomorpholino, 1-pyrrolidinyl, 2-pyrrolidinyl, 3-pyrrolidinyl, pyrrolidin-2-one, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" refers to aromatic ring groups have only carbon ring atoms (typically six to fourteen or six to ten) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term aryl, as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl" refers to a heterocycle that is aromatic, having five to fourteen members (e.g., 5 to 10 members), including monocyclic heteroaromatic rings and polycyclic aromatic rings in which a monocyclic aromatic ring is fused to one or more other aromatic ring. Heteroaryl groups have one or more ring heteroatoms selected from N, O, and S. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6.5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this disclosure, unless only one of the isomers is specifically indicated. Therefore, single stereochemical isomers as well as enantiomeric, diastereomeric, cis/trans, conformational, and rotational mixtures of the present compounds are within the scope of the disclosure.

Unless otherwise indicated, all tautomeric forms of the compounds of the disclosure are within the scope of the disclosure.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this disclosure. Such compounds are useful, for example, as analytical tools or probes in biological assays. Such compounds, especially deuterium analogs, can also be therapeutically useful.

The terms "a bond", "null", and "absent" are used interchangeably to indicate that a group is absent.

The compounds of the disclosure are defined herein by their chemical structures and/or chemical names. Where a compound is referred to by both a chemical structure and a chemical name, and the chemical structure and chemical name conflict, the chemical structure is determinative of the compound's identity.

I. Compounds

Provided herein are compounds of Formula I, or pharmaceutically acceptable salts thereof:

(I)

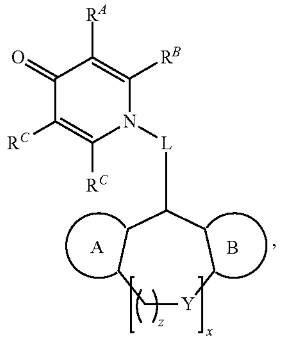

, wherein:

Y is O, S, $SO_2$, or $NR^1$;

A and B are each independently null, $C_{6-10}$aryl, or 5-7 membered heteroaryl having 1-3 ring heteroatoms selected from N, O, and S, and the aryl or heteroaryl is optionally substituted with 1-4 $R^2$;

L is a bond, $NR^3$, or $C(R^4)_2$;

$R^A$ is H, OH, —O—$C_{6-10}$aryl, or —O—$C_{1-6}$alkylene-O—$CO_2R^4$;

$R^B$ is H, —OH, $CO_2R^4$, $C(O)NH_2$, C(O)NHOH, C(O)NHOR$^5$, C(O)NHR$^5$, or CON$(R^5)_2$;

each $R^C$ is independently H, OH, or $CO_2R^4$;

$R^1$ is H, $C_{1-6}$alkyl, $C_{1-6}$-alkylene-$C_{6-10}$aryl, or —$CO_2R^4$, and $C_{6-10}$aryl is optionally substituted with $OR^4$;

each $R^2$ is independently H, halo, —OH, $C_{1-6}$ alkyl, $C_{1-6}$alkoxy, —$NH_2$, —NH($C_{1-6}$alkyl), —N($C_{1-6}$ alkyl)$_2$, —CN, —$CO_2R^4$, $C_{6-10}$aryl, or 5-10 membered heterocyclyl having 1-3 ring heteroatoms selected from N, O, and S, and each of $C_{1-6}$alkyl, $C_{1-6}$alkoxy, $C_{6-10}$aryl, and 5-10 membered heterocyclyl is optionally substituted with 1-3 halo;

$R^3$ is H, $C_{1-6}$alkyl, —C(O)$C_{1-6}$alkyl, or $C_{1-6}$alkylene-$C_{6-10}$aryl, each $R^4$ is independently H, $C_{1-6}$alkyl, or $C_{0-6}$alkylene-Ar;

each $R^5$ is independently H, —OH, —$C_{1-6}$ alkyl, $C_{1-6}$alkoxy, —$C_{1-6}$alkoxy-$C_{6-10}$aryl, or —$C_{0-6}$alkylene-$C_{6-10}$aryl, and —$C_{1-6}$ alkyl and $C_{6-10}$aryl are optionally substituted with $R^6$ or $OR^6$;

each $R^6$ is independently H, —$C_{1-6}$alkyl, —$C_{0-6}$alkylene-$C_{6-10}$aryl, —$C_{1-6}$alkylene-O—$C_{1-6}$alkyl, or

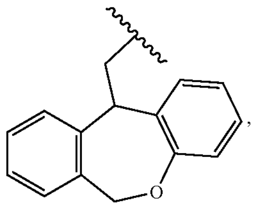 [SMILES: *CC1c2ccccc2COc2ccccc21]

and $C_{1-6}$alkyl and $C_{6-10}$aryl are optionally substituted with one or more $R^7$;

$R^7$ is H, —OH, —$CF_3$, or $C_{6-10}$aryl;

Ar is 5-10 membered heteroaryl comprising 1-3 ring heteroatoms selected from O, N, and S optionally substituted with (i) 1-3 $C_{3-8}$ cycloalkyl or (ii) 5-10 membered heteroaryl comprising 1-3 ring heteroatoms selected from O, N, and S, and each of $C_{3-8}$ cycloalkyl (i) and 5-10 membered heteroaryl (ii) is optionally substituted with 1-3 $R^2$;

x is 0 or 1; and z is 0 or 1, or a pharmaceutically acceptable salt thereof, with the proviso that when z is 0, then Y is $NR^1$, A is null, and L is $NR^3$.

In various cases, the compound disclosed herein has a structure of any one of Formulas Ia-Ih:

(Ia)

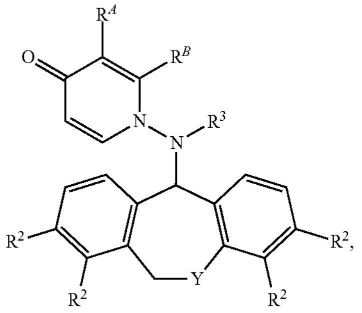

(Ib)

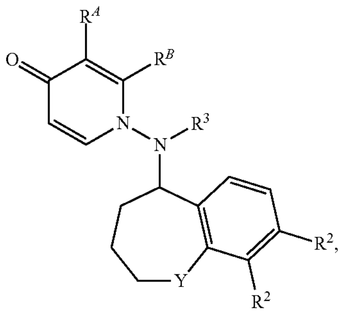

-continued (Ic)

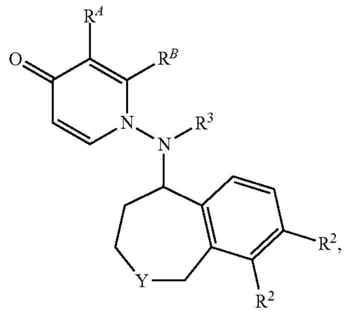

(Id)

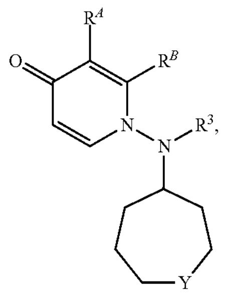

(Ir)

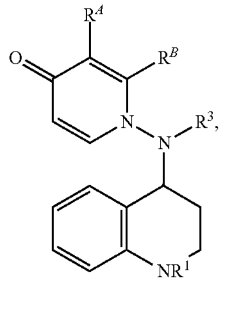

(If)

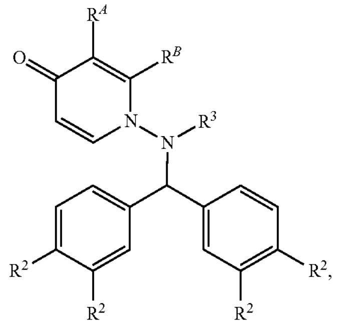

(Ig)

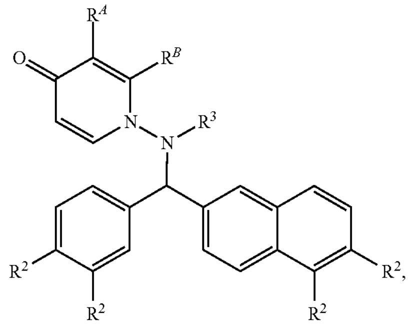

or

-continued (Ih)

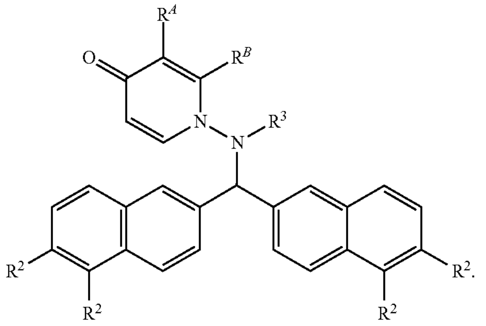

In some cases, x is 0. In some cases, x is 1.

In some cases, z is 0. In some cases, z is 1.

In some cases, at least one of A or B is $C_6$aryl. In some cases, one of A and B is $C_6$aryl. In some cases, both of A and B are $C_6$aryl. In some cases, at least one of A or B is $C_{10}$aryl. In some cases, one of A and B is $C_{10}$aryl. In some cases, both of A and B are $C_{10}$aryl. In some cases, one of A and B is naphthyl. In some cases, both of A and B are naphthyl. In some cases, at least one of A and B is 5-7 membered heteroaryl. In some cases, one of A and B is 5-7 membered heteroaryl.

In some cases, Y is O. In some cases, Y is S. In some cases, Y is $SO_2$. In some cases, Y is $NR^1$. In some cases, Y is NH. In some cases, Y is N-phenyl. In some cases, Y is N-benzyl. In some cases, Y is N-methyl. In some cases, Y is N-tert-butyoxycarbonyl.

In some cases, L is a bond. In some cases, L is $NR^3$. In some cases, L is NH. In some cases, L is N—$CH_3$. In some cases, L is N-benzyl. In some cases, L is $CH_2$.

In some cases, $R^A$ is H. In some cases, $R^A$ is OH. In some cases, $R^A$ is —O—$C_{6-10}$aryl. In some cases, $R^A$ is —O-phenyl.

In some cases, $R^B$ is H. In some cases, $R^B$ is —OH. In some cases, $R^B$ is $CO_2R^4$. In some cases, $R^B$ is C(O)$NH_2$. In some cases, $R^B$ is C(O)NHOH. In some cases, $R^B$ is C(O)$NHOR^5$. In some cases, $R^B$ is C(O)$NHR_5$. In some cases, $R^B$ is $CON(R^5)_2$.

In some cases, each $R^C$ is H. In some cases, each $R^C$ is OH. In some cases, one $R^C$ is OH. In some cases, each $R^C$ is $CO_2R^4$. In some cases, one $R^C$ is $CO_2R^4$.

In some cases, at least one $R^2$ is H. In some cases, each $R^2$ is H. In some cases, one or two $R^2$ are halo. In some cases, one $R^2$ is halo. In some cases, two $R^2$ are halo. In some cases, at least one $R^2$ is F. In some cases, each $R^2$ is F. In some cases, at least one $R^2$ is C. In some cases, each $R^2$ is C. In some cases, at least one $R^2$ is Br. In some cases, each $R^2$ is Br. In some cases, one $R^2$ is F and one $R^2$ is C. In some cases, one $R^2$ is C and one $R^2$ is Br. In some cases, one $R^2$ is F and one $R^2$ is Br. In some cases, at least one $R^2$ is $CF_3$. In some cases, each $R^2$ is $CF_3$. In some cases, at least one $R^2$ is isopropyl. In some cases, at least one $R^2$ is methoxy. In some cases, at least one $R^2$ is trifluoromethoxy.

In some cases, $R^4$ is H. In some cases, $R^4$ is $C_{1-6}$alkyl. In some cases, $R^4$ is methyl. In some cases, $R^4$ is ethyl. In some cases, $R^4$ is $C_{0-6}$alkylene-Ar.

In some cases, $R^5$ is H. In some cases, $R^5$ is —$C_{1-6}$alkyl. In some cases, $R^5$ is methyl. In some cases, $R^5$ is isopropyl. In some cases, $R^5$ is —OH. In some cases, $R^5$ is $C_{1-6}$alkoxy. In some cases, $R^5$ is —$C_{1-6}$alkoxy-$C_{6-10}$aryl. In some cases, $R^5$ is —$C_{0-6}$alkylene-$C_{6-10}$aryl. In some cases, $R^5$ is phenyl.

In some cases, $R^5$ is benzyl. In some cases, $R^5$ is naphthyl. In some cases, $R^5$ is —$C_{1-6}$ alkyl or $C_{6-10}$aryl substituted with $R^6$ or $OR^6$.

In some cases, $R^6$ is —$C_{1-6}$alkyl. In some cases, $R^6$ is —$C_{0-6}$alkylene-$C_{6-10}$aryl. In some cases, $R^6$ is —$C_{0-6}$alkylene-phenyl. In some cases, $R^6$ is substituted with one or more $R^7$.

In some cases, $R^7$ is H. In some cases, $R^7$ is —OH. In some cases, $R^7$ is —$CF_3$. In some cases, $R^7$ is phenyl. In some cases, $R^7$ is naphthyl.

It is understood that selections of values of each variable are those that result in the formation of stable or chemically feasible compounds.

Specific compounds contemplated include compounds in the following Tables. Compounds showing particular stereocenters indicate at least a relative stereoisomerism. Compounds having a chiral center without indication of a particular stereoisomerism indicate a mixture of stereocenters at that chiral center.

The compound can be a compound as listed in Table A, or a pharmaceutically acceptable salt thereof.

TABLE A

| Compound no. | Structure |
|---|---|
| 1 | 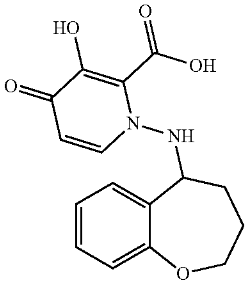 [SMILES: O=C(O)c1c(O)c(=O)ccn1NC1CCCOc2ccccc21] |
| 2 | 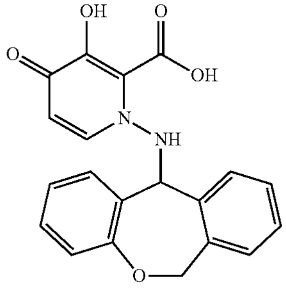 [SMILES: O=C(O)c1c(O)c(=O)ccn1NC1c2ccccc2COc2ccccc21] |
| 4 | 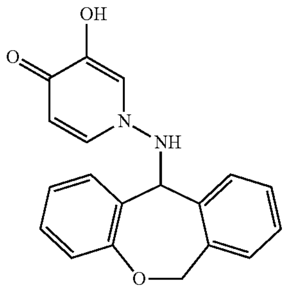 [SMILES: O=c1ccn(NC2c3ccccc3COc3ccccc32)cc1O] |

TABLE A-continued
| Compound no. | Structure |
| --- | --- |
| 5 | 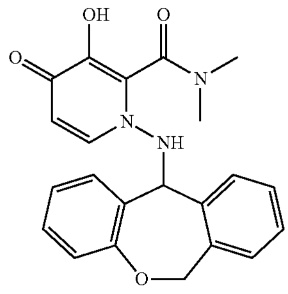 [SMILES: CN(C)C(=O)c1c(O)c(=O)ccn1NC1c2ccccc2COc2ccccc21] |
| 6 | 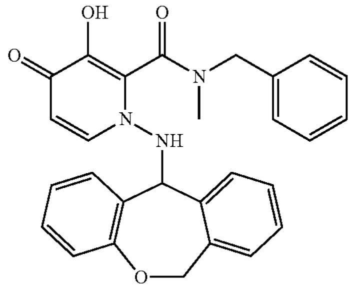 [SMILES: CN(Cc1ccccc1)C(=O)c1c(O)c(=O)ccn1NC1c2ccccc2COc2ccccc21] |
| 8 | 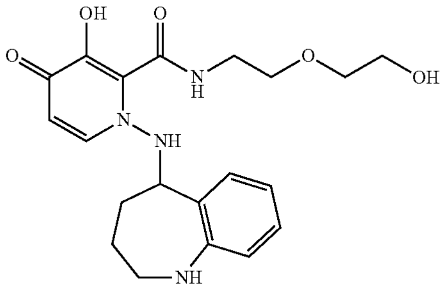 [SMILES: O=C(NCCOCCO)c1c(O)c(=O)ccn1NC1CCCNc2ccccc21] |
| 9 | 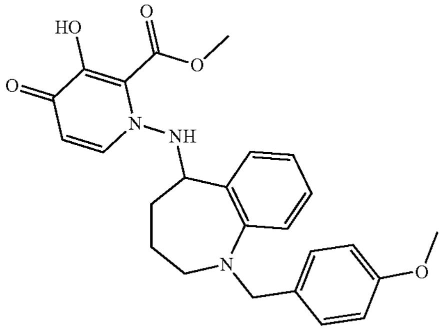 [SMILES: COC(=O)c1c(O)c(=O)ccn1NC1CCCN(Cc2ccc(OC)cc2)c2ccccc21] |
| 10 | 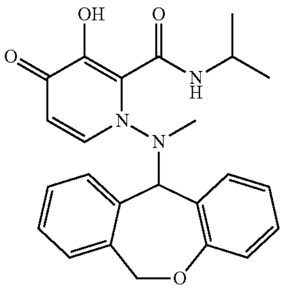 [SMILES: CC(C)NC(=O)c1c(O)c(=O)ccn1N(C)C1c2ccccc2COc2ccccc21] |
TABLE A-continued
| Compound no. | Structure |
| --- | --- |
| 11 | 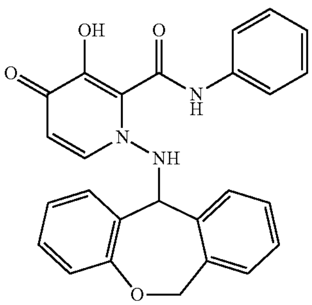 [SMILES: O=C(Nc1ccccc1)c1c(O)c(=O)ccn1NC1c2ccccc2COc2ccccc21] |
| 12 | 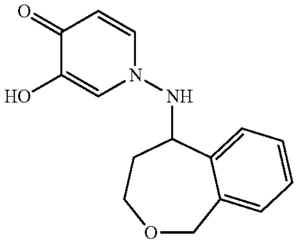 [SMILES: O=c1ccn(NC2CCOCc3ccccc32)cc1O] |
| 13 | 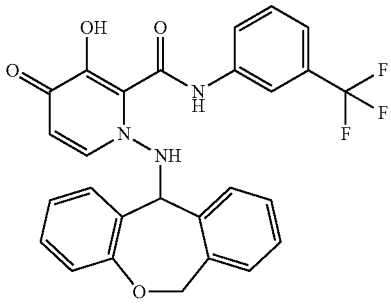 [SMILES: O=C(Nc1cccc(C(F)(F)F)c1)c1c(O)c(=O)ccn1NC1c2ccccc2COc2ccccc21] |
| 14 | 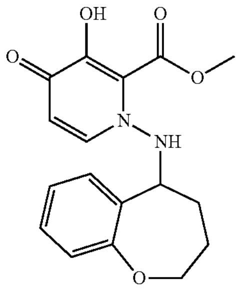 [SMILES: COC(=O)c1c(O)c(=O)ccn1NC1CCCOc2ccccc21] |
| 15 | 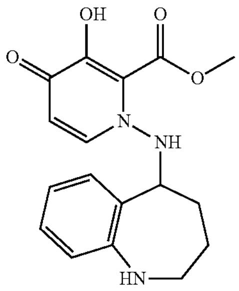 [SMILES: COC(=O)c1c(O)c(=O)ccn1NC1CCCNc2ccccc21] |

TABLE A-continued
| Compound no. | Structure |
|---|---|
| 16 | 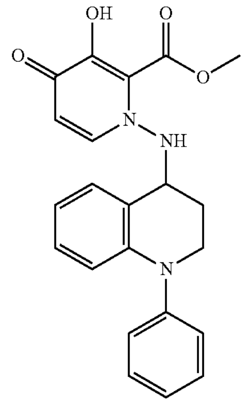 [SMILES: COC(=O)c1c(O)c(=O)ccn1NC1CCN(c2ccccc2)c2ccccc21] |
| 17 | 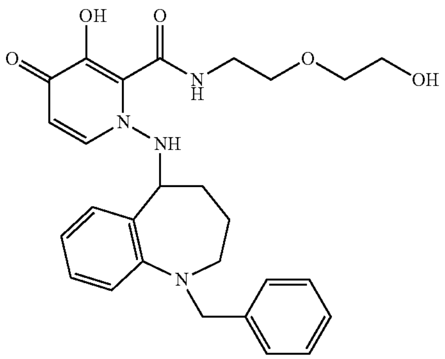 [SMILES: O=C(NCCOCCO)c1c(O)c(=O)ccn1NC1CCCN(Cc2ccccc2)c2ccccc21] |
| 18 | 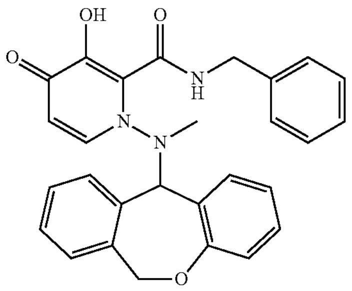 [SMILES: CN(C1c2ccccc2COc2ccccc21)n1ccc(=O)c(O)c1C(=O)NCc1ccccc1] |
| 19 | 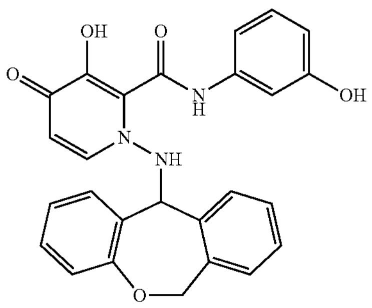 [SMILES: O=C(Nc1cccc(O)c1)c1c(O)c(=O)ccn1NC1c2ccccc2COc2ccccc21] |
TABLE A-continued
| Compound no. | Structure |
|---|---|
| 20 | 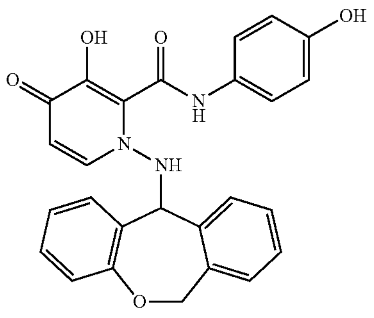 [SMILES: O=C(Nc1ccc(O)cc1)c1c(O)c(=O)ccn1NC1c2ccccc2COc2ccccc21] |
| 21 | 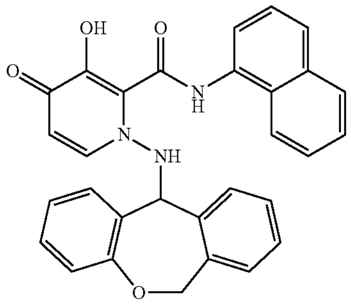 [SMILES: O=C(Nc1cccc2ccccc12)c1c(O)c(=O)ccn1NC1c2ccccc2COc2ccccc21] |
| 22 | 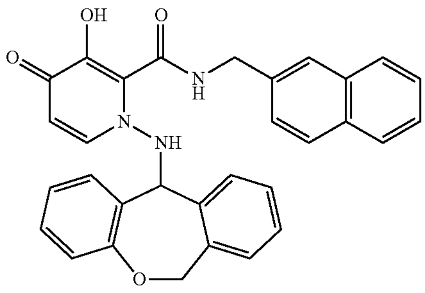 [SMILES: O=C(NCc1ccc2ccccc2c1)c1c(O)c(=O)ccn1NC1c2ccccc2COc2ccccc21] |
| 23 | 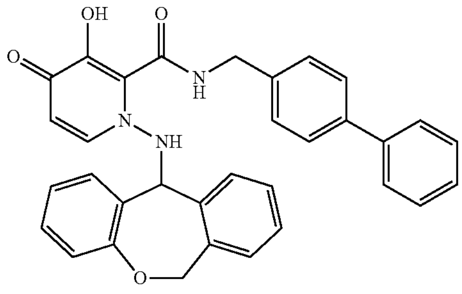 [SMILES: O=C(NCc1ccc(-c2ccccc2)cc1)c1c(O)c(=O)ccn1NC1c2ccccc2COc2ccccc21] |
| 24 | 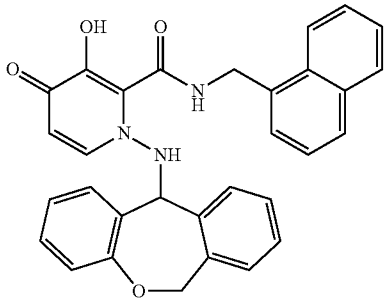 [SMILES: O=C(NCc1cccc2ccccc12)c1c(O)c(=O)ccn1NC1c2ccccc2COc2ccccc21] |

TABLE A-continued
| Compound no. | Structure |
|---|---|
| 25 | 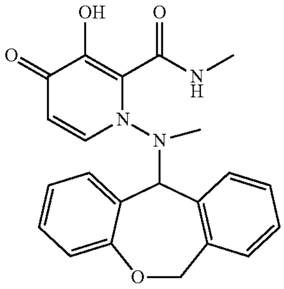 [SMILES: CNC(=O)c1c(O)c(=O)ccn1N(C)C1c2ccccc2COc2ccccc21] |
| 26 | 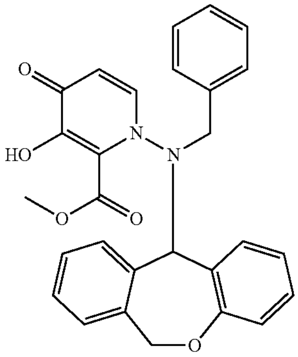 [SMILES: COC(=O)c1c(O)c(=O)ccn1N(Cc1ccccc1)C1c2ccccc2COc2ccccc21] |
| 27 | 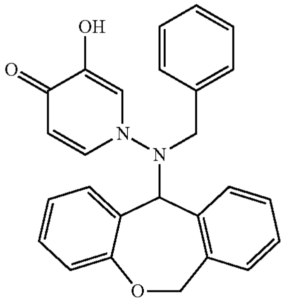 [SMILES: O=c1ccn(N(Cc2ccccc2)C2c3ccccc3COc3ccccc32)cc1O] |
| 28 | 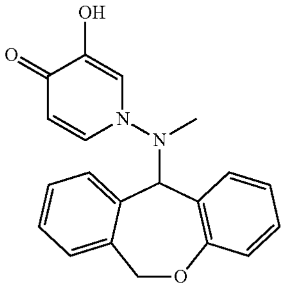 [SMILES: CN(C1c2ccccc2COc2ccccc21)n1ccc(=O)c(O)c1] |
| 29 | 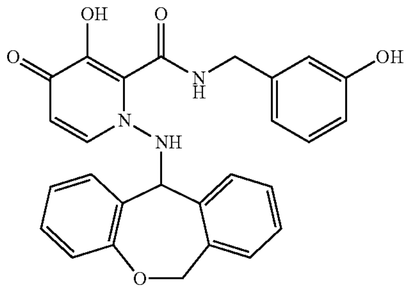 [SMILES: O=C(NCc1cccc(O)c1)c1c(O)c(=O)ccn1NC1c2ccccc2COc2ccccc21] |
TABLE A-continued
| Compound no. | Structure |
|---|---|
| 30 | 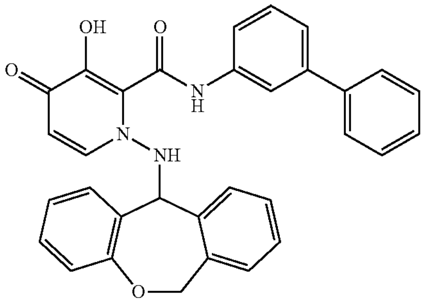 [SMILES: O=C(Nc1cccc(-c2ccccc2)c1)c1c(O)c(=O)ccn1NC1c2ccccc2COc2ccccc21] |
| 31 | 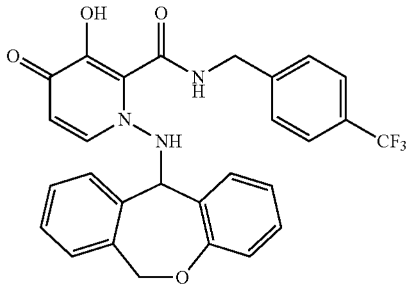 [SMILES: O=C(NCc1ccc(C(F)(F)F)cc1)c1c(O)c(=O)ccn1NC1c2ccccc2COc2ccccc21] |
| 32 | 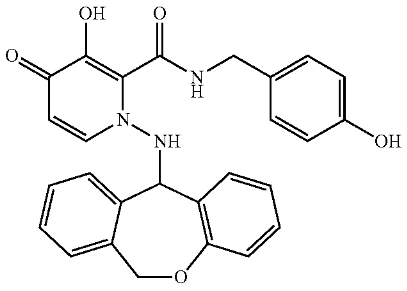 [SMILES: O=C(NCc1ccc(O)cc1)c1c(O)c(=O)ccn1NC1c2ccccc2COc2ccccc21] |
| 33 | 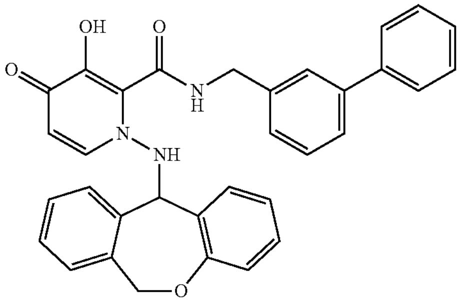 [SMILES: O=C(NCc1cccc(-c2ccccc2)c1)c1c(O)c(=O)ccn1NC1c2ccccc2COc2ccccc21] |
| 34 | 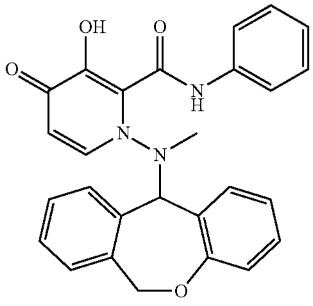 [SMILES: CN(C1c2ccccc2COc2ccccc21)n1ccc(=O)c(O)c1C(=O)Nc1ccccc1] |

TABLE A-continued
| Compound no. | Structure |
|---|---|
| 35 | 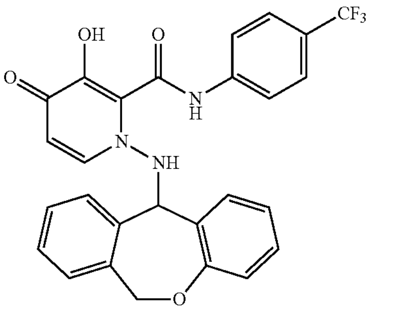 [SMILES: O=C(Nc1ccc(C(F)(F)F)cc1)c1c(O)c(=O)ccn1NC1c2ccccc2COc2ccccc21] |
| 36 | 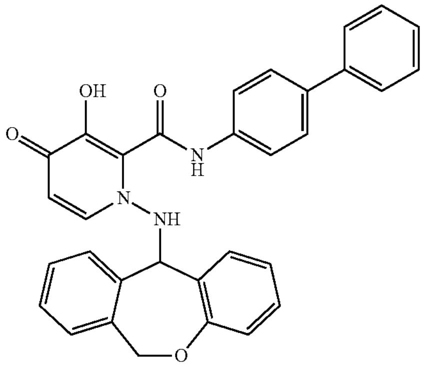 [SMILES: O=C(Nc1ccc(-c2ccccc2)cc1)c1c(O)c(=O)ccn1NC1c2ccccc2COc2ccccc21] |
| 37 | 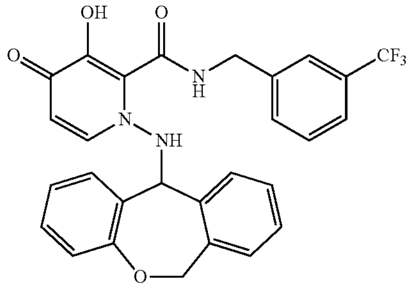 [SMILES: O=C(NCc1cccc(C(F)(F)F)c1)c1c(O)c(=O)ccn1NC1c2ccccc2COc2ccccc21] |
| 38 | 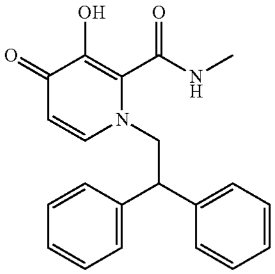 [SMILES: CNC(=O)c1c(O)c(=O)ccn1CC(c1ccccc1)c1ccccc1] |
| 39 | 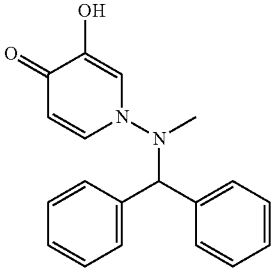 [SMILES: CN(C(c1ccccc1)c1ccccc1)n1ccc(=O)c(O)c1] |
TABLE A-continued
| Compound no. | Structure |
|---|---|
| 40 | 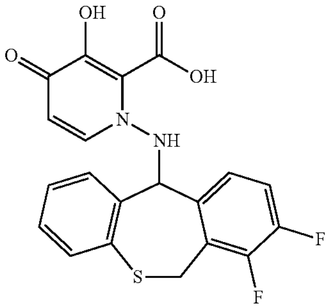 [SMILES: O=C(O)c1c(O)c(=O)ccn1NC1c2ccccc2SCc2c1ccc(F)c2F] |
| 41 | 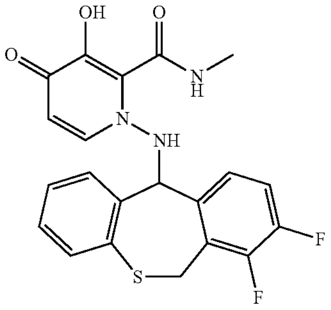 [SMILES: CNC(=O)c1c(O)c(=O)ccn1NC1c2ccccc2SCc2c1ccc(F)c2F] |
| 42 | 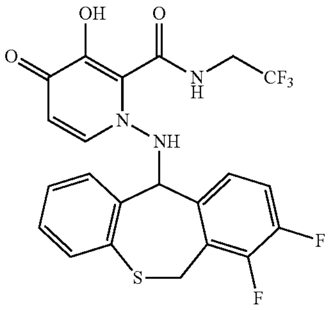 [SMILES: O=C(NCC(F)(F)F)c1c(O)c(=O)ccn1NC1c2ccccc2SCc2c1ccc(F)c2F] |
| 43 | 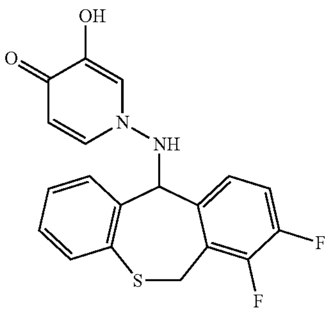 [SMILES: O=c1ccn(NC2c3ccccc3SCc3c2ccc(F)c3F)cc1O] |

TABLE A-continued
| Compound no. | Structure |
| --- | --- |
| 44 | 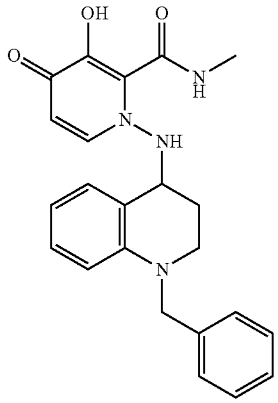 [SMILES: CNC(=O)c1c(O)c(=O)ccn1NC1CCN(Cc2ccccc2)c2ccccc21] |
| 45 | 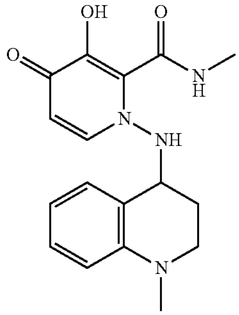 [SMILES: CNC(=O)c1c(O)c(=O)ccn1NC1CCN(C)c2ccccc21] |
| 46 | 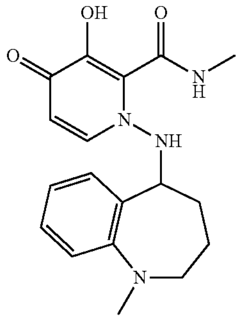 [SMILES: CNC(=O)c1c(O)c(=O)ccn1NC1CCCN(C)c2ccccc21] |
| 47 | 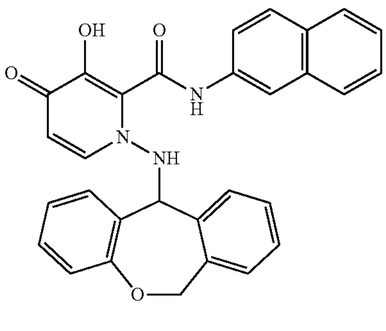 [SMILES: O=C(Nc1ccc2ccccc2c1)c1c(O)c(=O)ccn1NC1c2ccccc2COc2ccccc21] |
TABLE A-continued
| Compound no. | Structure |
| --- | --- |
| 48 | 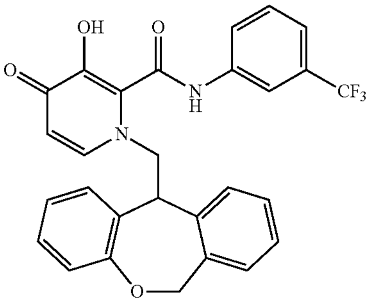 [SMILES: O=C(Nc1cccc(C(F)(F)F)c1)c1c(O)c(=O)ccn1CC1c2ccccc2COc2ccccc21] |
| 49 | 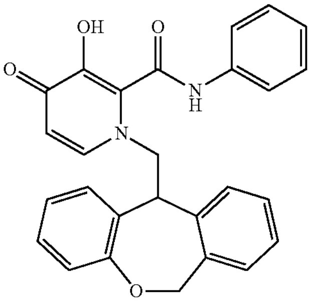 [SMILES: O=C(Nc1ccccc1)c1c(O)c(=O)ccn1CC1c2ccccc2COc2ccccc21] |
| 50 | 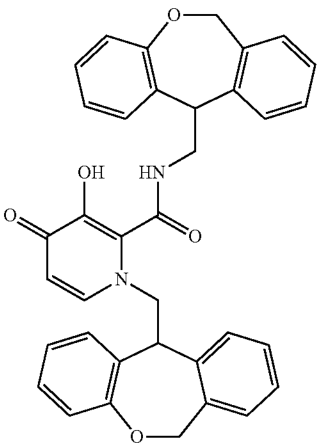 [SMILES: O=C(NCC1c2ccccc2COc2ccccc21)c1c(O)c(=O)ccn1CC1c2ccccc2COc2ccccc21] |
| 51 | 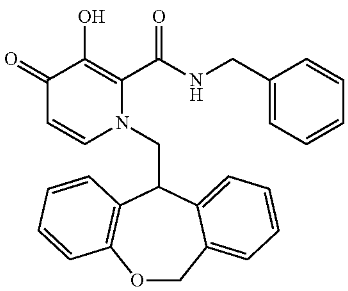 [SMILES: O=C(NCc1ccccc1)c1c(O)c(=O)ccn1CC1c2ccccc2COc2ccccc21] |

TABLE A-continued
| Compound no. | Structure |
|---|---|
| 52 | 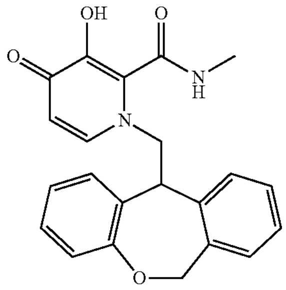 [SMILES: CNC(=O)c1c(O)c(=O)ccn1CC1c2ccccc2COc2ccccc21] |
| 54 | 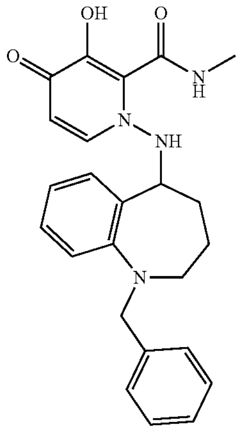 [SMILES: CNC(=O)c1c(O)c(=O)ccn1NC1CCCN(Cc2ccccc2)c2ccccc21] |
| 56 | 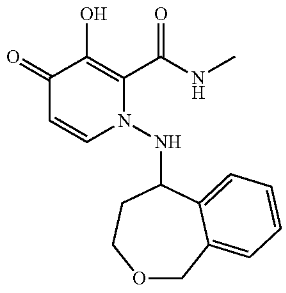 [SMILES: CNC(=O)c1c(O)c(=O)ccn1NC1CCOCc2ccccc21] |
| 57 | 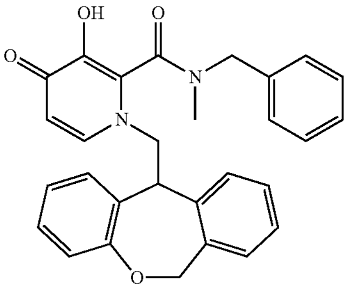 [SMILES: CN(Cc1ccccc1)C(=O)c1c(O)c(=O)ccn1CC1c2ccccc2COc2ccccc21] |
TABLE A-continued
| Compound no. | Structure |
|---|---|
| 58 | 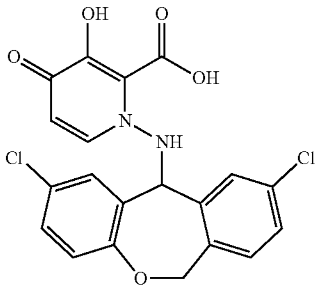 [SMILES: O=C(O)c1c(O)c(=O)ccn1NC1c2cc(Cl)ccc2COc2ccc(Cl)cc21] |
| 59 | 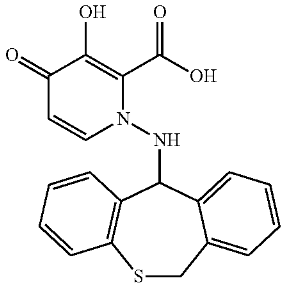 |
| 60 | 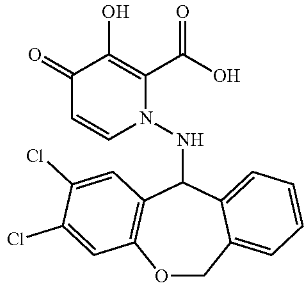 [SMILES: O=C(O)c1c(O)c(=O)ccn1NC1c2ccccc2COc2cc(Cl)c(Cl)cc21] |
| 61 | 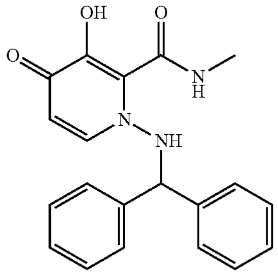 [SMILES: CNC(=O)c1c(O)c(=O)ccn1NC(c1ccccc1)c1ccccc1] |
| 65 | 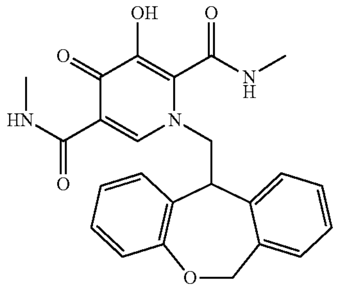 [SMILES: CNC(=O)c1cn(CC2c3ccccc3COc3ccccc32)c(C(=O)NC)c(O)c1=O] |

TABLE A-continued
| Compound no. | Structure |
|---|---|
| 66 | 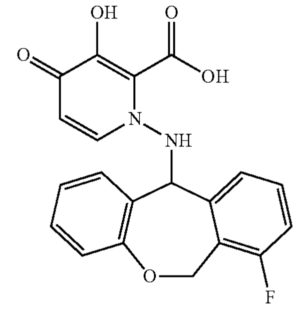 [SMILES: O=C(O)c1c(O)c(=O)ccn1NC1c2ccccc2OCc2c(F)cccc21] |
| 67 | 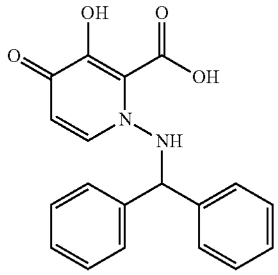 [SMILES: O=C(O)c1c(O)c(=O)ccn1NC(c1ccccc1)c1ccccc1] |
| 68 | 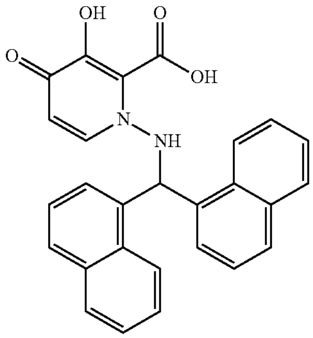 [SMILES: O=C(O)c1c(O)c(=O)ccn1NC(c1cccc2ccccc12)c1cccc2ccccc12] |
| 69 | 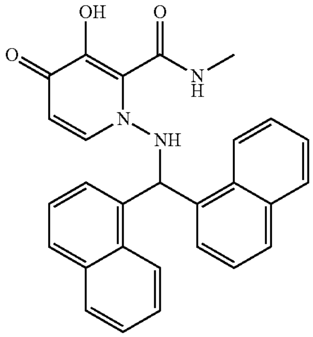 [SMILES: CNC(=O)c1c(O)c(=O)ccn1NC(c1cccc2ccccc12)c1cccc2ccccc12] |
TABLE A-continued
| Compound no. | Structure |
|---|---|
| 72 | 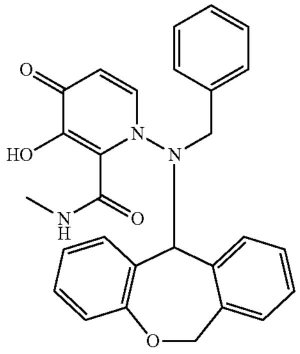 [SMILES: CNC(=O)c1c(O)c(=O)ccn1N(Cc1ccccc1)C1c2ccccc2COc2ccccc21] |
| 73 | 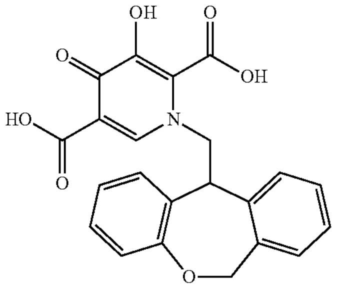 [SMILES: O=C(O)c1cn(CC2c3ccccc3COc3ccccc32)c(C(=O)O)c(O)c1=O] |
| 74 | 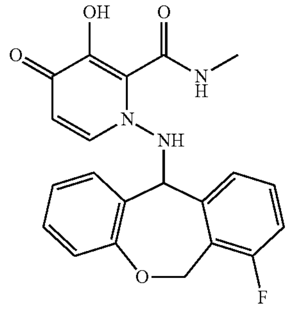 [SMILES: CNC(=O)c1c(O)c(=O)ccn1NC1c2ccccc2OCc2c(F)cccc21] |
| 75 | 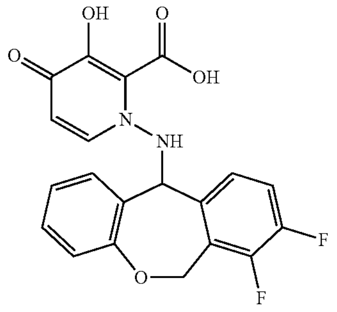 [SMILES: O=C(O)c1c(O)c(=O)ccn1NC1c2ccccc2OCc2c1ccc(F)c2F] |
| 76 | 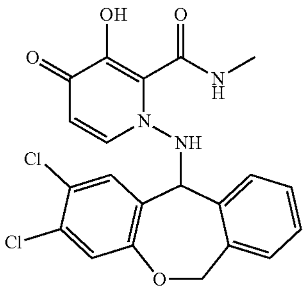 [SMILES: CNC(=O)c1c(O)c(=O)ccn1NC1c2ccccc2COc2cc(Cl)c(Cl)cc21] |

TABLE A-continued
| Compound no. | Structure |
|---|---|
| 77 | 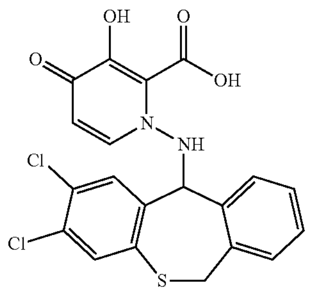 [SMILES: O=C(O)c1c(O)c(=O)ccn1NC1c2ccccc2CSc2cc(Cl)c(Cl)cc21] |
| 78 | 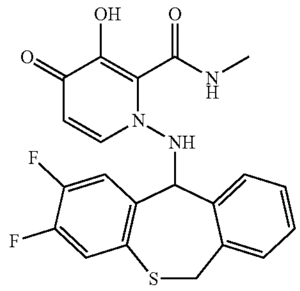 [SMILES: CNC(=O)c1c(O)c(=O)ccn1NC1c2ccccc2CSc2cc(F)c(F)cc21] |
| 79 | 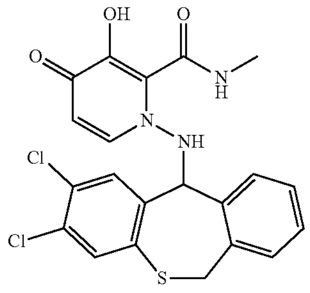 [SMILES: CNC(=O)c1c(O)c(=O)ccn1NC1c2ccccc2CSc2cc(Cl)c(Cl)cc21] |
| 80 | 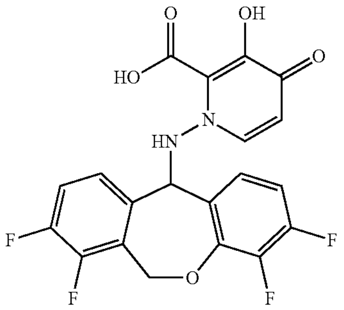 [SMILES: O=C(O)c1c(O)c(=O)ccn1NC1c2ccc(F)c(F)c2COc2c1ccc(F)c2F] |
| 81 | 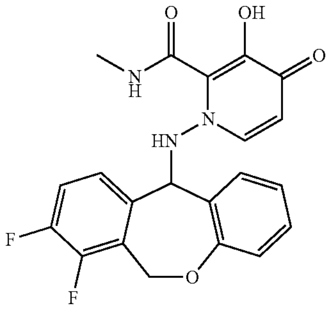 [SMILES: CNC(=O)c1c(O)c(=O)ccn1NC1c2ccccc2OCc2c1ccc(F)c2F] |
TABLE A-continued
| Compound no. | Structure |
|---|---|
| 82 | 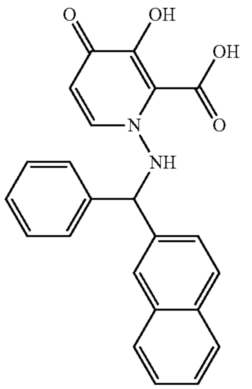 [SMILES: O=C(O)c1c(O)c(=O)ccn1NC(c1ccccc1)c1ccc2ccccc2c1] |
| 83 | 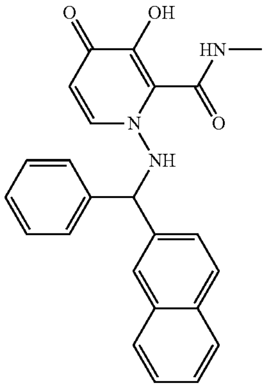 [SMILES: CNC(=O)c1c(O)c(=O)ccn1NC(c1ccccc1)c1ccc2ccccc2c1] |
| 84 | 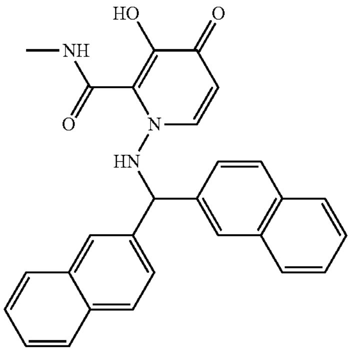 [SMILES: CNC(=O)c1c(O)c(=O)ccn1NC(c1ccc2ccccc2c1)c1ccc2ccccc2c1] |
| 86 | 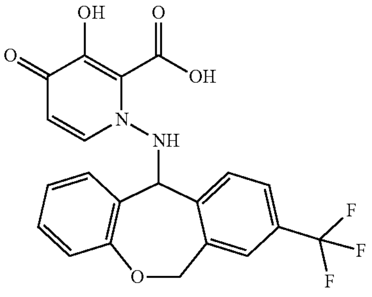 [SMILES: O=C(O)c1c(O)c(=O)ccn1NC1c2ccc(C(F)(F)F)cc2COc2ccccc21] |

TABLE A-continued
| Compound no. | Structure |
| --- | --- |
| 87 | 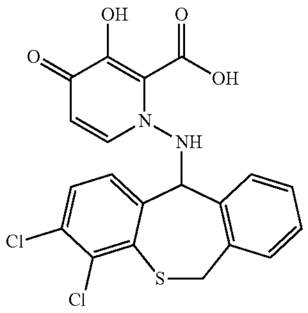 [SMILES: O=C(O)c1c(O)c(=O)ccn1NC1c2ccccc2CSc2c1ccc(Cl)c2Cl] |
| 88 | 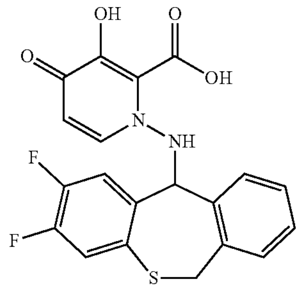 [SMILES: O=C(O)c1c(O)c(=O)ccn1NC1c2ccccc2CSc2cc(F)c(F)cc21] |
| 89 | 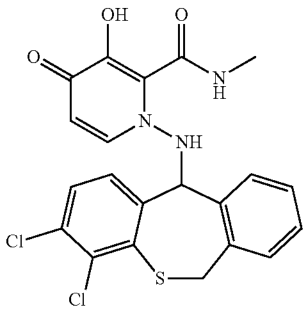 [SMILES: CNC(=O)c1c(O)c(=O)ccn1NC1c2ccccc2CSc2c1ccc(Cl)c2Cl] |
| 90 | 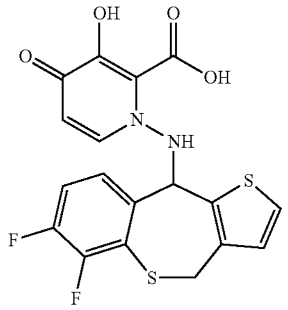 [SMILES: O=C(O)c1c(O)c(=O)ccn1NC1c2ccc(F)c(F)c2SCc2ccsc21] |
| 91 | 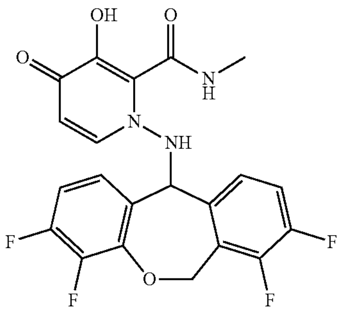 |
TABLE A-continued
| Compound no. | Structure |
| --- | --- |
| 93 | 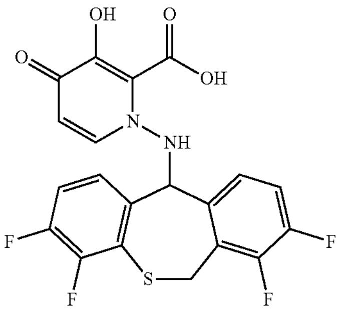 [SMILES: O=C(O)c1c(O)c(=O)ccn1NC1c2ccc(F)c(F)c2CSc2c1ccc(F)c2F] |
| 94 | 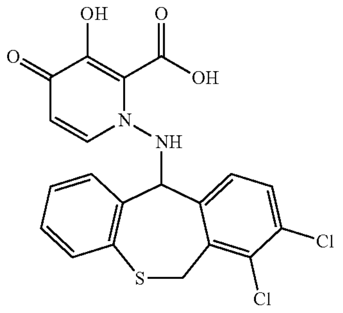 |
| 95 | 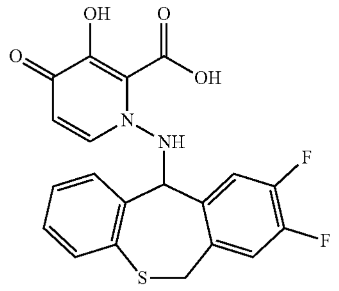 [SMILES: O=C(O)c1c(O)c(=O)ccn1NC1c2cc(F)c(F)cc2CSc2ccccc21] |
| 96 | 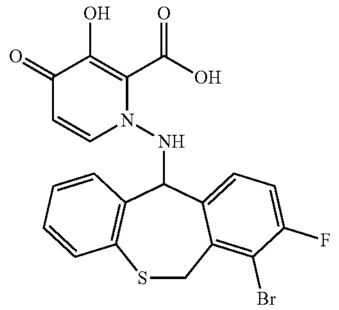 [SMILES: O=C(O)c1c(O)c(=O)ccn1NC1c2ccccc2SCc2c1ccc(F)c2Br] |
| 97 | 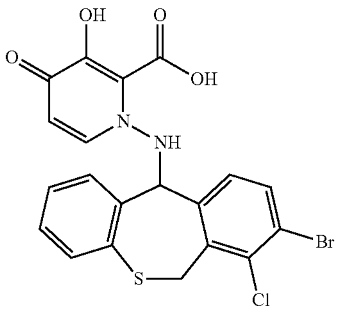 [SMILES: O=C(O)c1c(O)c(=O)ccn1NC1c2ccccc2SCc2c1ccc(Br)c2Cl] |

TABLE A-continued
| Compound no. | Structure |
|---|---|
| 98 | 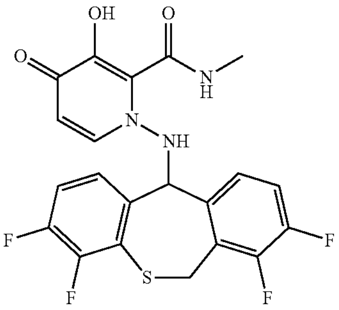 |
| 99 | 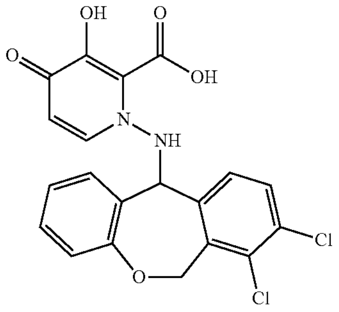 [SMILES: O=C(O)c1c(O)c(=O)ccn1NC1c2ccccc2OCc2c1ccc(Cl)c2Cl] |
| 100 | 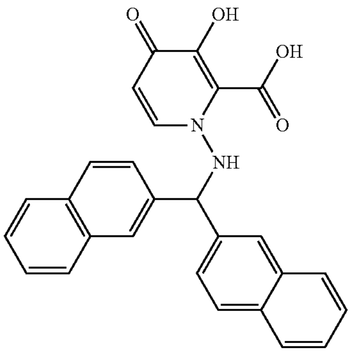 [SMILES: O=C(O)c1c(O)c(=O)ccn1NC(c1ccc2ccccc2c1)c1ccc2ccccc2c1] |
| 101 | 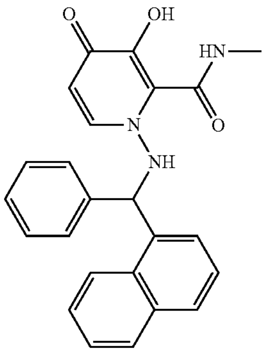 [SMILES: CNC(=O)c1c(O)c(=O)ccn1NC(c1ccccc1)c1cccc2ccccc12] |
TABLE A-continued
| Compound no. | Structure |
|---|---|
| 102 | 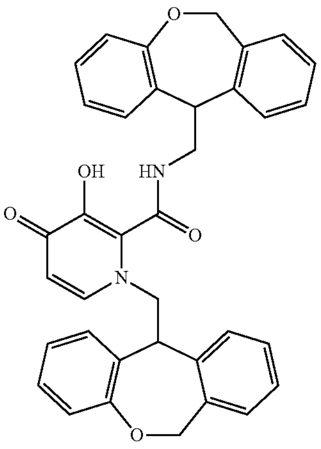 [SMILES: O=C(NCC1c2ccccc2COc2ccccc21)c1c(O)c(=O)ccn1CC1c2ccccc2COc2ccccc21] |
| 103 | 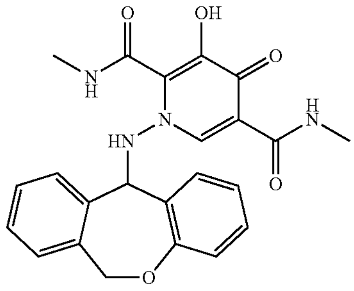 [SMILES: CNC(=O)c1cn(NC2c3ccccc3COc3ccccc32)c(C(=O)NC)c(O)c1=O] |
| 104 | 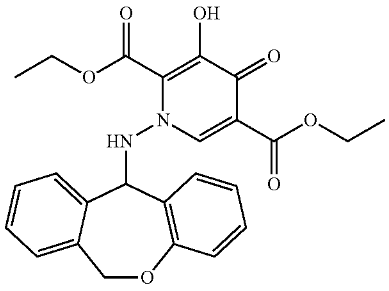 [SMILES: CCOC(=O)c1cn(NC2c3ccccc3COc3ccccc32)c(C(=O)OCC)c(O)c1=O] |
| 105 | 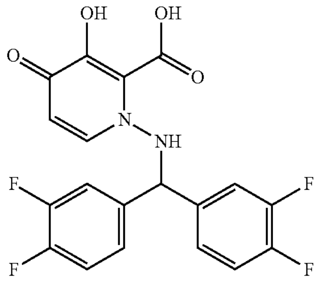 [SMILES: O=C(O)c1c(O)c(=O)ccn1NC(c1ccc(F)c(F)c1)c1ccc(F)c(F)c1] |

TABLE A-continued
| Compound no. | Structure |
|---|---|
| 106 | 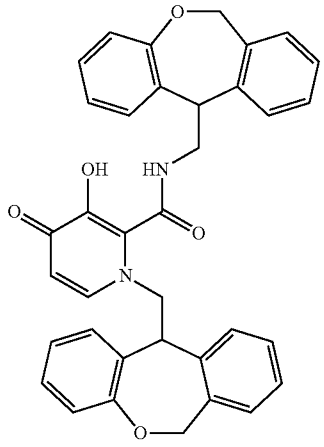 [SMILES: O=C(NCC1c2ccccc2COc2ccccc21)c1c(O)c(=O)ccn1CC1c2ccccc2COc2ccccc21] |
| 107 | 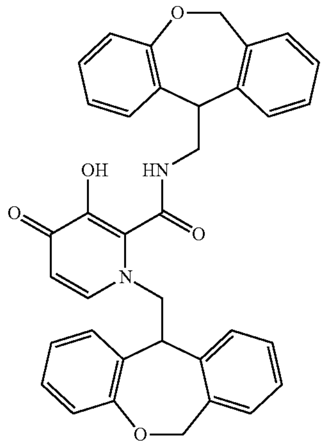 [SMILES: O=C(NCC1c2ccccc2COc2ccccc21)c1c(O)c(=O)ccn1CC1c2ccccc2COc2ccccc21] |
| 108 | 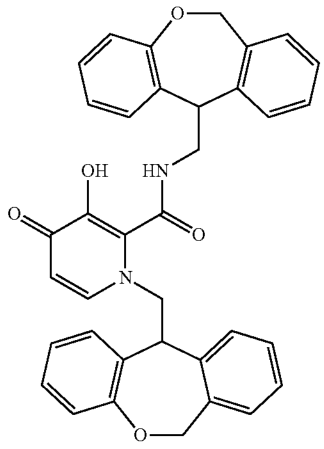 [SMILES: O=C(NCC1c2ccccc2COc2ccccc21)c1c(O)c(=O)ccn1CC1c2ccccc2COc2ccccc21] |
TABLE A-continued
| Compound no. | Structure |
|---|---|
| 109 | 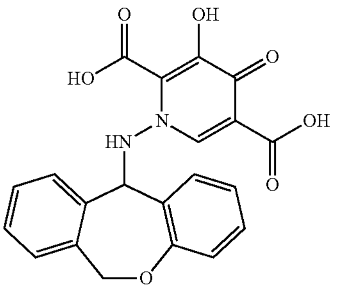 [SMILES: O=C(O)c1cn(NC2c3ccccc3COc3ccccc32)c(C(=O)O)c(O)c1=O] |
| 110 | 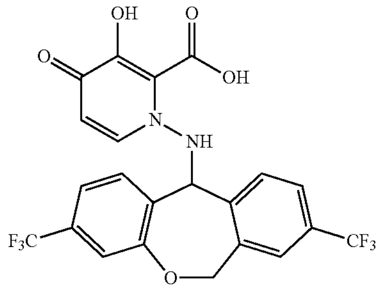 [SMILES: O=C(O)c1c(O)c(=O)ccn1NC1c2ccc(C(F)(F)F)cc2COc2cc(C(F)(F)F)ccc21] |
| 111 | 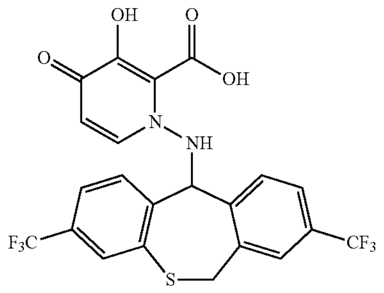 [SMILES: O=C(O)c1c(O)c(=O)ccn1NC1c2ccc(C(F)(F)F)cc2CSc2cc(C(F)(F)F)ccc21] |
| 112 | 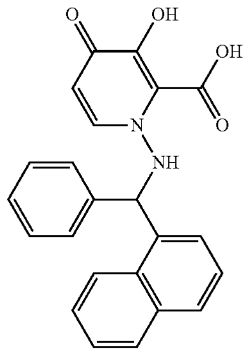 [SMILES: O=C(O)c1c(O)c(=O)ccn1NC(c1ccccc1)c1cccc2ccccc12] |
| 113 | 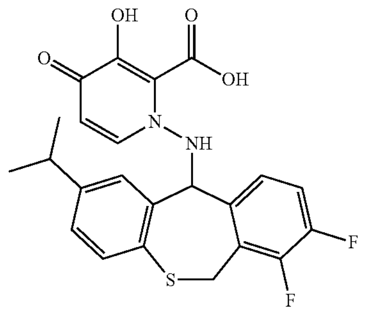 [SMILES: CC(C)c1ccc2c(c1)C(Nn1ccc(=O)c(O)c1C(=O)O)c1ccc(F)c(F)c1CS2] |

TABLE A-continued
| Compound no. | Structure |
| --- | --- |
| 114 | 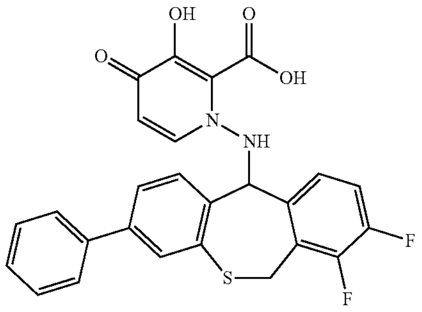 [SMILES: O=C(O)c1c(O)c(=O)ccn1NC1c2ccc(-c3ccccc3)cc2SCc2c1ccc(F)c2F] |
| 115 | 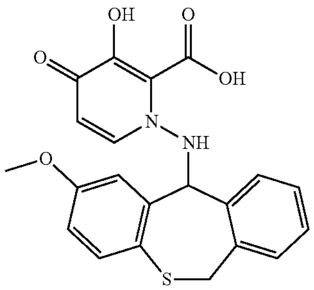 [SMILES: COc1ccc2c(c1)C(Nn1ccc(=O)c(O)c1C(=O)O)c1ccccc1CS2] |
| 116 | 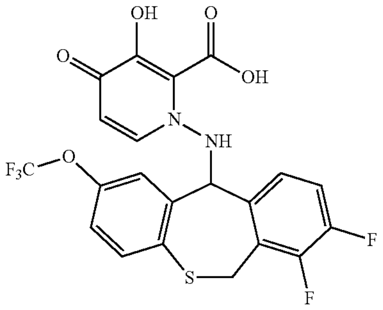 [SMILES: O=C(O)c1c(O)c(=O)ccn1NC1c2cc(OC(F)(F)F)ccc2SCc2c1ccc(F)c2F] |
| 117 | 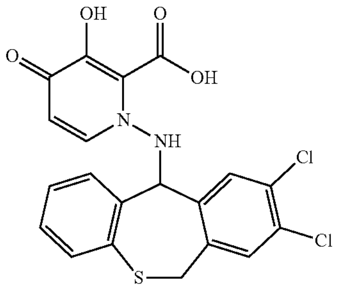 [SMILES: O=C(O)c1c(O)c(=O)ccn1NC1c2cc(Cl)c(Cl)cc2CSc2ccccc21] |
| 118 | 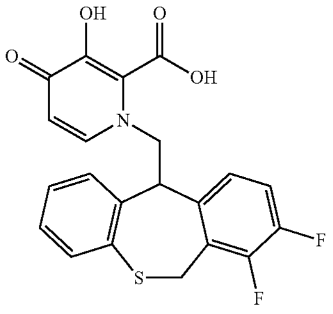 [SMILES: O=C(O)c1c(O)c(=O)ccn1CC1c2ccccc2SCc2c1ccc(F)c2F] |
TABLE A-continued
| Compound no. | Structure |
| --- | --- |
| 120 | 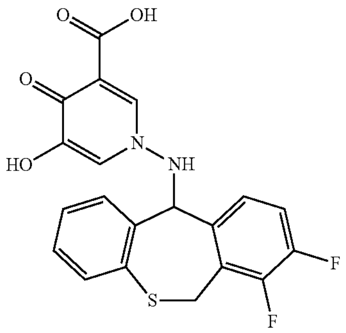 [SMILES: O=C(O)c1cn(NC2c3ccccc3SCc3c2ccc(F)c3F)cc(O)c1=O] |
| 121 | 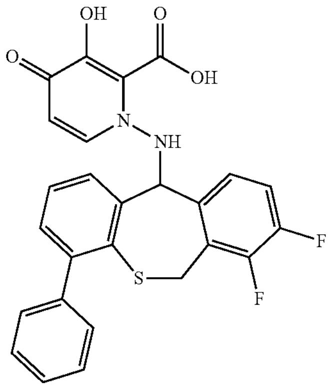 [SMILES: O=C(O)c1c(O)c(=O)ccn1NC1c2ccc(F)c(F)c2CSc2c(-c3ccccc3)cccc21] |
| 122 | 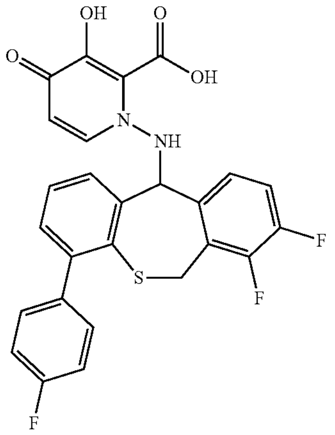 [SMILES: O=C(O)c1c(O)c(=O)ccn1NC1c2ccc(F)c(F)c2CSc2c(-c3ccc(F)cc3)cccc21] |
| 123 | 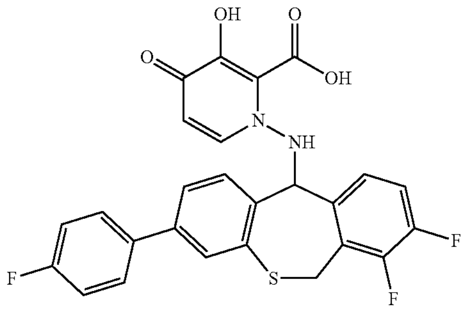 [SMILES: O=C(O)c1c(O)c(=O)ccn1NC1c2ccc(-c3ccc(F)cc3)cc2SCc2c1ccc(F)c2F] |

TABLE A-continued

| Compound no. | Structure |
|---|---|
| 126 | 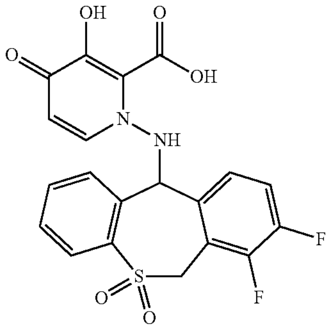 [SMILES: O=C(O)c1c(O)c(=O)ccn1NC1c2ccccc2S(=O)(=O)Cc2c1ccc(F)c2F] |
| 127 | 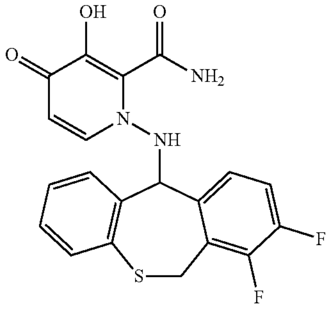 [SMILES: NC(=O)c1c(O)c(=O)ccn1NC1c2ccccc2SCc2c1ccc(F)c2F] |
| 128 | 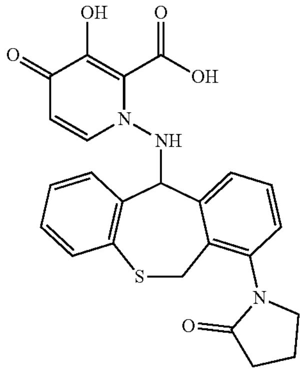 [SMILES: O=C(O)c1c(O)c(=O)ccn1NC1c2ccccc2SCc2c1cccc2N1CCCC1=O] |
| 129 | 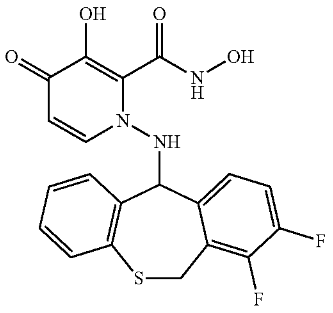 [SMILES: O=C(NO)c1c(O)c(=O)ccn1NC1c2ccccc2SCc2c1ccc(F)c2F] |

TABLE A-continued

| Compound no. | Structure |
|---|---|
| 130 | 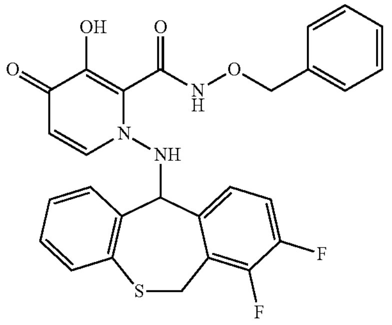 [SMILES: O=C(NOCc1ccccc1)c1c(O)c(=O)ccn1NC1c2ccccc2SCc2c1ccc(F)c2F] |

In some cases, the compound is selected from 1, 2, 13, 22, 23, 40, 42, 58, 59, 60, 66, 73, 75, 77, 78, 80, 87, 88, 90, 93, 94, 95, 96, 97, 99, 114, 115, 116, 117, 118, 120, 123, 126, and 130, or a pharmaceutically acceptable salt thereof.

In some cases, the compounds disclosed herein are stereoisomers. "Stereoisomers" refer to compounds that differ in the chirality of one or more stereocenters. Stereoisomers include enantiomers and diastereomers. The compounds disclosed herein can exist as a single stereoisomer, or as a mixture of stereoisomers. Stereochemistry of the compounds shown in the Tables above is relative stereochemistry, not absolute, unless discussed otherwise. As indicated herein, a single stereoisomer, diastereomer, or enantiomer refers to a compound that is at least more than 50% of the indicated stereoisomer, diastereomer, or enantiomer, and more preferably at least 90% of the indicated stereoisomer, diastereomer, or enantiomer.

The compounds disclosed herein can be useful as inhibitors of influenza virus replication in biological samples or in a patient. These compounds can also be useful in reducing the amount of influenza viruses (viral titer) in a biological sample or in a patient. They can also be useful for therapeutic and prophylactic treatment of infections caused by the influenza viruses in a biological sample or in a patient.

Pharmaceutically Acceptable Salts

The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the disclosure or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This disclosure also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that a compound disclosed herein can be present as a mixture/combination of different pharmaceutically acceptable salts. Also contemplated are mixtures/combinations of compounds in free form and pharmaceutically acceptable salts.

II. Methods of Treatment

Provided herein are uses of a compound described herein. The compounds described herein or pharmaceutically acceptable salts thereof can be used to reduce viral titer in a biological sample (e.g. an infected cell culture) or in humans (e.g. lung viral titer in a patient).

The terms "influenza virus mediated condition", "influenza infection", or "Influenza", as used herein, are used interchangeable to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenzavirus A, Influenzavirus B, Influenzavirus C, Isavirus and Thogotovirus. Influenzavirus A genus has one species, influenza A virus which can be subdivided into different serotypes based on the antibody response to these viruses: H1N1, H2N2, H3N2, H5N1, H7N7, H1N2, H9N2, H7N2, H7N3 and H10N7. Influenzavirus B genus has one species, influenza B virus. Influenza B almost exclusively infects humans and is less common than influenza A. Influenzavirus C genus has one species, Influenzavirus C virus, which infects humans and pigs and can cause severe illness and local epidemics. However, Influenzavirus C is less common than the other types and usually seems to cause mild disease in children.

In some embodiments, the compounds used herein are for treatment of influenza or influenza viruses which are associated with Influenzavirus A or B. In some embodiments, influenza or influenza viruses are associated with Influenzavirus A. In some specific embodiments, Influenzavirus A is H1N1, H2N2, H3N2 or H5N1.

In some embodiments, the compounds disclosed herein can be used in the treatment of influenza, wherein the compound binds to free virus, binds to pre-mRNA bound PB2, or binds to trimeric polymerase complex. In some cases, the compound can target all three (free virus, pre-mRNA bound PB2, and trimeric polymerase complex).

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, Headache, irritated watering eyes, reddened eyes, skin (especially face), mouth, throat and nose, abdominal pain (in children with influenza B). Symptoms of influenza are non-specific, overlapping with many pathogens ("influenza-like illness). Usually, laboratory data is needed in order to confirm the diagnosis.

The terms, "disease", "disorder", and "condition" may be used interchangeably here to refer to an influenza virus mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

As used herein, "multiplicity of infection" or "MOI" is the ratio of infectious agents (e.g. phage or virus) to infection targets (e.g. cell). For example, when referring to a group of cells inoculated with infectious virus particles, the multiplicity of infection or MOI is the ratio defined by the number of infectious virus particles deposited in a well divided by the number of target cells present in that well.

As used herein the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

Influenza virus replication can be measured by any suitable method known in the art. For example, influenza viral titre in a biological sample (e.g. an infected cell culture) or in humans (e.g. lung viral titre in a patient) can be measured. More specifically, for cell based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used in the disclosure depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically 1/10 to 1/1000), the virus is allowed to go through several rounds of replication over 48-72 hours, then the amount of cell death is measured using a decrease in cellular ATP content compared to uninfected controls. A second type of cell assay that can be employed in the disclosure depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer (or titre)" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}$, $10^{-2}$, $10^{-3}$, . . . , $10^{-8}$. The lowest concentration of virus that still infects cells is the viral titer.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the disclosure). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "chemotherapy" refers to the use of medications, e.g. small molecule drugs (rather than "vaccines") for treating a disorder or disease.

The terms "prophylaxis" or "prophylactic use" and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g. small molecule drugs (rather than "vaccines") for the prevention of a disorder or disease.

As used herein, prophylactic use includes the use in situations in which an outbreak has been detected, to prevent contagion or spread of the infection in places where a lot of people that are at high risk of serious influenza complications live in close contact with each other (e.g. in a hospital ward, daycare center, prison, nursing home, etc.). It also includes the use among populations who require protection from the influenza but who either do not get protection after vaccination (e.g. due to weak immune system), or when the vaccine is unavailable to them, or when they cannot get the vaccine because of side effects. It also includes use during the two weeks following vaccination, since during that time the vaccine is still ineffective. Prophylactic use may also include treating a person who is not ill with the influenza or not considered at high risk for complications, in order to reduce the chances of getting infected with the influenza and passing it on to a high-risk person in close contact with him (for instance, healthcare workers, nursing home workers, etc.).

According to the United States Center for Disease Control (US CDC), an influenza "outbreak" is defined as a sudden increase of acute febrile respiratory illness (AFRI) occurring within a 48 to 72 hour period, in a group of people who are in close proximity to each other (e.g. in the same area of an assisted living facility, in the same household, etc.) over the normal background rate or when any subject in the population being analyzed tests positive for influenza. One case of confirmed influenza by any testing method is considered an outbreak.

A "cluster" is defined as a group of three or more cases of AFR1 occurring within a 48 to 72 hour period, in a group of people who are in close proximity to each other (e.g. in the same area of an assisted living facility, in the same household, etc.).

As used herein, the "index case", "primary case" or "patient zero" is the initial patient in the population sample of an epidemiological investigation. When used in general to refer to such patients in epidemiological investigations, the term is not capitalized. When the term is used to refer to a specific person in place of that person's name within a report on a specific investigation, the term is capitalized as Patient Zero. Often scientists search for the index case to determine how the disease spread and what reservoir holds the disease in between outbreaks. Note that the index case is the first patient that indicates the existence of an outbreak. Earlier cases may be found and are labeled primary, secondary, tertiary, etc.

In some embodiments, the methods of the disclosure are a preventative or "prophylactic" measure to a patient, specifically a human, having a predisposition to complications resulting from infection by an influenza virus. The term "prophylactic" as used herein as for example in prophylactic use, "prophylactically", etc., is the prophylactic use in situations in which an "index case" or an "outbreak" has been confirmed, in order to prevent the spread of infection in the rest of the community or population group.

In embodiments, the methods of the disclosure are applied as a "prophylactic" measure to members of a community or population group, specifically humans, in order to prevent the spread of infection.

As used herein, an "effective amount" refers to an amount sufficient to elicit the desired biological response. In the present disclosure the desired biological response is to inhibit the replication of influenza virus, to reduce the amount of influenza viruses or to reduce or ameliorate the severity, duration, progression, or onset of an influenza virus infection, prevent the advancement of an influenza viruses infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti-viral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, a safe and effective amount should be assumed. For example, compounds described herein can be administered to a subject in a dosage range from between approximately 0.01 to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

Dosages of the compounds for uses described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), three times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc.

Combination Therapy

The compounds described herein can be used in conjunction with other anti-influenza compounds, and in conjunction with vaccination. Combination therapy can be particularly advantageous where a patient might be exposed to more than one form of the influenza virus.

A safe and effective amount can be achieved in the method or pharmaceutical composition of the disclosure employing a compound of Formula I, or a pharmaceutically acceptable salt thereof alone or in combination with an additional suitable therapeutic agent, for example, an antiviral agent or a vaccine. When "combination therapy" is employed, a safe and effective amount can be achieved using a first amount of a compound of Formula I, or a pharmaceutically acceptable salt thereof, and a second amount of an additional suitable therapeutic agent (e.g. an antiviral agent or vaccine).

In embodiments, the compound of Formulas I, or a pharmaceutically acceptable salt, and the additional therapeutic agent, are each administered in a safe and effective amount (i.e., each in an amount which would be therapeutically effective if administered alone). In other embodiments, the compound of Formula I, or a pharmaceutically acceptable salt thereof, and the additional therapeutic agent, are each administered in an amount which alone does not provide a therapeutic effect (a sub-therapeutic dose). In yet other embodiments, the compound of Formula I, or a pharmaceutically acceptable salt thereof can be administered in a safe and effective amount, while the additional therapeutic agent is administered in a sub-therapeutic dose. In still other embodiments, the compound of Formula I, a pharmaceutically acceptable salt thereof can be administered in a sub-therapeutic dose, while the additional therapeutic agent, for example, a suitable antiviral therapeutic agent is administered in a safe and effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

In embodiments, the present disclosure is directed to methods of combination therapy for inhibiting Flu virus's replication in biological samples or patients, or for treating or preventing Influenza virus infections in patients using the compounds or pharmaceutical compositions described herein, e.g., a compound of Formula I, or a pharmaceutically acceptable salt thereof. Accordingly, pharmaceutical compositions also include those comprising a compound as disclosed herein (e.g., an inhibitor of Flu virus replication) in combination with an anti-viral compound exhibiting anti-Influenza virus activity.

Methods of use of the compounds and compositions disclosed herein also include combination of chemotherapy with a compound or composition of Formula I, or a pharmaceutically acceptable salt thereof or with a combination of a compound or composition of this disclosure with another anti-viral agent and vaccination with a Flu vaccine.

When co-administration involves the separate administration of the first amount of a compound of Formula I, or a pharmaceutically acceptable salt thereof and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I, or a pharmaceutically acceptable salt thereof and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the disclosure) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of co-administration of a first amount of a compound of Formula I, or a pharmaceutically acceptable salt thereof and a second amount of an additional therapeutic agent can result in an enhanced or synergistic therapeutic effect, wherein the combined effect is greater than the additive effect that would result from separate administration of the first amount of the compound of Formula I, or a pharmaceutically acceptable salt thereof and the second amount of the additional therapeutic agent.

As used herein, the term "synergistic" refers to a combination of a compound disclosed herein and another therapy (e.g., a prophylactic or therapeutic agent), which is more effective than the additive effects of the therapies. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

When the combination therapy using compounds as disclosed herein is in combination with a Flu vaccine, both therapeutic agents can be administered so that the period of time between each administration can be longer (e.g. days, weeks or months).

The presence of a synergistic effect can be determined using suitable methods for assessing drug interaction. Suitable methods include, for example, the Sigmoid-E max equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

Anti-Influenza Vaccines

The compounds described herein can be prophylactically administered in conjunction with anti-influenza vaccines. These vaccines can be administered, for example, via subcutaneous or intranasal administration. Vaccination via subcutaneous injection typically induces an IgG antibody having a neutralizing activity in the serum, and is highly effective for preventing progression of the condition into a more severe one such as pneumonia and the like. However, in the upper airway mucosa, which is the infection site, IgA is the main prophylactic component. Since IgA is not induced by subcutaneous administration, it can also be advantageous to administer vaccines via an intranasal route.

Antiviral Inhibitors

A variety of other compounds can be used, in combination with the compounds described herein, to treat or prevent an influenza infection. Approved compounds include neuraminidase (NA) inhibitors, ion channel (M2) inhibitors, polymerase (PB1) inhibitors, and other influenza antivirals.

There are three FDA-approved influenza antiviral drugs for use against influenza viruses, including Relenza (zanamivir), Tamiflu (oseltamivir phosphate), and Rapivab (peramivir). Older drugs, Symmetrel (amantadine) and Flumadine (rimantadine), are approved for treating and preventing influenza A.

Neuraminidase (NA) inhibitors are a class of drugs which block the neuraminidase enzyme. They are commonly used as antiviral drugs because they block the function of viral neuraminidases of the influenza virus, by preventing its reproduction by budding from the host cell. Representative neuraminidase inhibitors include Oseltamivir (Tamiflu), Zanamivir (Relenza), Laninamivir (Inavir), and Peramivir.

M2 inhibitors can also be used. The Matrix-2 (M2) protein is a proton-selective ion channel protein, integral in the viral envelope of the influenza A virus. Two different sites for drug interaction have been proposed. One is a lipid-facing pocket between 2 adjacent transmembrane helices (around Asp-44), at which the drug binds and inhibits proton conductance allosterically. The other is inside the pore (around Ser-31), at which the drug directly blocks proton passage.

The anti-influenza virus drug, amantadine, is a specific blocker of the M2 H+ channel. In the presence of amantadine, viral uncoating is incomplete, and the RNP core fails to promote infection. Aminoadamantanes, including amantadine and rimantadine have been widely abandoned due to virus resistance, but combination therapy can lessen the development of drug resistance, as virus which becomes resistant to one active agent can still be treated by the other agent(s) in the combination therapy.

Inhibitors of influenza RNA-dependent RNA polymerase (RdRp) include favipiravir and compounds described in PCT WO 2013/138236. Additional compounds, disclosed in Muratore et al., "Small molecule inhibitors of influenza A and B viruses that act by disrupting subunit interactions of the viral polymerase," PNAS, vol. 109 no. 16, 6247-6252 (April 2012), include the following:

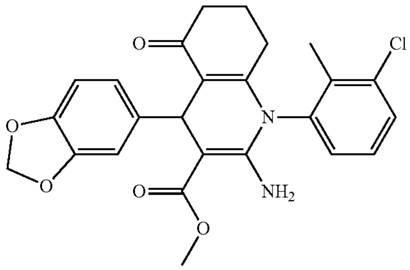

-continued

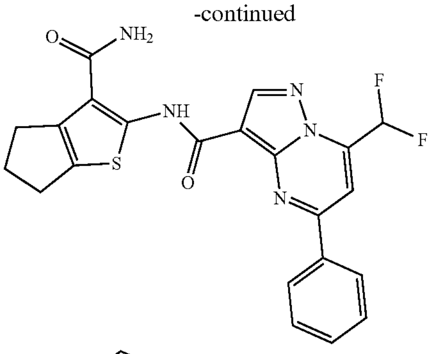

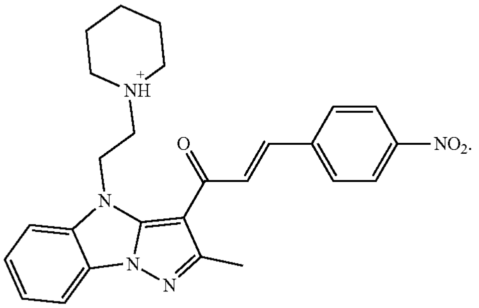

Specific examples that can be co-administered with a compound described herein include neuraminidase inhibitors, such as oseltamivir (Tamiflu®) and Zanamivir (Rlenza®), viral ion channel (M2 protein) blockers, such as amantadine (Symmetrel®) and rimantadine (Flumadine®), and antiviral drugs described in WO 2003/015798, including T-705 under development by Toyama Chemical of Japan. (See also Ruruta et al., Antiviral Research, 82: 95-102 (2009), "T-705 (flavipiravir) and related compounds: Novel broad-spectrum inhibitors of RNA viral infections.") In some embodiments, the compounds described herein can be co-administered with a traditional influenza vaccine.

III. Compound Preparation

Also provided herein are methods of preparing a compound as disclosed herein. In embodiments, the methods are directed to prepare compounds represented by Formulas I or Ia-Ih, or pharmaceutically acceptable salts thereof.

Also provided are methods of preparing a compound as disclosed herein. The compounds described herein, and pharmaceutical salts thereof, all include a common core that includes a pyridin-4(1H)-one ring.

In general, compounds of Formula (I) can be synthesized according to Scheme 1.

Scheme 1

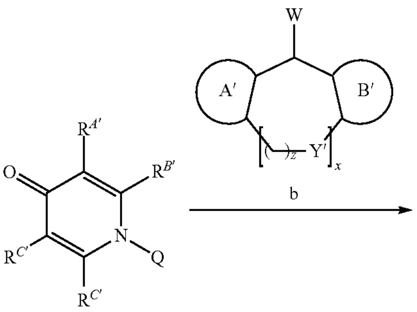

a

-continued

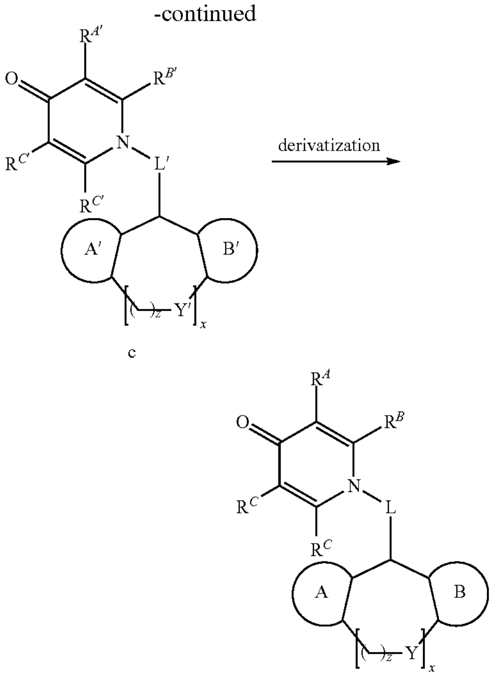

c

I

Compounds having structure I can be synthesized using the procedure shown in Scheme 1. Reaction of a 1-substituted pyridin-4-one a with an optionally substituted cyclic compound b produces compounds having structure c. It is understood that the moieties represented by Q and W are reactive to each other such that they form a linker L (or an L' as explained below) when the coupling reaction between a and b is carried out. Optional subsequent derivatization gives compounds as described herein, i.e., compounds of Formula I having structure d. Appropriate derivatization reactions can be selected based on the nature of substituents $R^{A'}$, $R^{B'}$, $R^{C'}$, rings A' and B', and linker L'. Because the derivatization is optional, each of $R^{A'}$, $R^{B'}$, $R^{C'}$, A', B', and L'. can represent an $R^A$, $R^B$, $R^C$, A, B, or L as defined above, or a precursor moiety which can undergo an appropriate derivatization reaction to produce an $R^A$, $R^B$, $R^C$, A, B, or L as defined above.

The coupling of compounds a and b can be catalyzed by appropriate reagents selected based on the precise nature of compounds a and b. For example, when moiety Q of a is an $NH_2$ group and moiety W of compound b is a hydroxyl group (i.e., an —OH), the coupling of compounds a and b can be catalyzed by e.g., propylphosphonic anhydride ($T_3P$). Occasionally, the coupling reaction may not require a catalyst, e.g., when compound b is a diacyl chloride (i.e., when each W is Cl).

Compounds a and b can be purchased commercially or prepared by a variety of methods from commercially-available starting materials. For example, pyridin-4-ones such as compounds having structure a can be prepared by the addition of an amine (e.g., pyridinium para toluene sulfonate (PPTS)-catalyzed addition of hydrazine or an organic primary amine) to a 4H-pyran-4-one formed by the cyclization of commercial acyclic precursors. Cyclic compounds having structure b can be prepared by various cyclization reactions of open-chain precursors (e.g., an acid-catalyzed cyclization), such as treatment of a phenoxyalkanoic acid with polyphosphoric acid, or treatment of an o-phenoxymethylbenzoic acid with trifluoroacetic anhydride and borontrifluoride etherate. An example of a possible synthesis of a compound b is shown in Scheme 2, below.

Scheme 2

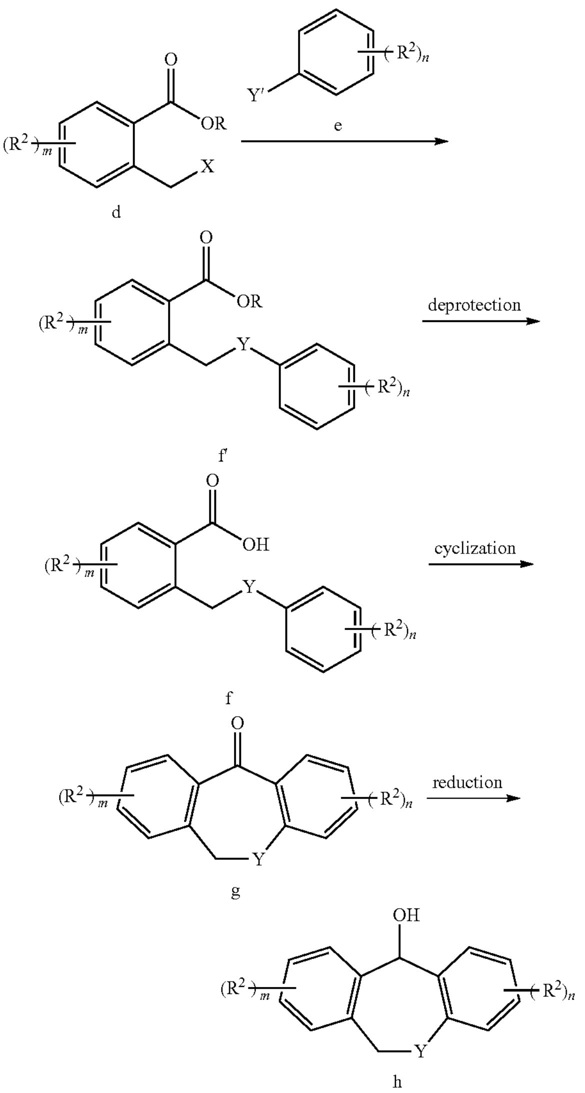

d f' f g h m, n = 0-4
X = leaving group
R = protecting group

Compounds having structure b can be synthesized as shown in Scheme 2. A benzoic acid derivative d which bears a leaving group X (e.g., a halide or pseudohalide) is reacted with a phenyl compound e which bears a nucleophilic moiety Y', which forms a Y group through reaction with the X moiety of d, and in the process forms an intermediate diaryl compound f'. For example, X can be Br and Y' can be OH, which react to form a Y group (O). The protected moiety COOR (e.g., alkyl ester) of compound f' can be deprotected (e.g., by treatment with an inorganic hydroxide) to yield compound f, and cyclized under appropriate conditions (e.g., treatment with polyphosphoric acid or trifluoroacetic anhydride and borontrifluoride etherate) to yield a fully cyclized compound g. This compound g can be a cyclic compound b as described in Scheme 1 above, or it can be subjected to further derivatization reaction such as a reduction (e.g., treatment with sodium borohydride) to produce a cyclic compound b which has a structure h. The necessity of derivatizing a compound b having structure g can be determined by considering the nature of the compound a which will be reacted with the compound b having a structure g.

Derivatization reactions to transform compounds having structure c into compounds of Formula I can be selected based on the nature of the substituents $R^{A}$', $R^{B}$', $R^{C}$', rings A' and B', and linker L' in compound c and the functionality desired in the compound of Formula I. For example, $R^{A}$' and/or L' can comprise amine or amide groups, which can be alkylated (e.g., via treatment with an alkyl or benzyl halide) to alkylamino groups, which can be further derivatized by methods known in the art to form a variety of functional groups. Alternately, $R^{A}$', $R^{B}$', and/or $R^{C}$', can be carboxylic acid groups, which can be converted to ester or amide groups through appropriate reactions. Derivatization of carboxylic acid groups can be effected via known methods such as carbodiimide chemistry, or through the use of catalytic reagents such as HATU and the like, according to the nature of the derivatization reaction as disclosed herein.

The variables in these formulae are either the same as the definitions provided in the section defining the compounds described herein, or, where the functional groups defined by the variables would be labile under the reaction conditions described herein, can be either protected forms of the functional groups, or synthons for such groups. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference.

Any suitable reaction condition known in the art, for example, in PCT WO 2005/095400 and PCT WO 2007/084557 for the coupling of a dioxaboraolan with a chlorodiazaindole can be employed. For example, the reaction between these precursors can be performed in the presence of $Pd(PPh_3)_4$. Specific exemplary conditions are described in the working examples in the Examples section of the instant application.

In some embodiments of the chemistry described herein, the leaving group is a tosylate group, and the tosylate group is "de-tosylated" to generate the compounds of Formulas I, II or III after the coupling chemistry is completed. Any suitable condition for deprotecting a Ts group known in the art can be employed in the disclosure. Specific exemplary conditions are described in working examples. De-tosylation can generate the compounds of Formulas I, II or III where L is —H. If desired, this position can be alkylated by any suitable method known in the art to form the compounds of Formula I, II, or III where L is, for example, the moieties in ii), iii), iv), or v). Specific exemplary synthetic methods are described in more detail below in the working examples.

Chiral Separations

The compounds described herein can have asymmetric centers and occur as racemates, racemic mixtures, individual diastereomers or enantiomers, with all isomeric forms being included in the present disclosure. Compounds of the present disclosure having a chiral center can exist in and be isolated in optically active and racemic forms. Some compounds can exhibit polymorphism. The present disclosure encompasses racemic, optically-active, polymorphic, or stereoisomeric forms, or mixtures thereof, of a compound of the disclosure, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Pharmaceutical Compositions

The compounds described herein can be formulated into pharmaceutical compositions that further comprise a pharmaceutically acceptable carrier, diluent, adjuvant or vehicle. In embodiments, the present disclosure relates to a pharmaceutical composition comprising a compound described above or salt thereof, and a pharmaceutically acceptable carrier, diluent, adjuvant or vehicle. In embodiments, the pharmaceutical composition comprises a safe and effective amount of a compound as disclosed herein or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount". The term "therapeutically effective amount" refers to an amount effective in treating and/or ameliorating an influenza virus infection in a patient. The term "prophylactically effective amount" refers to an amount effective in preventing and/or substantially lessening the chances or the size of influenza virus infection outbreak.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this disclosure. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Formulations for Pulmonary Delivery

In some embodiments, the pharmaceutical compositions disclosed herein are adapted to be administered to the lower respiratory tract (e.g., the lungs) directly through the airways by inhalation. Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose or starch. Inhalable dry powder compositions may be presented in capsules and cartridges of gelatin or a like material, or blisters of laminated aluminum foil for use in an inhaler or insufflators. Each capsule or cartridge may generally contain e.g., from about 10 mg to about 100 g of each active compound. Alternatively, the composition may be presented without excipients.

The inhalable compositions may be packaged for unit dose or multi-dose delivery. For example, the compositions can be packaged for multi-dose delivery in a manner analogous to that described in GB 2242134, U.S. Pat. Nos. 6,632,666, 5,860,419, 5,873,360, and 5,590,645 (all illustrating the "Diskus" device), or GB2i78965, GB2129691, GB2169265, U.S. Pat. Nos. 4,778,054, 4,811,731 and 5,035,237 (which illustrate the "Diskhaler" device), or EP 69715 ("Turbuhaler" device), or GB 2064336 and U.S. Pat. No. 4,353,656 ("Rotahaler" device).

Spray compositions for topical delivery to the lung by inhalation may be formulated as aqueous solutions or suspensions or as aerosols delivered from pressurized packs, such as a metered dose inhaler (MDI), with the use of a suitable liquefied propellant, including hydrofluoroalkanes such as dichlorodifluoromethane, trichlorofluoromethane, dichlorotetrafluoroethane, and especially 1,1,1,2-tetrafluoroethane, 1,1,1,2,3,3,3-heptafluoro-n-propane and mixtures thereof. Aerosol compositions suitable for inhalation can be presented either as suspensions or as solutions.

Medicaments for administration by inhalation typically have a controlled particle size. The optimum particle size for inhalation into the bronchial system is usually about 1 to about 10 μm, and in some embodiments, from about 2 to about 5 μm. Particles having a size above about 20 μm are generally too large when inhaled to reach the small airways. To achieve these particle sizes the particles of the active ingredient may be subjected to a size reducing process such as micronization. The desired size fraction may be separated out by air classification or sieving. Preferably, the particles will be crystalline.

Intranasal sprays may be formulated with aqueous or non-aqueous vehicles with the addition of agents such as thickening agents, buffer salts or acid or alkali to adjust the pH, isotonic adjusting agents or anti-oxidants.

Solutions for inhalation by nebulization may be formulated with an aqueous vehicle with the addition of agents such as acid or alkali, buffer salts, isotonic adjusting agents or antimicrobial agents. They may be sterilized by filtration or heating in an autoclave, or presented as a non-sterile product. Nebulizers supply the aerosol as a mist created from an aqueous formulation.

In some embodiments, the pharmaceutical compositions disclosed herein can be formulated with supplementary active ingredients.

In some embodiments, the pharmaceutical composition disclosed herein is administered from a dry powder inhaler. In other embodiments, the pharmaceutical composition disclosed herein is administered by an aerosol dispensing device, optionally in conjunction with an inhalation chamber such as the "Volumatic" @ inhalation chamber.

The carrier can be a solvent or dispersion medium containing, for example, water, ethanol, polyol (for example, glycerol, propylene glycol and liquid polyethylene glycol, and the like), suitable mixtures thereof, and/or vegetable oils. The proper fluidity can be maintained, for example, by the use of a coating such as, for example, lecithin, by the maintenance of the required particle size in the case of dispersion and by the use of surfactants. Preventing the action of microorganisms in the compositions disclosed herein is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments, a pharmaceutical composition can be within a matrix which controls the release of the composition. In some embodiments, the matrix can comprise lipid, polyvinyl alcohol, polyvinyl acetate, polycaprolactone, poly(glycolic)acid, poly(lactic)acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and combinations thereof and other polymers such as those disclosed, for example, in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety. In these embodiments, the matrix sustainedly releases the drug.

Pharmaceutically acceptable carriers and/or diluents may also include any solvents, dispersion media, coatings, antibacterials and/or antifungals, isotonic and absorption delaying agents and the like. The use of such media and agents for pharmaceutically active substances is well known in the art. Except insofar as any conventional medium or agent is incompatible with the active ingredient, use thereof in the pharmaceutical compositions is contemplated.

The pharmaceutical compositions can be formulated for administration in accordance with conventional techniques. See, e.g., Remington, The Science and Practice of Pharmacy (20th Ed. 2000). For example, the intranasal pharmaceutical compositions of the present disclosure can be formulated as an aerosol (this term includes both liquid and dry powder aerosols). Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles (e.g., lyophilized, freeze dried, etc.) can likewise be produced with any solid particulate medicament aerosol generator, by techniques known in the pharmaceutical art. As another example, the pharmaceutical compositions can be formulated as an on-demand dissolvable form, which provides a lyophilized portion of the pharmaceutical composition and a dissolving solution portion of the pharmaceutical composition.

In some embodiments, the pharmaceutical composition is in the form of an aqueous suspension, which can be prepared from solutions or suspensions. With respect to solutions or suspensions, dosage forms can be comprised of micelles of lipophilic substances, liposomes (phospholipid vesicles/membranes) and/or a fatty acid (e.g., palmitic acid). In particular embodiments, the pharmaceutical composition is a solution or suspension that is capable of dissolving in the fluid secreted by mucous membranes of the epithelium of the tissue to which it is administered, applied and/or delivered, which can advantageously enhance absorption.

The pharmaceutical composition can be an aqueous solution, a nonaqueous solution or a combination of an aqueous and nonaqueous solution. Suitable aqueous solutions include, but are not limited to, aqueous gels, aqueous suspensions, aqueous microsphere suspensions, aqueous microsphere dispersions, aqueous liposomal dispersions, aqueous micelles of liposomes, aqueous microemulsions, and any combination of the foregoing, or any other aqueous solution that can dissolve in the fluid secreted by the mucosal membranes of the nasal cavity. Exemplary non-aqueous solutions include, but are not limited to, nonaqueous gels, nonaqueous suspensions, nonaqueous microsphere suspensions, nonaqueous microsphere dispersions, non-aqueous liposomal dispersions, nonaqueous emulsions, non-aqueous microemulsions, and any combination of the foregoing, or any other nonaqueous solution that can dissolve or mix in the fluid secreted by mucosal membranes.

Examples of powder formulations include, without limitation, simple powder mixtures, micronized powders, freeze dried powder, lyophilized powder, powder microspheres, coated powder microspheres, liposomal dispersions, and any combination of the foregoing. Powder microspheres can be formed from various polysaccharides and celluloses, which include without limitation starch, methylcellulose, xanthan gum, carboxymethylcellulose, hydroxypropyl cellulose, carbomer, alginate polyvinyl alcohol, acacia, chitosans, and any combination thereof.

In particular embodiments, the composition is one that is at least partially, or even substantially (e.g., at least 80%, 90%, 95% or more) soluble in the fluids that are secreted by mucosa so as to facilitate absorption. Alternatively or additionally, the composition can be formulated with a carrier and/or other substances that foster dissolution of the agent within secretions, including without limitation fatty acids (e.g., palmitic acid), gangliosides (e.g., GM-1), phospholipids (e.g., phosphatidylserine), and emulsifiers (e.g., polysorbate 80).

Those skilled in the art will appreciate that for intranasal administration or delivery, because the volume of the pharmaceutical composition administered is generally small, nasal secretions may alter the pH of the administered dose since the range of pH in the nasal cavity can be as wide as 5 to 8. Such alterations can affect the concentration of un-ionized drug available for absorption. Accordingly, in representative embodiments, the pharmaceutical composition further comprises a buffer to maintain or regulate pH in situ. Typical buffers include, but are not limited to, ascorbate, acetate, citrate, prolamine, carbonate, and phosphate buffers.

In embodiments, the pH of the pharmaceutical composition is selected so that the internal environment of the mucosal tissue after administration is on the acidic to neutral side, which (1) can provide the active compound in an un-ionized form for absorption, (2) prevents growth of pathogenic bacteria, which is more likely to occur in an alkaline environment, and (3) reduces the likelihood of irritation of the mucosa.

For liquid and powder sprays or aerosols, the pharmaceutical composition can be formulated to have any suitable and desired particle or droplet size. In illustrative embodiments, the majority and/or the mean size of the particles or droplets range from equal to or greater than about 1, 2.5, 5, 10, 15 or 20 microns and/or equal to or less than about 25, 30, 40, 45, 50, 60, 75, 100, 125, 150, 175, 200, 225, 250, 275, 300, 325, 350, 375, 400, or 425 microns (including all combinations of the foregoing). Representative examples of suitable ranges for the majority and/or mean particle or droplet size include, without limitation, from about 5 to 100 microns, from about 10 to 60 microns, from about 175 to 325 microns, and from about 220 to 300 microns which facilitate the deposition of a safe and effective amount of the active compound, for example, in the nasal cavity (e.g., in the upper third of the nasal cavity, the superior meatus, the olfactory region and/or the sinus region to target the olfactory neural pathway). In general, particles or droplets smaller than about 5 microns will be deposited in the trachea or even the lung, whereas particles or droplets that are about 50 microns or larger generally do not reach the nasal cavity and are deposited in the anterior nose.

International patent publication WO 2005/023335 (Kurve Technology, Inc.) describes particles and droplets having a diameter size suitable for the practice of representative embodiments of pharmaceutical compositions disclosed herein. In particular embodiments, the particles or droplets have a mean diameter of about 5 to 30 microns, about 10 to 20 microns, about 10 to 17 microns, about 10 to 15 microns, about 12 to 17 microns, about 10 to 15 microns or about 10 to 12 microns. The particles can "substantially" have a mean diameter or size as described herein, i.e., at least about 50%, 60%, 70%, 80%, 90% or 95 or more of the particles are of the indicated diameter or size range.

The pharmaceutical composition can be delivered as a nebulized or atomized liquid having a droplet size as described above.

According to particular embodiments of this disclosure that comprise methods of intranasal delivery, it can be desirable to prolong the residence time of the pharmaceutical composition in the nasal cavity (e.g., in the upper third of the nasal cavity, the superior meatus, the olfactory region and/or in the sinus region), for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl), which are agents that enhance residence time in the nasal cavity. As a further approach, increasing the viscosity of the formulation can also provide a means of prolonging contact of the agent with the nasal epithelium. The pharmaceutical composition can be formulated as a nasal emulsion, ointment or gel, which offers advantages for local application because of their viscosity.

Moist and highly vascularized membranes can facilitate rapid absorption; consequently, the pharmaceutical composition can optionally comprise a humectant, particularly in the case of a gel-based composition so as to assure adequate intranasal moisture content. Examples of suitable humectants include but are not limited to glycerin or glycerol, mineral oil, vegetable oil, membrane conditioners, soothing agents, and/or sugar alcohols (e.g., xylitol, sorbitol; and/or mannitol). The concentration of the humectant in the pharmaceutical composition will vary depending upon the agent selected and the formulation.

The pharmaceutical composition can also optionally include an absorption enhancer, such as an agent that inhibits enzyme activity, reduces mucous viscosity or elasticity, decreases mucociliary clearance effects, opens tight junctions, and/or solubilizes the active compound. Chemical enhancers are known in the art and include chelating agents (e.g., EDTA), fatty acids, bile acid salts, surfactants, and/or preservatives. Enhancers for penetration can be particularly useful when formulating compounds that exhibit poor membrane permeability, lack of lipophilicity, and/or are degraded by aminopeptidases. The concentration of the absorption enhancer in the pharmaceutical composition will vary depending upon the agent selected and the formulation.

To extend shelf life, preservatives can optionally be added to the pharmaceutical composition. Suitable preservatives include but are not limited to benzyl alcohol, parabens, thimerosal, chlorobutanol and benzalkonium chloride, and combinations of the foregoing. The concentration of the preservative will vary depending upon the preservative used, the compound being formulated, the formulation, and the like. In representative embodiments, the preservative is present in an amount of about 2% by weight or less.

The pharmaceutical compositions described herein can optionally contain an odorant, e.g., as described in EP 0 504 263 B1, to provide a sensation of odor, to aid in inhalation of the composition so as to promote delivery to the olfactory region and/or to trigger transport by the olfactory neurons.

As another option, the composition can comprise a flavoring agent, e.g., to enhance the taste and/or acceptability of the composition to the subject.

Porous Particles for Pulmonary Administration

In some embodiments, the particles are porous, so that they have an appropriate density to avoid deposition in the back of the throat when administered via an inhaler. The combination of relatively large particle size and relatively low density avoids phagocytosis in the lungs, provides appropriately targeted delivery, avoids systemic delivery of the components, and provides a high concentration of the components in the lung.

Representative methods for preparing such particles, and for delivering such particles, are described, for example, in U.S. Pat. No. 7,384,649, entitled, "Particulate compositions for pulmonary delivery," U.S. Pat. No. 7,182,961, entitled "Particulate compositions for pulmonary delivery," U.S. Pat. No. 7,146,978, entitled, "Inhalation device and method," U.S. Pat. No. 7,048,908, entitled "Particles for inhalation having sustained release properties," U.S. Pat. No. 6,956,021, entitled "Stable spray-dried protein formulations," U.S. Pat. No. 6,766,799, entitled "Inhalation device," and U.S. Pat. No. 6,732,732, entitled "Inhalation device and method."

Additional patents disclosing such particles include U.S. Pat. No. 7,279,182, entitled "Formulation for spray-drying large porous particles," U.S. Pat. No. 7,252,840, entitled "Use of simple amino acids to form porous particles," U.S. Pat. No. 7,032,593, entitled "Inhalation device and method," U.S. Pat. No. 7,008,644, entitled "Method and apparatus for producing dry particles," U.S. Pat. No. 6,848,197, entitled "Control of process humidity to produce large, porous particles," and U.S. Pat. No. 6,749,835, entitled "Formulation for spray-drying large porous particles."

U.S. Pat. No. 7,678,364, entitled "Particles for inhalation having sustained release properties," discloses methods for delivering particles to the pulmonary system comprising: administering to the respiratory tract of a patient in need of treatment, prophylaxis or diagnosis a safe and effective amount of a dry powder comprising: a) a multivalent metal cation which is complexed with a therapeutic, prophylactic or diagnostic agent; b) a pharmaceutically acceptable carrier; and c) a multivalent metal cation-containing component wherein the dry powder is spray-dried and has a total amount of multivalent metal cation which is about 10% w/w or more of the total weight of the agent, a tap density of about 0.4 $g/cm^3$ or less, a median geometric diameter of from about 5 micrometers to about 30 micrometers and an aerodynamic diameter of from about 1 to about 5 microns.

The amount of the compounds described herein, or salts thereof, present in the particles can range from about 0.1 weight % to about 95 weight %, though in some cases, can even be as high as 100%. For example, from about 1 to about 50%, such as from about 5 to about 30%. Particles in which the compound is distributed throughout a particle can be preferred.

In some embodiments, the particles include a surfactant other than the phospholipids described above. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to particles, they tend to present moieties to the external environment that do not attract similarly-coated particles, thus reducing particle agglomeration. Surfactants may also promote absorption of a therapeutic or diagnostic agent and increase bioavailability of the agent.

Suitable surfactants which can be employed in fabricating the particles disclosed herein include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxamer; a sorbitan fatty acid ester such as sorbitan trioleate (Span 85); Tween® 80 and tyloxapol.

The surfactant can be present in the particles in an amount ranging from about 0 to about 5 weight %. Preferably, it can be present in the particles in an amount ranging from about 0.1 to about 1.0 weight %.

Particles that have a tap density less than about 0.4 $g/cm^3$, median diameters of at least about 5 μm, and an aerodynamic diameter of from about 1 μm to about 5 μm, or from about 1 μm to about 3 μm, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

Liposomal Delivery

The compositions described herein are advantageously delivered to the lungs, so as to provide the compounds at the site of an actual or potential influenza infection. This can be accomplished by pulmonary delivery via metered-dose inhalers or other pulmonary delivery devices, and also by lodging particles in the capillary beds surrounding the alveoli in the lungs.

Nanocarriers, such as liposomes, including small unilamellar vesicles, show several advantages over other conventional approaches for delivering drugs to the lungs, including prolonged drug release and cell-specific targeted drug delivery. Nano-sized drug carriers can also be advantageous for delivering poorly water soluble drugs, and certain of the compounds described herein are poorly water-soluble. Additional advantages include their ability to provide controlled release, protection from metabolism and degradation, decreased drug toxicity and targeting capabilities.

The liposomes (preferably unilamellar vesicles) have a size less than 200 nm as measured by dynamic light scattering, and preferably characterized by being comprised of chemically pure synthetic phospholipids, most preferably having aliphatic side chains of a length of at least 16 carbons, and containing one or more of the compounds described herein, or a pharmaceutically acceptable salt thereof, sufficient to preferentially deliver (i.e., target) a quantity of the compounds thereof to the capillary beds surrounding the alveoli. Vesicle diameter can be measured, for example, by dynamic light scattering using a heliumneon 100 mW NEC gas laser and a Malvern K7027 correlator, ideally with at least two or three measurements made for each for each size determination.

The expression "chemically pure phospholipids" is meant to define phospholipids which are essentially free of deleterious detergent moieties and impurities which cause aggregation of small unilamellar vesicles (SUVs) formed therefrom, and which are more than 97% pure. Preferably, the liposomes have a diameter predominantly of from about 50 to about 160 nm, are essentially neutral in charge, and incorporate phospholipids having a side chain length of from 16 to 18 carbon atoms. More preferably, the liposomes are prepared from distearoyl phosphatidylcholine (DSPC) and include cholesterol (most preferably in an amount of from 10 to 50% of total lipid) as a vesicle stabilizer.

It can also be advantageous that the liposomes have a melting point above body temperature (i.e., above 37° C.). For this reason, it can be advantageous to use pure phospholipids, preferably ones that are saturated, and have a carbon chain length of at least 16 carbons, preferably between 16 and 18 carbons. Distearoylphosphatidyl choline (DSPC) is a preferred phospholipid.

Cholesterol helps to stabilize the liposomes, and is preferably added in a sufficient amount to provide liposome stability. Most preferably, the liposomes further comprise a pegylated phospholipid, such as DSPEPEG. The method involves introducing into a patient's bloodstream an amount of liposomes, of a size of less than 200 nm (preferably unilamellar vesicles) and preferably characterized by being comprised of chemically pure synthetic phospholipids, most preferably having aliphatic side chains of a length of at least 16 carbons, and containing the compounds described herein, or a pharmaceutically acceptable salt or prodrug thereof, sufficient to preferentially deliver (i.e., target) a quantity of the compounds to the capillary beds in the lungs, surrounding the alveoli.

The compounds described herein can be combined with other anti-influenza agents, as also described herein. Such additional agents can also be present in the liposomes, can be present in different liposomes, or can be co-administered via a different route.

The liposomes include one or more of the compounds described herein, or a pharmaceutically acceptable salt thereof, and can optionally include other anti-influenza agents. The liposomes can be prepared by dissolving the phospholipid and cholesterol in an appropriate organic solvent, such as chloroform, and evaporating the solvent to form a lipid film. If an ionophore is employed to load the compounds described herein into the liposomes, the ionophore may be added to the lipid solution before evaporation. The dried lipid film is then rehydrated in an appropriate aqueous phase, such as phosphate-buffered saline or other physiologically appropriate solution. Water-soluble drugs or therapeutic agents may be contained in the hydrating solution, although if remote loading is desired a loading agent such as a chelating agent described above may be added to the hydrating solution to be encapsulated within the inner aqueous space of the liposome.

Upon the addition of the hydrating solution, liposomes of varying size spontaneously form and encapsulate a portion of the aqueous phase. Thereafter, the liposomes and suspending aqueous solution are subjected to a shear force such as extrusion, sonication, or processing through a homogenizer according to the method described in U.S. Pat. No. 4,753,788; to produce vesicles within the specified size.

The liposomes can then be processed to remove undesirable compounds from the suspending solution, for example, un-encapsulated drug, which may be accomplished through processes such as gel chromatography or ultrafiltration.

The use of liposomes in dry powder aerosols for targeted lung delivery is described, for example, in Willis et al., *Lung*, June 2012, 190(3):251-262. One advantage is that the phospholipids used to prepare the liposomes are similar to endogenous lung surfactant.

Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, to the pulmonary system, such as by using an inhaler, such as a metered dose inhaler (MDI), or the like, depending on the severity of the infection being treated. In some embodiments, the compound or composition disclosed herein is administered orally, via inhalation, or intravenously.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. In some cases, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the disclosure can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

The present disclosure will be better understood with reference to the following non-limiting examples.

EXAMPLES

Example 1—Synthesis of Compound 2

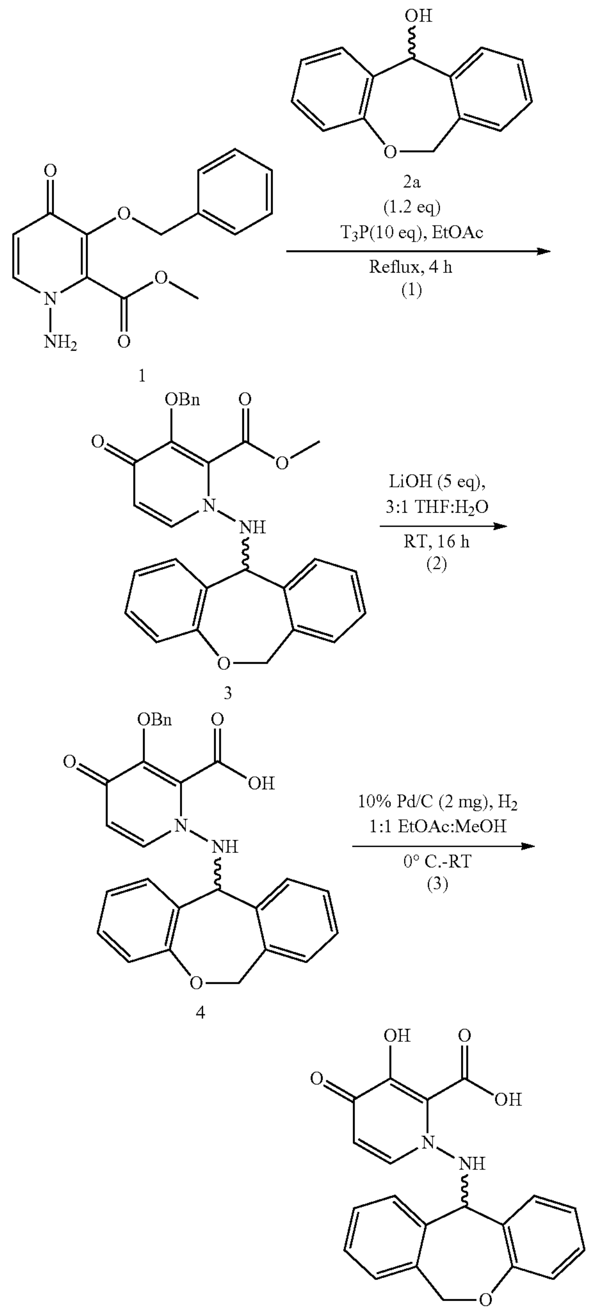

Compound 2

Synthesis of methyl 3-(benzyloxy)-1-((10,11-dihydrodibenzo[b,f]oxepin-10-yl)amino)-4-oxo-1,4-dihydropyridine-2-carboxylate (3): To a stirred solution of methyl 1-amino-3-(benzyloxy)-4-oxo-1,4-dihydropyridine-2-carboxylate (1) (1 g, 3.6 mmol) in EtOAc (25 mL) was added 10,11-dihydrodibenzo[b,f]oxepin-10-ol (2) (928 mg, 4.3 mmol) and 50% $T_3P$ in EtOAc (11.6 mL, 3.6 mmol) at RT. The reaction mixture was stirred at reflux for 3 h. After consumption of starting material (absence of compd-2 by TLC), the reaction mixture was diluted with ice cold water (100 mL) and extracted with EtOAc (3×50 mL). The combined organic layer was washed with brine solution (50 mL), dried over sodium sulfate and concentrated to get methyl 3-(benzyloxy)-1-((10,11-dihydrodibenzo[b,f]oxepin-10-yl)amino)-4-oxo-1,4-dihydropyridine-2-carboxylate.

(3). Synthesis of 3-(benzyloxy)-1-((10,11-dihydrodibenzo[b,f]oxepin-10-yl)amino)-4-oxo-1,4-dihydropyridine-2-carboxylic acid (4): To a stirred solution of methyl 3-(benzyloxy)-1-((10,11-dihydrodibenzo[b,f]oxepin-10-yl)amino)-4-oxo-1,4-dihydropyridine-2-carboxylate (3) (250 mg, 0.5 mmol) in a mixture of THF:$H_2O$ (3:1) 4 mL was added lithium hydroxide (0.038 g, 1.6 mmol) at RT for 6 h. The reaction mixture was concentrated to remove organic volatiles, acidified with sat.$NaHSO_4$ solution to get solid. Solid was collected by filtration to afford 3-(benzyloxy)-1-((10,11-dihydrodibenzo[b,f]oxepin-10-yl)amino)-4-oxo-1,4-dihydropyridine-2-carboxylic acid (4).

Synthesis of 1-((6,11-dihydrodibenzo[b,e]oxepin-11-yl)amino)-3-hydroxy-4-oxo-1,4-dihydropyridine-2-carboxylic acid (compound 2): To a stirred solution of 3-(benzyloxy)-1-((10,11-dihydrodibenzo[b,f]oxepin-10-yl)amino)-4-oxo-1,4-dihydropyridine-2-carboxylic acid (4) (50 mg, 0.11 mmol) in 1:1 EtOAc:MeOH (6 mL) was added 10% Pd/C (5 mg) and applied H2 balloon pressure for 1 h. Reaction mixture was filtered through celite bed and washed with Methanol. Filtrate was evaporated under reduced pressure and crude residue was purified by prep-HPLC purification to afford the title compound. LCMS (ESI): m/z 365.16 $(M+H)^+$ Compound s 40, 66, 73, 74, and 75 were prepared in the same manner as compound 2.

Compound 40: LCMS (ESI): m/z 415.14 $(M-H)^-$

Compound 66: LCMS (ESI): m/z 383.29 $(M+H)^+$

Compound 73: LCMS (ESI): m/z 408.30 $(M+H)^+$

Compound 74: LCMS (ESI): m/z 396.35 $(M+H)^+$

Compound 75: LCMS (ESI): m/z 401.43 $(M+H)^+$

Example 2: Synthesis of Compound 13

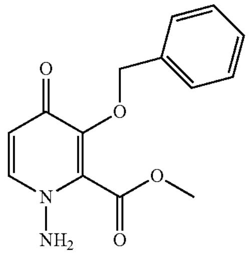

1

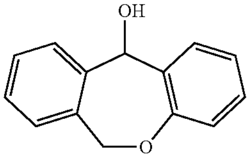

1a

50% $T_3P$ in ethylaceteate (1.2 eq)

Ethylacetete, 110° C., 2 h (Step-1)

-continued

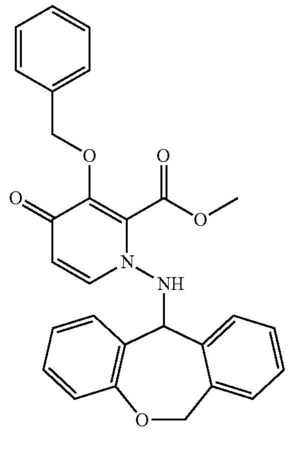

2

LiOH, THF:$H_2O$ (3:1), 0° C.-RT, 3 h, 64%

(Step-2)

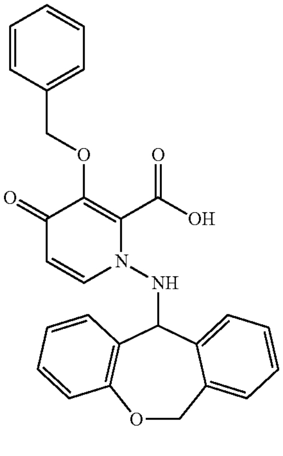

3

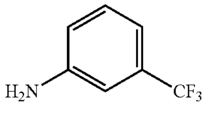

4

HATU, DIPEA, DMF,

0° C.-RT, 2 h, 54%

(Step-3)

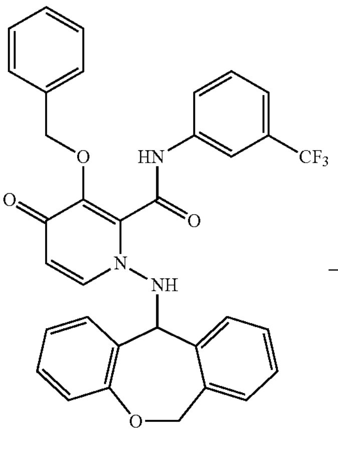

5

10% Pd/C/$H_2$ atm,

MeOH:EtOAc (2:1), RT, 6 h

Step-4

-continued

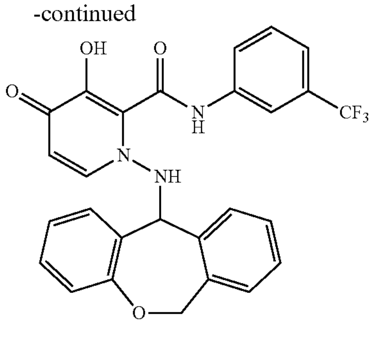

Compound 13

Synthesis of methyl 3-(benzyloxy)-1-((6,11-dihydrodibenzo[b,e]oxepin-11-yl)amino)-4-oxo-1,4-dihydropyridine-2-carboxylate (2): To a stirred solution of methyl 1-amino-3-(benzyloxy)-4-oxo-1,4-dihydropyridine-2-carboxylate 1 (5 g, 18.2481 mmol) in ethyl acetate (50 mL) was added 6,11-dihydrodibenzo[b,e]oxepin-11-ol (1a) (4.64 g, 21.8978 mmol) and 50% T3P in ethyl acetate (29 g, 91.2408 mmol) at room temperature. Stirred the reaction mixture at 110° C. for 2 h. To the reaction mixture was added water (2×50 mL) and extracted with ethyl acetate (2×200 mL). Combined organic layers were washed with brine solution (50 mL) and dried over $Na_2SO_4$, evaporated under reduced pressure to afford methyl 3-(benzyloxy)-1-((6,11-dihydrodibenzo[b,e]oxepin-11-yl)amino)-4-oxo-1,4-dihydropyridine-2-carboxylate (2)

Synthesis of 3-(benzyloxy)-1-((6,11-dihydrodibenzo[b,e]oxepin-11-yl)amino)-4-oxo-1,4-dihydropyridine-2-carboxylic acid) (3): To a stirred solution of methyl 3-(benzyloxy)-1-((6,11-dihydrodibenzo[b,e]oxepin-11-yl)amino)-4-oxo-1,4-dihydropyridine-2-carboxylate (2) (700 mg, 1.49 mmol) in a mixture of THF:$H_2O$ (3:1) 15 mL was added lithium hydroxide (107 mg, 4.48 mmol) at RT for 3 h. The reaction mixture was concentrated to remove organic volatiles, acidified with sat.$NaHSO_4$ solution till the solid precipitated out. Solid was collected by filtration to afford 3-(benzyloxy)-1-((6,11-dihydrodibenzo[b,e]oxepin-11-yl)amino)-4-oxo-1,4-dihydropyridine-2-carboxylic acid (3)

Synthesis of 3-(benzyloxy)-1-((6,11-dihydrodibenzo[b,e]oxepin-11-yl)amino)-4-oxo-N-(3-(trifluoromethyl)phenyl)-1,4-dihydropyridine-2-carboxamide (4): To a stirred solution of 3-(benzyloxy)-1-((6,11-dihydrodibenzo[b,e]oxepin-11-yl)amino)-4-oxo-1,4-dihydropyridine-2-carboxylic acid (3) (150 mg, 0.33 mmol) in DMF (5 mL) was added DIPEA (0.2 mL, 0.99 mmol) and HATU (188 mg, 0.49 mmol) at 0° C. and 3-(trifluoromethyl)aniline (4) (80 mg, 0.49 mmol) was added to the reaction mixture and stirred at RT for 16 h. After consumption of starting material, the reaction mixture was poured in ice water and filtered the precipitated solid. It was further dried under vacuum to afford 3-(benzyloxy)-1-((6,11-dihydrodibenzo[b,e]oxepin-11-yl)amino)-4-oxo-N-(3-(trifluoromethyl)phenyl)-1,4-dihydropyridine-2-carboxamide (5)

Synthesis of 1-((6,11-dihydrodibenzo[b,e]oxepin-11-yl)amino)-3-hydroxy-4-oxo-N-(3-(trifluoromethyl)phenyl)-1,4-dihydropyridine-2-carboxamide (compound 13): To a stirred solution of 3-(benzyloxy)-1-((6,11-dihydrodibenzo[b,e]oxepin-11-yl)amino)-4-oxo-N-(3-(trifluoromethyl)phenyl)-1,4-dihydropyridine-2-carboxamide (5) (60 mg, 0.10 mmol) in 1:1 EtOAc:MeOH (2 mL) was added 10% Pd/C (50 mg) at room temperature and stirred under hydrogen atmosphere at 50 psi for 3 h. The reaction mixture was filtered through celite, the filtrate was concentrated under reduced pressure to get crude compound. crude was purified by Grace reverse phase purification to afford the title compound. LCMS (ESI): m/z 508.17 $(M+H)^+$ Compounds 19, 20, 21, 24, 30, 31, 36, and 37 were prepared in the same manner as compound 13.

Compound 19: LCMS (ESI): m/z 456.28 $(M+H)^+$

Compound 20: LCMS (ESI): m/z 456.28 $(M+1)^+$

Compound 21: LCMS (ESI): m/z 490.30 $(M+H)^+$

Compound 24: LCMS (ESI): m/z 504.33 $(M+H)^+$

Compound 30: LCMS (ESI): m/z 516.15 $(M+H)^+$

Compound 31: LCMS (ESI): m/z 522.12 $(M+H)^+$

Compound 36: LCMS (ESI): m/z 516.25 $(M+H)^+$

Compound 37: LCMS (ESI): m/z 522.36 $(M+H)^+$

Example 3: Synthesis of Compound 14

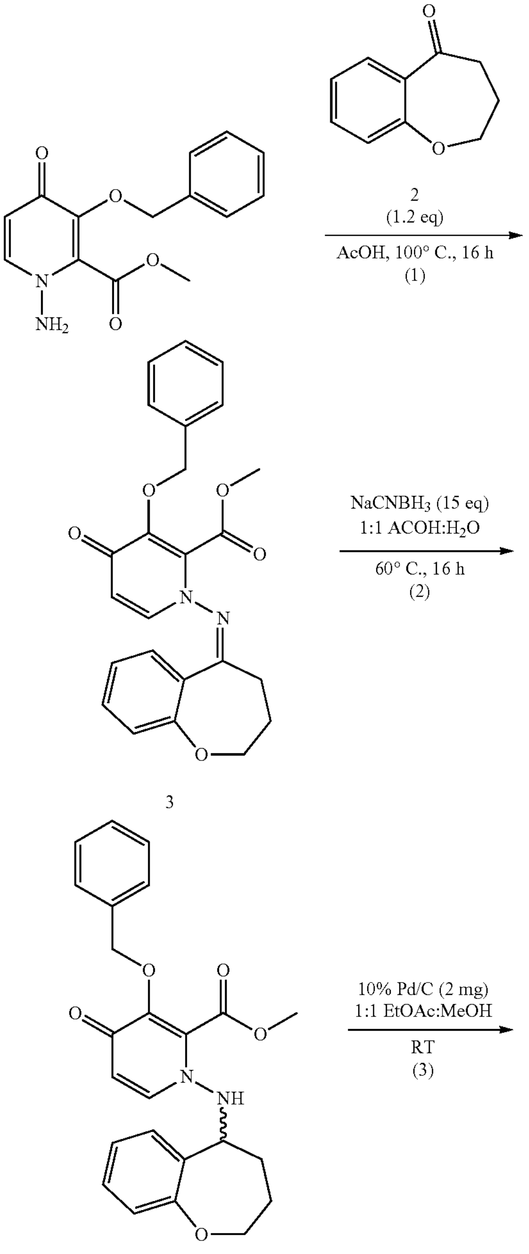

-continued

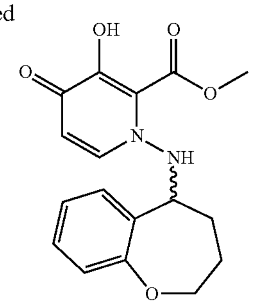

14

Synthesis of (Z)-methyl 3-(benzyloxy)-1-((3,4-dihydrobenzo[b]oxepin-5(2H)-ylidene)amino)-4-oxo-1,4-dihydropyridine-2-carboxylate (3): Methyl 1-amino-3-(benzyloxy)-4-oxo-1,4-dihydropyridine-2-carboxylate 1 (2.0 g, 7.0 mmol) and 3,4-dihydrobenzo[b]oxepin-5(2H)-one in AcOH were heated to 1000° C. for 16 h. Reaction mixture was evaporated under reduced pressure to afford (Z)-methyl 3-(benzyloxy)-1-((3, 4-dihydrobenzo[b]oxepin-5(2H)-ylidene) amino)-4-oxo-1,4-dihydropyridine-2-carboxylate (3)

Synthesis of methyl 3-(benzyloxy)-4-oxo-1-((2,3,4,5-tetrahydrobenzo[b]oxepin-5-yl)amino)-1,4-dihydropyridine-2-carboxylate: To a stirred solution of (Z)-methyl 3-(benzyloxy)-1-((3,4-dihydrobenzo[b]oxepin-5(2H)-ylidene) amino)-4-oxo-1,4-dihydropyridine-2-carboxylate (3.5 g, 8.0 mmol) in 1:1 AcOH:$H_2O$ (20 vol.) was added sodium borohydride (6.3 g, 100 mmol) at RT. Reaction mixture was stirred at 70° C. for 16 h. The reaction mixture was poured in to water (200 mL) and extracted with ethyl acetate (2×150 ml). Organic layer was washed with brine solution (100 mL), dried over anhydrous sodium sulfate and concentrated under reduced pressure to get the crude residue. Crude compound was purified through Grace reverse phase purification to afford methyl 3-(benzyloxy)-4-oxo-1-((2,3,4,5-tetrahydrobenzo[b]oxepin-5-yl)amino)-1,4-dihydropyridine-2-carboxylate

Synthesis of methyl 3-hydroxy-4-oxo-1-((2,3,4,5-tetrahydrobenzo[b]oxepin-5-yl)amino)-1,4-dihydropyridine-2-carboxylate (Compound 14)

To a stirred solution of methyl 3-(benzyloxy)-4-oxo-1-((2,3,4,5-tetrahydrobenzo[b]oxepin-5-yl)amino)-1,4-dihydropyridine-2-carboxylate (200 mg, 0.47 mmol) in MeOH (4 mL) was added 10% Pd/C (30 mg) and applied H2 balloon pressure for 16 h. Reaction mixture was filtered through celite bed and washed with Methanol. Filtrate was evaporated under reduced pressure to afford methyl 3-hydroxy-4-oxo-1-((2,3,4,5-tetrahydrobenzo[b]oxepin-5-yl)amino)-1,4-dihydropyridine-2-carboxylate the title compound. LCMS (ESI): m/z 331.25 (M+H).$^+$

Example 4: Synthesis of Compound 23

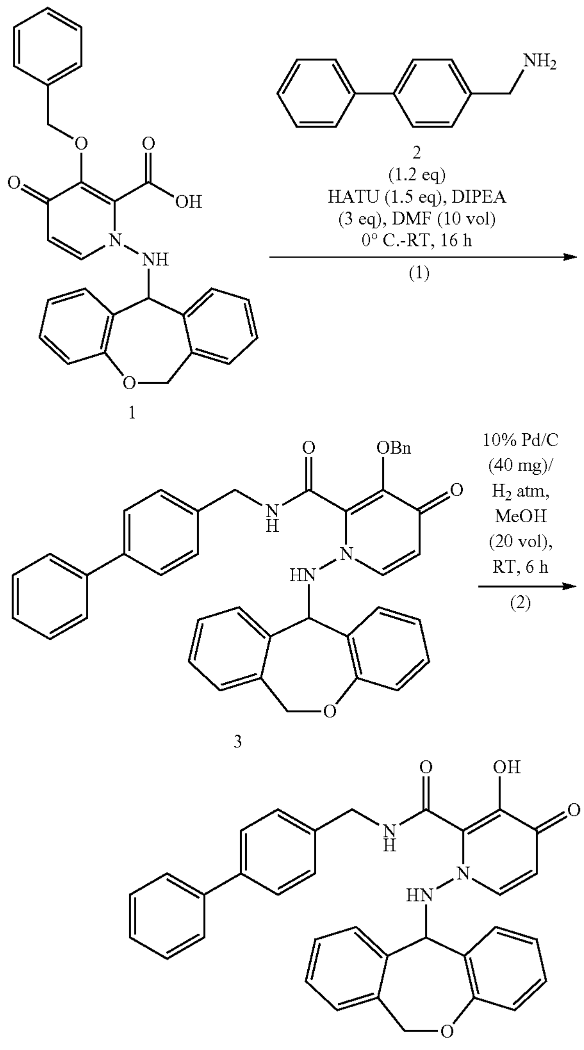

1

2

3

23

Synthesis of 3-(Benzyloxy)-N-(biphenyl-4-ylmethyl)-1-(6,11-dihydrodibenzo[b,e]oxepin-11-ylamino)-4-oxo-1,4-dihydropyridine-2-carboxamide: To a stirred solution of 3-(benzyloxy)-1-(6,11-dihydrodibenzo[b,e]oxepin-11-ylamino)-4-oxo-1,4-dihydropyridine-2-carboxylic acid 1 (200 mg, 0.44 mmol), biphenyl-4-ylmethanamine (121 mg, 0.66 mmol) in DMF (4 mL) was added HATU (250 mg, 0.66 mmol), DIPEA (0.23 mL, 1.32 mmol) & stirred at RT for 16 h. Reaction mixture was diluted with cold water extracted with EtOAC (2×50 mL). Combined organic layers were evaporated under reduced pressure to afford crude product, Crude compound was purified by Grace reverse purification to afford 3-(Benzyloxy)-N-(biphenyl-4-ylmethyl)-1-(6,11-dihydrodibenzo[b,e]oxepin-11-ylamino)-4-oxo-1,4-dihydropyridine-2-carboxamide Synthesis of N-(Biphenyl-4-ylmethyl)-1-(6,11-dihydrodibenzo[b,e]oxepin-11-ylamino)-3-hydroxy-4-oxo-1,4-dihydropyridine-2-carboxamide (compound 23): To a stirred solution of 3-(Benzyloxy)-N-(biphenyl-4-ylmethyl)-1-(6,11-dihydrodibenzo[b,e]oxepin-11-ylamino)-4-oxo-1,4-dihydropyridine-2-carboxamide 3 (120 mg, 0.193 mmol) in methanol (5 mL) was added 10% Pd/C (40 mg) stirred at RT for 3 h under $H_2$ balloon pressure. Reaction mixture was filtered through celite bed and evaporated under reduced pressure to afford crude product. This crude was purified by solvent triturations to afford the title compound. LCMS (ESI): m/z 530.1 $(M+H)^+$ Example 5: Synthesis of Compounds 40 and 43

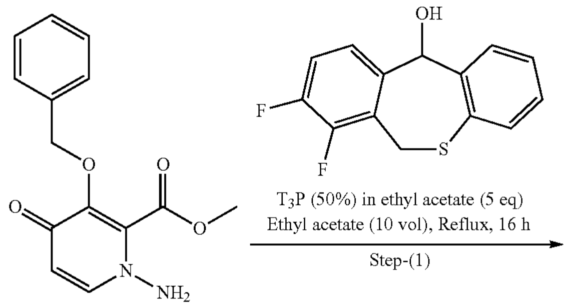

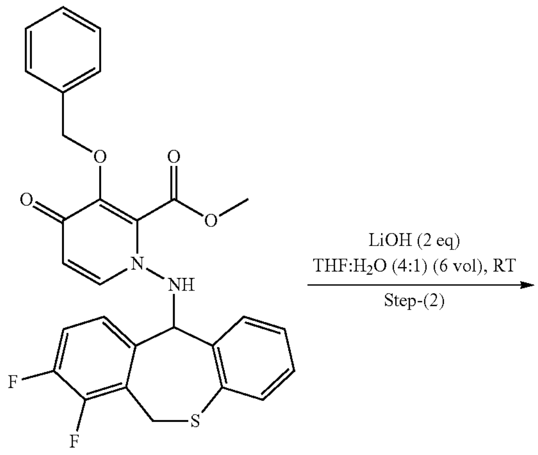

1

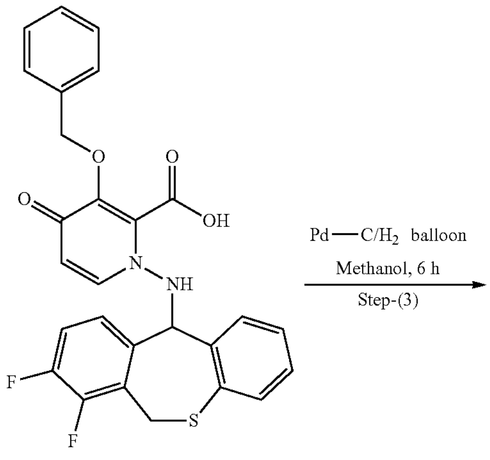

2

-continued

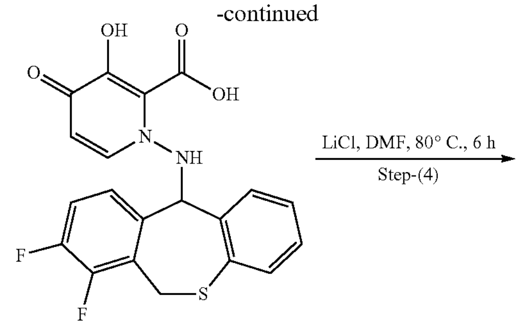

40

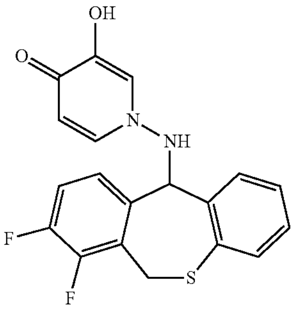

43

Synthesis of methyl 3-(benzyloxy)-1-((7,8-difluoro-6,11-dihydrodibenzo[b,e]thiepin-11-yl)amino)-4-oxo-1,4-dihydropyridine-2-carboxylate (1): To a mixture of methyl 1-amino-3-(benzyloxy)-4-oxo-1,4-dihydropyridine-2-carboxylate (1.5 g, 5.4347 mmol) and 7,8-difluoro-6,11-dihydrodibenzo[b,e]thiepin-11-ol (2 g, 7.608 mmol) (10 mL) was added 50% $T_3P$ in ethyl acetate (17 mL, 27.1735 mmol) and stirred the reaction mixture at 100° C. for 1 h. To the reaction mixture was added water (20 mL) and extracted with ethyl acetate (2×50 mL). Combined organic layers were washed with brine solution (30 mL), dried over sodium sulfate, evaporated under reduced pressure to afford methyl 3-(benzyloxy)-1-((7,8-difluoro-6,11-dihydrodibenzo[b,e]thiepin-11-yl)amino)-4-oxo-1,4-dihydropyridine-2-carboxylate 1

Synthesis of 3-(benzyloxy)-1-((7,8-difluoro-6,11-dihydrodibenzo[b,e]thiepin-11-yl)amino)-4-oxo-1,4-dihydropyridine-2-carboxylic acid 2: To a stirred solution of methyl 3-(benzyloxy)-1-((7,8-difluoro-6,11-dihydrodibenzo[b,e]thiepin-11-yl)amino)-4-oxo-1,4-dihydropyridine-2-carboxylate 1 (650 mg, 1.25 mmol) in tetrahydrofuran (3 mL) and water (1 mL) was added lithium hydroxide (60 mg, 2.469 mmol) then stirred at room temperature for 16 h. Reaction mass was concentrated under reduced pressure, added water, acidified with sat.NaHSO4 solution (3 mL) until solid was precipitated out. Solid was filtered and washed with water to afford 3-(benzyloxy)-1-((7,8-difluoro-6,11-dihydrodibenzo[b,e]thiepin-11-yl)amino)-4-oxo-1,4-dihydropyridine-2-carboxylic acid 2

Synthesis of 1-((7,8-difluoro-6,11-dihydrodibenzo[b,e]thiepin-11-yl)amino)-3-hydroxy-4-oxo-1,4-dihydropyridine-2-carboxylic acid (compound 40): To a stirred solution of 3-(benzyloxy)-1-((7,8-difluoro-6,11-dihydrodibenzo[b,e]thiepin-11-yl)amino)-4-oxo-1,4-dihydropyridine-2-carboxylic acid 2 (200 mg, 0.395 mmol) in methanol (2 mL) and ethyl acetate (2 mL) was added 10% Pd—C (20 mg, 10% w/w) and stirred under hydrogen balloon atmosphere for 6 h. Reaction mixture was filtered through celite bed and washed the celite bed with 10% methanol in dichloromethane (20 mL) and filtrate was concentrated under reduced pressure. Crude compound was purified by Grace reverse phase purification to afford pure compound 1-((7,8-difluoro-6,11-dihydrodibenzo[b,e]thiepin-11-yl)amino)-3-hydroxy-4-oxo-1,4-dihydropyridine-2-carboxylic acid Synthesis of 1-((7,8-difluoro-6,11-dihydrodibenzo[b,e]thiepin-11-yl)amino)-3-hydroxypyridin-4(1H)-one (compound 43): To a stirred solution of 1-((7,8-difluoro-6,11-dihydrodibenzo[b,e]thiepin-11-yl)amino)-3-hydroxy-4-oxo-1,4-dihydropyridine-2-carboxylic acid (150 mg, 0.3246 mmol) in DMF (2 mL) was added lithium chloride (27.3 mg, 0.6493 mmol) at RT and stirred at 100° C. for 6 h. After completion of the reaction (monitored by TLC), added chilled water (20 mL), solid was filtered and dried. Obtained crude solid was purified by prep-HPLC to afford compound 43. LCMS (ESI): m/z 373.132 $(M+H)^+$ Example 6: Synthesis of Compound 42

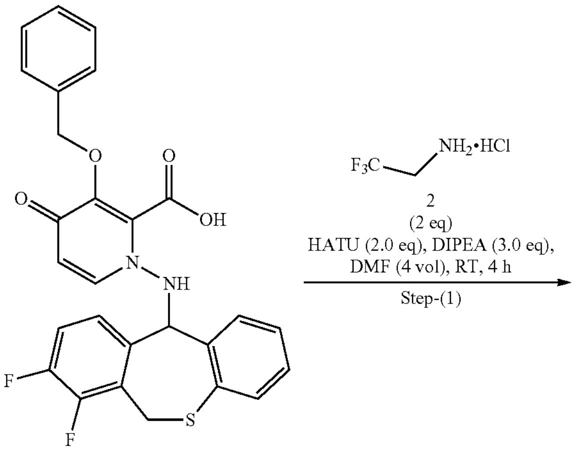

1

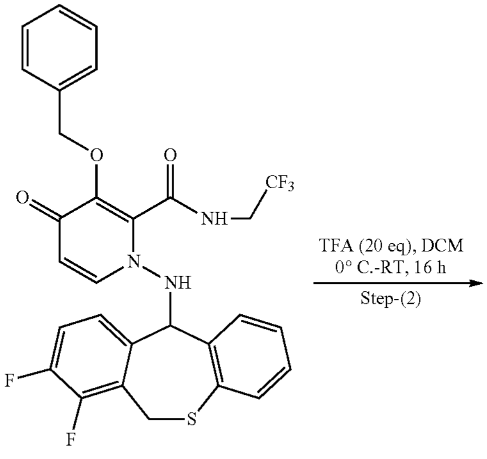

3

-continued

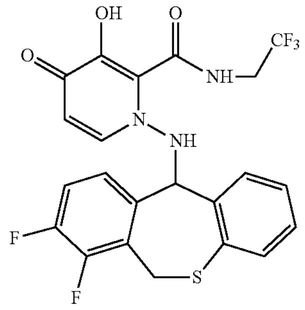

42

Synthesis of 3-(benzyloxy)-1-((7,8-difluoro-6,11-dihydrodibenzo[b,e]thiepin-11-yl)amino)-4-oxo-N-(2,2,2-trifluoroethyl)-1,4-dihydropyridine-2-carboxamide 3: To a stirred solution of 3-(benzyloxy)-1-((7,8-difluoro-6,11-dihydrodibenzo[b,e]thiepin-11-yl)amino)-4-oxo-1,4-dihydropyridine-2-carboxylic acid 1 (100 mg, 0.1976 mmol) in DMF (2 mL) was added HATU (150 mg, 0.3952 mmol) and DIPEA (0.1 mL, 0.494 mmol). Stirred the reaction mixture for 5 min, then added 2,2,2-trifluoroethan-1-amine hydrochloride 2 (30 mg, 0.2964 mmol). Reaction mixture was stirred at room temperature for 16 h. After completion of the reaction (monitored by TLC) charged ice cold water (30 ml), solid was filtered and dried to afford 3-(benzyloxy)-1-((7,8-difluoro-6,11-dihydrodibenzo[b,e]thiepin-11-yl)amino)-4-oxo-N-(2,2,2-trifluoroethyl)-1,4-dihydropyridine-2-carboxamide 3

Synthesis of 1-((7,8-difluoro-6,11-dihydrodibenzo[b,e]thiepin-11-yl)amino)-3-hydroxy-4-oxo-N-(2,2,2-trifluoroethyl)-1,4-dihydropyridine-2-carboxamide (compound 42): To a stirred solution of 3-(benzyloxy)-1-((7,8-difluoro-6,11-dihydrodibenzo[b,e]thiepin-11-yl)amino)-4-oxo-N-(2,2,2-trifluoroethyl)-1,4-dihydropyridine-2-carboxamide 3 (150 mg, 0.255 mmol) in DCM (1 mL) was added trifluoroacetic acid (0.37 mL) at 0° C. and stirred at RT for 16 h. Reaction mixture was concentrated under reduced pressure. Crude residue was purified by prep-HPLC to afford the title compound. LCMS (ESI): m/z 498.20 $(M+H)^+$ Example 7: Synthesis of Compound 58

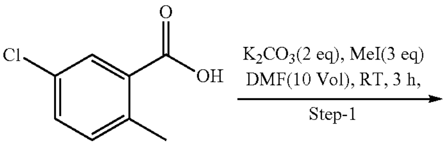

1

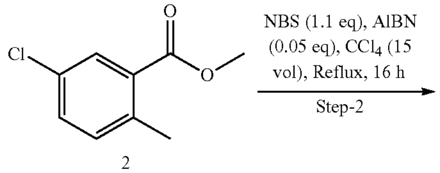

2

-continued

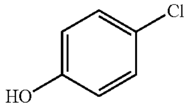

4

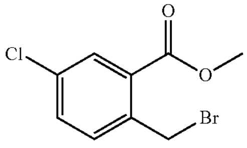

3

$K_2CO_3$ (1.5 eq), DMF
(10 vol), 1 RT, 6 h
Step-3

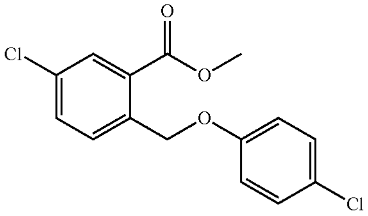

5

LiOH (3 eq), THF, $H_2O$
(4:1, 10 vol), RT, 16 h
Step-4

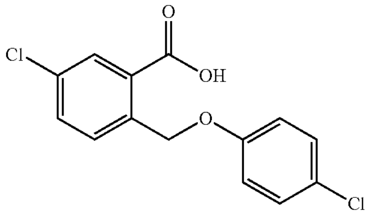

6

Triflic anhydride(2 eq)
$BF_3$—$Et_2O$ (0.2 eq),
DCM, 40° C., 3 h
Step-5

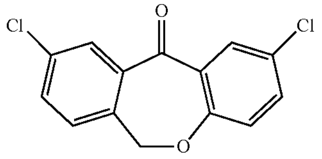

7

$NaBH_4$ (4 eq),
MeOH/THF(1:2)
(10 vol), RT, 3 h
Step-6

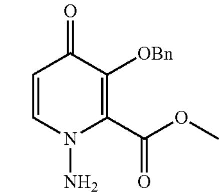

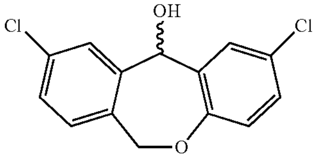

8

50% $T_3P$ in EtOAc(5 eq),
EtOAc (5 vol), 100° C., 3 h
Step-7

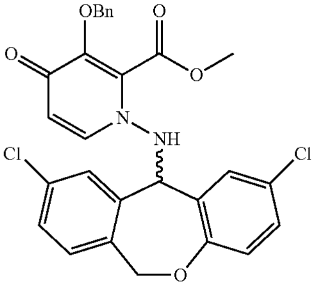

9

LiOH (3 eq), THF, $H_2O$
(4:1, 10 vol), RT, 16 h
Step-8

-continued

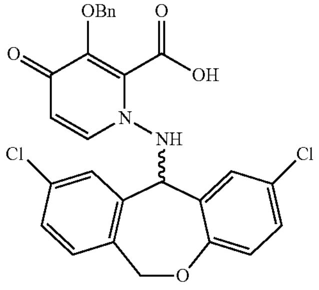

10

TFA (40 eq)/DCM, RT, 12 h
Step-9

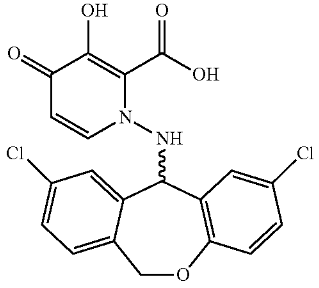

58

Synthesis of Methyl 5-chloro-2-methylbenzoate (2): To a stirred solution of 5-chloro-2-methylbenzoic acid 1 (500 mg, 2.941 mmol) in DMF (10 mL) was added potassium carbonate (811 mg, 5.882 mmol) followed by methyl iodide (0.54 mL, 8.823 mmol) at 0° C. then stirred at RT for 3 h. Reaction mixture was quenched with ice cold water (30 mL) and extracted with diethyl ether (2×30 mL), Organic layers were combined, washed with brine solution (50 mL) and dried over sodium sulfate and concentrated under reduced pressure to afford pure compound methyl 5-chloro-2-methylbenzoate 2

Synthesis of Methyl 2-(bromomethyl)-5-chlorobenzoate (3): To a stirred solution of methyl 5-chloro-2-methylbenzoate 2 (5.2 g, 28.25 mmol) in carbon tetrachloride (50 mL) was added N-bromosuccinimide (5.03 g, 28.25 mmol) and AIBN (234 mg, 1.426 mmol) at room temperature and stirred at 80° C. for 16 h. To the reaction mixture was added water (200 mL) and extracted with dichloromethane (2×100 mL). Combined organic layers were washed with brine solution (100 mL), dried over sodium sulfate and concentrated under reduced pressure to afford methyl 2-(bromomethyl)-5-chlorobenzoate 3

Synthesis of Methyl 5-chloro-2-((4-chlorophenoxy) methyl) benzoate (5): To a stirred solution of methyl 2-(bromomethyl)-5-chlorobenzoate 3 (5.4 g, 20.61 mmol) in N,N-dimethylformamide (50 mL) was added potassium carbonate (5.68 g, 41.22 mmol) and 4-chloro phenol 4 (3.95 g, 30.916 mmol) at 0° C. and stirred at room temperature for 6 h. To the reaction mixture was added water (200 mL) and extracted with ethyl acetate (2×100 mL). Combined organic layers were washed with brine solution (50 mL), dried over sodium sulfate and concentrated under reduced pressure to afford crude product, this crude residue was triturated with diethyl ether to afford pure methyl 2-(bromomethyl)-5-chlorobenzo methyl 5-chloro-2-((4-chlorophenoxy)methyl) benzoate 5

Synthesis of 5-Chloro-2-((4-chlorophenoxy) methyl) benzoic acid (6): To a stirred solution of methyl 2-(bromomethyl)-5-chlorobenzo methyl 5-chloro-2-((4-chlorophenoxy) methyl)benzoate 5 (4.2 g, 13.544 mmol) in tetrahydrofuran (60 mL) and water (20 mL) was added lithium hydroxide (0.97 g, 40.632 mmol) at 0° C. then stirred at room temperature for 16 h. After consumption of starting material, the reaction mixture was concentrated under reduced pressure, to the residue was added water (40 mL) and acidified with 2N HCl solution. Precipitated solids were filtered and washed with water then dried under vacuum to afford pure 5-chloro-2-((4-chlorophenoxy) methyl) benzoic acid 6

Synthesis of 2,9-Dichlorodibenzo[b,e]oxepin-11(6H)-one (7): To a stirred solution of 5-chloro-2-((4-chlorophenoxy) methyl) benzoic acid 6 (300 mg, 1.013 mmol) in dichloromethane (10 mL) was added trifluoroacetic anhydride (0.34 mL, 2.027 mmol) and borontrifluoride etherate (30 μL, 0.202 mmol) at 0° C. and stirred at 40° C. for 3 h. Reaction mixture was diluted with DCM (30 mL) and washed with sat.$NaHCO_3$ solution (2×30 mL), brine solution (30 mL), dried over sodium sulfate and concentrated under reduced pressure to afford pure 9-dichlorodibenzo[b,e]oxepin-11 (6H)-one 7

Synthesis of 2,9-Dichloro-6,11-dihydrodibenzo[b,e]oxepin-11-ol (8): To a stirred solution of 9-dichlorodibenzo[b,e]oxepin-11(6H)-one 7 (260 mg, 0.935 mmol) in methanol (5 mL) & THF (10 mL) was added sodium borohydride (71 mg, 1.87 mmol) at 0° C. then stirred at room temperature for 3 h. To the reaction mixture was added water (50 mL) and extracted with ethyl acetate (2×100 mL). Combined organic layers were washed with brine solution (50 mL), dried over sodium sulfate and concentrated under reduced pressure to afford pure compound 2,9-dichloro-6,11-dihydrodibenzo[b,e]oxepin-11-ol 8

Synthesis of Methyl 3-(benzyloxy)-1-((2,9-dichloro-6,11-dihydrodibenzo[b,e]oxepin-11-yl)amino)-4-oxo-1,4-dihydropyridine-2-carboxylate (9): To a mixture of methyl 1-amino-3-(benzyloxy)-4-oxo-1,4-dihydropyridine-2-carboxylate KI-1 (140 mg, 0.51 mmol and 2,9-dichloro-6,11-dihydrodibenzo[b,e]oxepin-11-ol 8 (214 mg, 0.766 mmol) in ethyl acetate (10 mL) was added 50% $T_3P$ in ethyl acetate (1.6 g, 5.100 mmol) and stirred the reaction mixture at 100° C. for 3 h. To the reaction mixture was added water (50 mL) and extracted with ethyl acetate (2×50 mL). Combined the organic layers and washed with brine solution (30 mL), dried over sodium sulfate and evaporated under reduced pressure to afford crude methyl 3-(benzyloxy)-1-((2,9-dichloro-6,11-dihydrodibenzo[b,e]oxepin-11-yl)amino)-4-oxo-1,4-dihydropyridine-2-carboxylate 9

Synthesis of 3-(Benzyloxy)-1-((2,9-dichloro-6,11-dihydrodibenzo[b,e]oxepin-11-yl)amino)-4-oxo-1,4-dihydropyridine-2-carboxylic acid (10): To a stirred solution of methyl 3-(benzyloxy)-1-((2,9-dichloro-6,11-dihydrodibenzo[b,e]oxepin-11-yl)amino)-4-oxo-1,4-dihydropyridine-2-carboxylate (9) (150 mg, 0.279 mmol) in tetrahydrofuran (6 mL) and water (2 mL) was added lithium hydroxide (20 mg, 0.839 mmol) then stirred at room temperature for 16 h. Reaction mixture was completely distilled under reduced pressure, to the crude was added water and acidified with NaHSO4 solution (20 mL). Solid was precipitated out, it was filtered and washed with water to afford 3-(benzyloxy)-1-((2,9-dichloro-6,11-dihydrodibenzo[b,e]oxepin-11-yl) amino)-4-oxo-1,4-dihydropyridine-2-carboxylic acid (10)

Synthesis of 1-((2,9-dichloro-6,11-dihydrodibenzo[b,e] oxepin-11-yl)amino)-3-hydroxy-4-oxo-1,4-dihydropyridine-2-carboxylic acid (compound 58): To a stirred solution of 3-(benzyloxy)-1-((2,9-dichloro-6,11-dihydrodibenzo[b,e] oxepin-11-yl)amino)-4-oxo-1,4-dihydropyridine-2-carboxylic acid (10) (100 mg, 0.191 mmol) in dichloromethane (2 mL) was added TFA (0.5 mL, 7.66 mmol) and stirred at RT for 12 h. Reaction mixture was evaporated under reduced pressure to afford crude product. This crude was purified through prep HPLC purification to afford 1-((2, 9-dichloro-6, 11-dihydrodibenzo [b, e] oxepin-11-yl) amino)-3-hydroxy-4-oxo-1, 4-dihydropyridine-2-carboxylic acid (compound 58). LCMS (ESI): m/z 433.22 $(M+H)^+$ Compounds 59, 60, 77, 80, 87, 88, 90, 93, 94, 95, 96, 99, 114, 115, 116, 117, 123, and 126 were prepared in the same manner as compound 58.

Compound 59: LCMS (ESI): m/z 381.2 $(M+H)^+$

Compound 60: LCMS (ESI): m/z 433.22 $(M+H)^+$

Compound 77: LCMS (ESI): m/z 449.2 $(M+H)^+$

Compound 80: LCMS (ESI): m/z 437.28 $(M+H)^+$

Compound 87: LCMS (ESI): m/z 449.20 $(M+H)^+$

Compound 88: LCMS (ESI): m/z 417.27 $(M+H)^+$

Compound 90: LCMS (ESI): m/z 421.19 $(M+H)^+$

Compound 93: LCMS (ESI): m/z 453.23 $(M+H)^+$

Compound 94: LCMS (ESI): m/z 449.2 $(M+H)^+$

Compound 95: LCMS (ESI): m/z 417.23 $(M+H)^+$

Compound 96: LCMS (ESI): m/z 477.17 $(M+H)^+$

Compound 99: LCMS (ESI): m/z 433.22 $(M+H)^+$

Compound 114: LCMS (ESI): m/z 491.32 $(M-H)^-$

Compound 115: LCMS (ESI): m/z 411.01 $(M+H)^+$

Compound 116: LCMS (ESI): m/z 501 $(M+H)^+$

Compound 117: LCMS (ESI): m/z 449.29 $(M+H)^+$

Compound 123: LCMS (ESI): m/z 511.04 $(M+H)^+$

Compound 126: LCMS (ESI): m/z 449.02 $(M+H)^+$.

Example 8: Synthesis of Compound 76

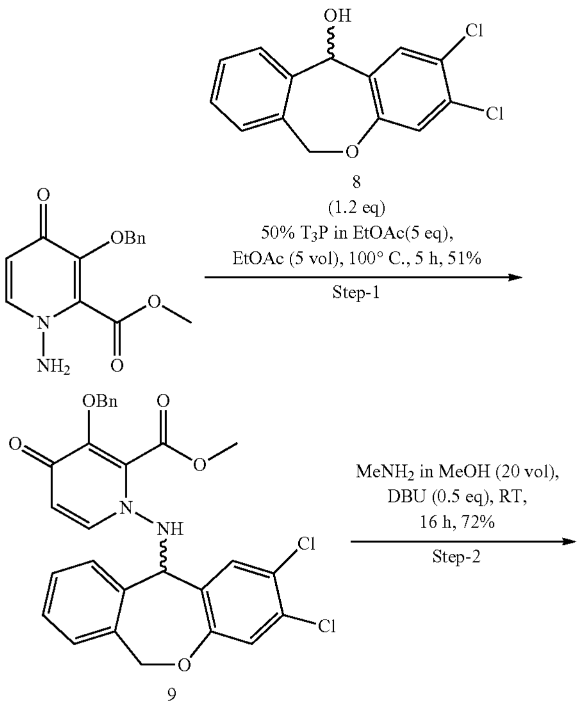

-continued

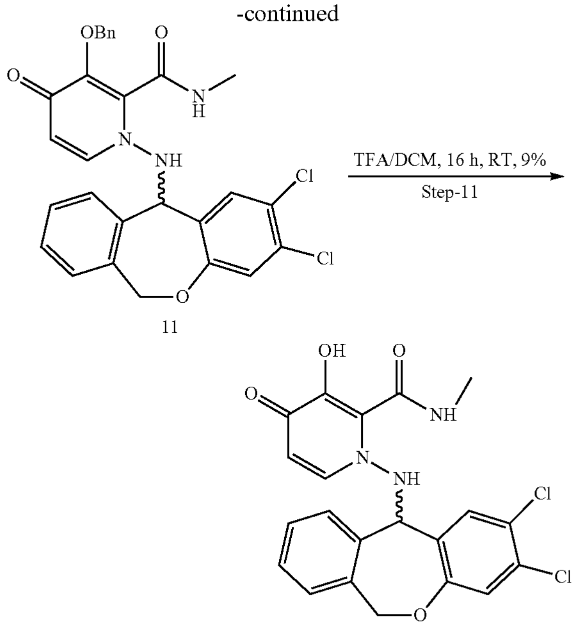

11

76

Synthesis of Methyl 3-(benzyloxy)-1-((2,3-dichloro-6,11-dihydrodibenzo[b,e]oxepin-11-yl)amino)-4-oxo-1,4-dihydropyridine-2-carboxylate (9): To a mixture of methyl 1-amino-3-(benzyloxy)-4-oxo-1,4-dihydropyridine-2-carboxylate (500 mg, 1.8248 mmol) and 2,3-dichloro-6,11-dihydrodibenzo[b,e]oxepin-11-ol (8) (766 mg, 2.7372 mmol) was added 50% $T_3P$ in ethyl acetate (5.8 ml, 9.1240 mmol) and stirred the reaction mixture at 100° C. for 5 h. To the reaction mixture was added water (100 mL) and extracted with ethyl acetate (100 mL). Organic layer was washed with brine solution (100 mL), dried over $Na_2SO_4$, evaporated under reduced pressure. Crude compound was purified through 100-200 silica gel column chromatography by eluting with 2% methanol in dichloromethane to afford methyl 3-(benzyloxy)-1-((2,3-dichloro-6,11-dihydrodibenzo[b,e]oxepin-11-yl)amino)-4-oxo-1,4-dihydropyridine-2-carboxylate 9

Synthesis of 3-(benzyloxy)-1-((2,3-dichloro-6,11-dihydrodibenzo[b,e]oxepin-11-yl)amino)-N-methyl-4-oxo-1,4-dihydropyridine-2-carboxamide (11): A solution of methyl 3-(benzyloxy)-1-((2,3-dichloro-6,11-dihydrodibenzo[b,e]oxepin-11-yl)amino)-4-oxo-1,4-dihydropyridine-2-carboxylate (9) (250 mg, 0.4604 mmol), methyl amine in MeOH (5 ml) and DBU (12 mg, 00.932 mmol) was stirred at RT for 16 h in a sealed tube. To the reaction mixture was added cold water, precipitated out solid was filtered and dried under vacuum to afford 3-(benzyloxy)-1-((2,3-dichloro-6,11-dihydrodibenzo[b,e]oxepin-11-yl)amino)-N-methyl-4-oxo-1,4-dihydropyridine-2-carboxamide (11)

1-((2,3-dichloro-6,11-dihydrodibenzo[b,e]oxepin-11-yl)amino)-3-hydroxy-N-methyl-4-oxo-1,4-dihydropyridine-2-carboxamide (compound 76): To a stirred solution of 3-(benzyloxy)-1-((2,3-dichloro-6,11-dihydrodibenzo[b,e]oxepin-11-yl)amino)-N-methyl-4-oxo-1,4-dihydropyridine-2-carboxamide (11) (130 mg, 0.2429 mmol) in DCM was added TFA (0.5 ml) at 0° C. and stirred at RT for 16 h. Organic solvents were distilled off to afford crude compound and it was further purified by prep HPLC purification to afford the title compound. LCMS (ESI): m/z 446.35 $(M+H)^+$ Compound 89 was prepared in the same manner as compound 76.

Compound 89: LCMS (ESI): m/z 462.23 $(M+H)^+$

Example 9: Synthesis of Compound 65

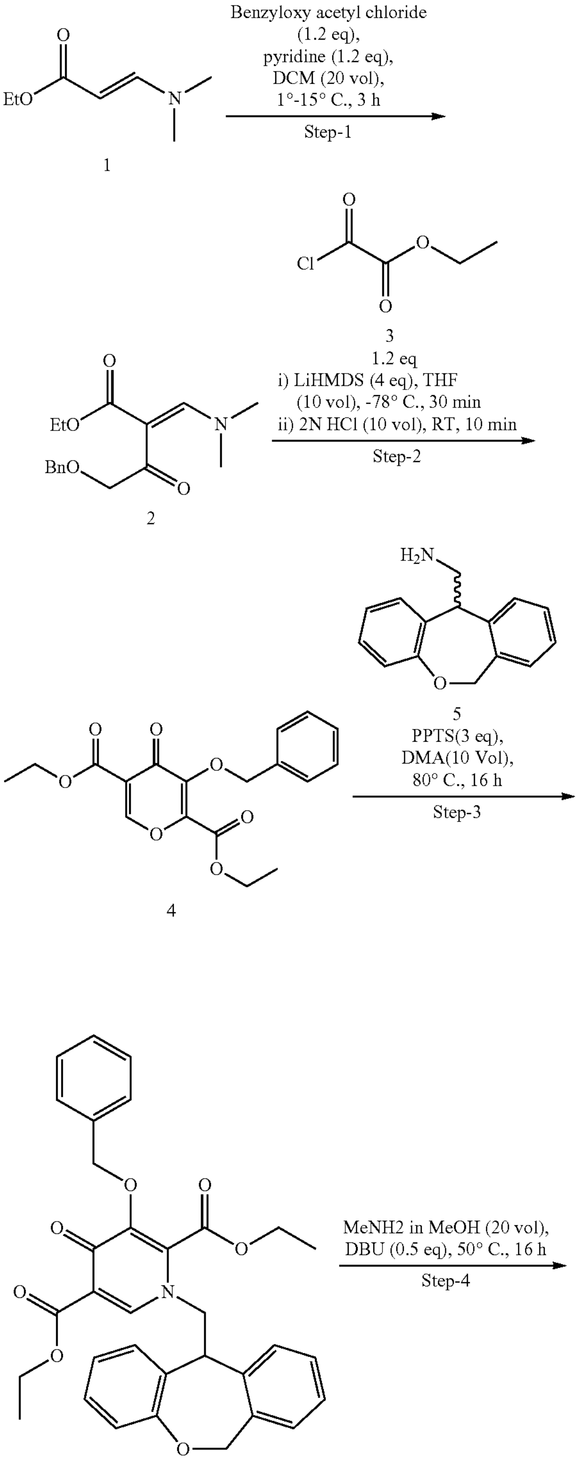

1

3

2

5

4

6

-continued

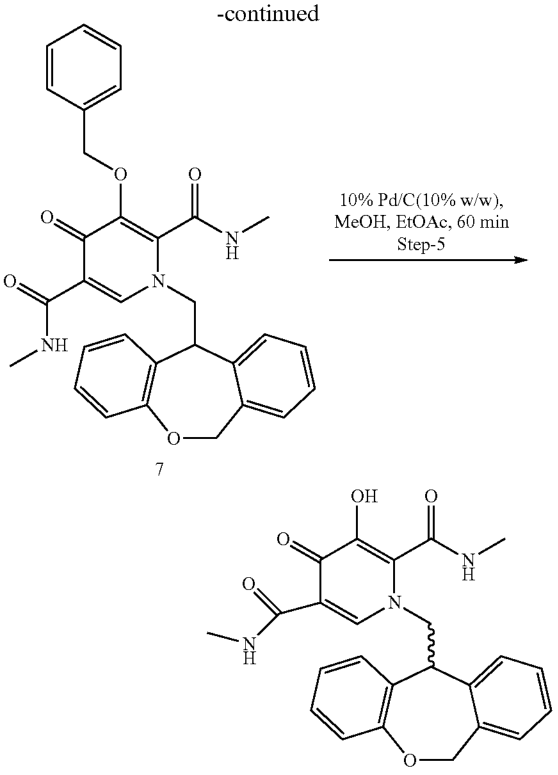

7

65

Synthesis of Ethyl (E)-4-(benzyloxy)-2-((dimethylamino)methylene)-3-oxobutanoate (2): To a stirred solution of ethyl (E)-3-(dimethylamino)acrylate (1) (5 g, 34.900 mmol) in dichloromethane (100 mL) and pyridine (3.3 g, 41.9000 mmol) was added benzyloxy acetyl chloride (7.8 g, 41.9000 mmol) drop wise at 0° C. over 50 min and stirred the reaction mixture at the same temperature for 30 min. Raised the temperature to 50° C. and stirred at the same temperature for 90 min. To the reaction mixture was added water (3×100 mL) and extracted with dichloromethane (5×100 mL). Combined organic layers were washed with brine solution (100 mL), dried over $Na_2SO_4$ and evaporated under reduced pressure. Crude residue was purified through silica gel column chromatography to afford ethyl (E)-4-(benzyloxy)-2-((dimethylamino)methylene)-3-oxobutanoate (2)

Synthesis of diethyl 3-(benzyloxy)-4-oxo-4H-pyran-2,5-dicarboxylate (4): To a stirred solution of ethyl (E)-4-(benzyloxy)-2-((dimethylamino)methylene)-3-oxobutanoate (2) (3.g, 10.3092 mmol) in THF (40 mL) was added LiHMDS (25.7 mL, 25.7731 mmol) at −78° C. Stirred the reaction mixture for 10 min then added ethyl 2-chloro-2-oxoacetate (3) (2.1 g, 15.4639 mmol) in THF at −78° C. and stirred at same temperature for 2 h. Reaction mixture was quenched with 2N HCl at −78° C. and allowed the reaction mixture warmed to room temperature. To the reaction mixture was added water (3×100 mL) and extracted with ethyl acetate (5×100 mL). Combined organic layers were washed with brine solution (100 mL) and sodium bicarbonate solution (100 mL), dried over $Na_2SO_4$ and evaporated under reduced pressure. Crude residue was purified through Grace reverse phase purification to afford diethyl 3-(benzyloxy)-4-oxo-4H-pyran-2,5-dicarboxylate (4)

Synthesis of diethyl 3-(benzyloxy)-1-((6,11-dihydrodibenzo[b,e]oxepin-11-yl)methyl)-4-oxo-1,4-dihydropyridine-2,5-dicarboxylate (6): To a stirred solution of diethyl 3-(benzyloxy)-4-oxo-4H-pyran-2,5-dicarboxylate (4) (320 mg, 0.9248 mmol) in DMA (3 mL) was added (6,11-dihydrodibenzo[b,e]oxepin-11-yl)methanamine (5) (270 mg, 1.2023 mmol), pyridinium para toluene sulfonate (464 mg, 1.8497) at room temperature. Stirred the reaction mixture at 60° C. for 16 h. To the reaction mixture added water (2×25 mL) and extracted with ethyl acetate (2×50 mL). Combined organic layers were washed with brine solution (20 mL) and dried over $Na_2SO_4$, evaporated under reduced pressure. Crude residue was purified through C18 Reverse phase to afford diethyl 3-(benzyloxy)-1-((6,11-dihydrodibenzo[b,e]oxepin-11-yl)methyl)-4-oxo-1,4-dihydropyridine-2,5-dicarboxylate (6)

Synthesis of 3-(benzyloxy)-1-((6,11-dihydrodibenzo[b,e]oxepin-11-yl)methyl)-N2,N5-dimethyl-4-oxo-1,4-dihydropyridine-2,5-dicarboxamide (7): To a stirred solution of 3-(benzyloxy)-1-((6,11-dihydrodibenzo[b,e]oxepin-11-yl)methyl)-4-oxo-1,4-dihydropyridine-2,5-dicarboxylate (6) (310 mg, 0.5605 mmol) in methylamine in methanol (4 mL) was added DBU (42 mg, 0.2802 mmol) at room temperature. Stirred the reaction mixture at 50° C. for 16 h. To the reaction mixture added water (2×25 mL) and extracted with ethyl acetate (2×50 mL). Combined organic layers were washed with brine solution (20 mL) and dried over $Na_2SO_4$, evaporated under reduced pressure. Crude residue was purified through C18 Reverse phase to afford 3-(benzyloxy)-1-((6,11-dihydrodibenzo[b,e]oxepin-11-yl)methyl)-N2,N5-dimethyl-4-oxo-1,4-dihydropyridine-2,5-dicarboxamide (7)

Synthesis of 1-((6,11-dihydrodibenzo[b,e]oxepin-11-yl)methyl)-3-hydroxy-N2,N5-dimethyl-4-oxo-1,4-dihydropyridine-2,5-dicarboxamide (compound 65): To a stirred solution of 3-(benzyloxy)-1-((6,11-dihydrodibenzo[b,e]oxepin-11-yl)methyl)-N2,N5-dimethyl-4-oxo-1,4-dihydropyridine-2,5-dicarboxamide (7) (100 mg, 0.1912 mmol) in ethyl acetate (5 mL) and methanol (5 mL) was added 10% Pd/C (10 mg). Stirred the reaction mixture in hydrogen atmosphere at room temperature for 60 min. Filtered the reaction mixture through celite pad, distilled off the organic solvents under reduced pressure. Crude residue was purified through C18 reverse phase to afford the title compound. LCMS (ESI): m/z 434.37 $(M+H)^+$ Example 10: Synthesis of Compound 79

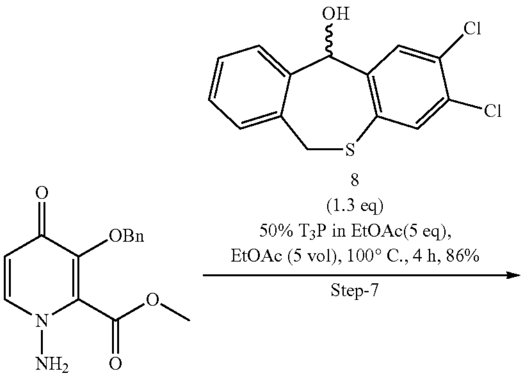

8

-continued

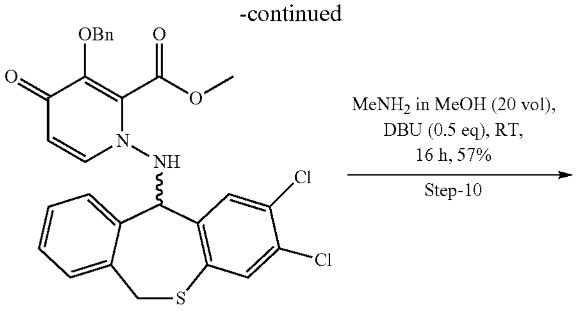

9

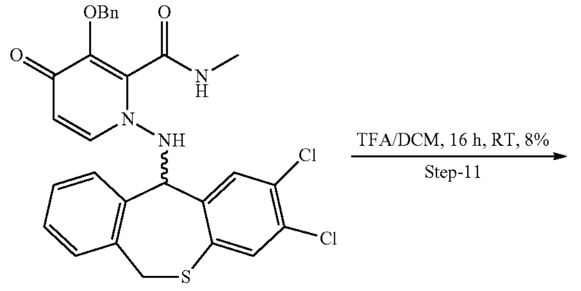

11

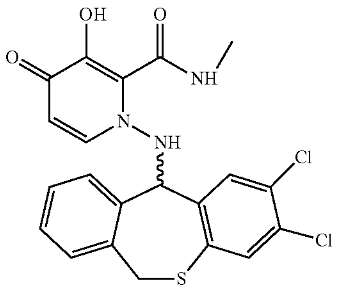

79

Synthesis of methyl 3-(benzyloxy)-1-((2,3-dichloro-6,11-dihydrodibenzo[b,e]thiepin-11-yl)amino)-4-oxo-1,4-dihydropyridine-2-carboxylate (9): To a mixture of methyl 1-amino-3-(benzyloxy)-4-oxo-1,4-dihydropyridine-2-carboxylate KI-1 (400 mg, 1.4598 mmol) and 2,3-dichloro-6,11-dihydrodibenzo[b,e]thiepin-11-ol (8) (559 mg, 1.8977 mmol) was added 50% $T_3P$ in ethyl acetate (4.6 ml, 7.299 mmol) and stirred the reaction mixture at 100° C. for 4 h. To the reaction mixture was added water (50 mL) and extracted with ethyl acetate (100 mL). Organic layer was washed with brine solution (50 mL), dried over $Na_2SO_4$ and evaporated under reduced pressure. Crude compound was purified by column chromatography to afford methyl 3-(benzyloxy)-1-((2,3-dichloro-6,11-dihydrodibenzo[b,e]thiepin-11-yl)amino)-4-oxo-1,4-dihydropyridine-2-carboxylate (9)

Synthesis of 3-(benzyloxy)-1-((2,3-dichloro-6,11-dihydrodibenzo[b,e]thiepin-11-yl)amino)-N-methyl-4-oxo-1,4-dihydropyridine-2-carboxamide (11): A solution of methyl 3-(benzyloxy)-1-((2,3-dichloro-6,11-dihydrodibenzo[b,e]thiepin-11-yl)amino)-4-oxo-1,4-dihydropyridine-2-carboxylate (9) (350 mg, 0.634 mmol), Methyl amine in MeOH (10 ml) and DBU (48 mg, 0.317 mmol) was stirred at RT for 16 h in sealed tube. To the reaction mixture added cold water solid comes out, filtered and dried under vacuum to afford 3-(benzyloxy)-1-((2,3-dichloro-6,11-dihydrodibenzo[b,e]thiepin-11-yl)amino)-N-methyl-4-oxo-1,4-dihydropyridine-2-carboxamide (11)

Synthesis of 1-((2,3-dichloro-6,11-dihydrodibenzo[b,e]thiepin-11-yl)amino)-3-hydroxy-N-methyl-4-oxo-1,4-dihydropyridine-2-carboxamide (compound 79): To a stirred solution of 3-(benzyloxy)-1-((2,3-dichloro-6,11-dihydrodibenzo[b,e]thiepin-11-yl)amino)-N-methyl-4-oxo-1,4-dihydropyridine-2-carboxamide (11) (200 mg, 0.3629 mmol) in DCM (10 mL) was added TFA (3 ml) at 0° C. and stirred at RT for 16 h. Distilled-off the solvents to afford crude compound, crude compound was purified by prep HPLC purification to afford the title compound. LCMS (ESI): m/z 462.27 $(M+1)^+$ Compound 78 was prepared in the same manner as compound 79.

Compound 78: LCMS (ESI): m/z 430.3 $(M+1)^+$

Example 11: Synthesis of Compound 130

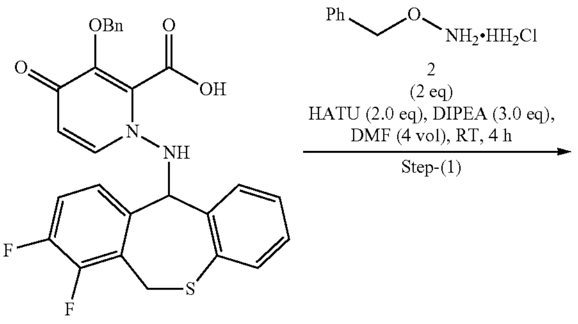

1

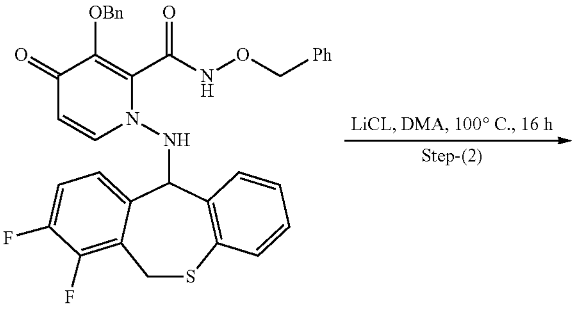

3

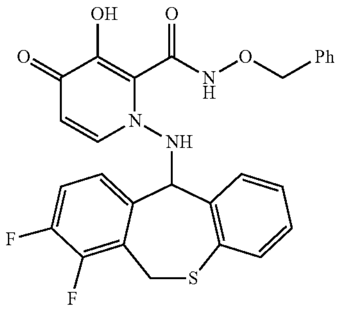

130

Synthesis of N,3-bis(benzyloxy)-1-((7,8-difluoro-6,11-dihydrodibenzo[b,e]thiepin-11-yl)amino)-4-oxo-1,4-dihydropyridine-2-carboxamide 3: To the stirred solution of 3-(benzyloxy)-1-((7,8-difluoro-6,11-dihydrodibenzo[b,e]thiepin-11-yl)amino)-4-oxo-1,4-dihydropyridine-2-carboxylic acid 1 (500 mg, 0.9881 mmol) in DMF (5 mL) was added HATU (750 mg, 1.9762 mmol) and DIPEA (0.69 mL, 3.9524 mmol). Stirred the reaction mixture for 5 min, then added O-benzylhydroxylamine hydrochloride (2) (314 mg, 1.9762 mmol) and stirred the reaction mixture at room temperature for 16 h. To the reaction mixture was added ice cold water (30 ml), precipitated solid was filtered and dried to afford N,3-bis(benzyloxy)-1-((7,8-difluoro-6,11-dihydrodibenzo [b,e]thiepin-11-yl)amino)-4-oxo-1,4-dihydropyridine-2-carboxamide 3. LCMS (ESI): m/z 611.92 $(M+H)^+$ Synthesis of N-(benzyloxy)-1-((7,8-difluoro-6,11-dihydrodibenzo[b,e]thiepin-11-yl)amino)-3-hydroxy-4-oxo-1,4-dihydropyridine-2-carboxamide (compound 130): To a stirred solution of N,3-bis(benzyloxy)-1-((7,8-difluoro-6,11-dihydrodibenzo[b,e]thiepin-11-yl)amino)-4-oxo-1,4-dihydropyridine-2-carboxamide 3 (200 mg, 0.3273 mmol) in DMA (2 mL) was added lithium chloride (55 mg, 1.3093 mmol) at RT and stirred at 100° C. for 16 h. To the reaction mixture was added ice cold water (20 mL) and precipitated solid was filtered and dried. This solid was purified by prep-HPLC to afford the title compound. LCMS (ESI): m/z 522.51 $(M+H)^+$ Other specific compounds disclosed herein were synthesized using the reaction schemes as described above, with use of the appropriate starting materials and reagents.

Example 12: Data on Selected Compounds

In Vitro Antiviral Assays

Influenza Antiviral Assays:

Inhibition of virus-induced cytopathic effects (CPE) and cell viability following Influenza type A (strain A/PR/8/34, ATCC VR-95) or Influenza type B (cell culture adapted strain B/Lee/40, ATCC VR-1535) replication in MDCK cells (Female cocker spaniel kidney epithelial, ATCC CCL-34) were measured by XTT dye reduction (Appleyard et al. J Antimicrob Chemother. 1(4 Suppl): 49-53, 1975 and Shigeta et al. Antimicrob Agents Chemother. 41(7): 1423-1427, 1997.). MDCK cells ($1\times10^4$ cells per well) are grown to monolayers in 96-well flat-bottomed tissue culture plates using Dulbecco's Minimum Essential Medium (DMEM) supplemented with 10% heat-inactivated fetal bovine serum (FBS), 2 mM L-glutamine, 100 U/mL penicillin, 100 μg/ml streptomycin, 1 mM sodium pyruvate, and 0.1 mM NEAA in a 100 μL per well volume. On the day of assay set up, the cell monolayer was washed three times with DPBS. The viruses were obtained from ATCC and were grown in MDCK cells for the production of stock virus pools. Test compounds were diluted into assay medium (DMEM, 2 mM L-glutamine, 100 U/mL penicillin, 100 μg/mL streptomycin, 50 ng/ml TPCK-treated trypsin, 0.1 mM NEAA, and 1 mM sodium pyruvate) at 2× the desired starting concentration and serially diluted. Test compound was added at 100 μL per well volume in triplicate for efficacy, duplicate for cytotoxicity and a single well per concentration for colorimetric evaluation immediately prior to the addition of diluted virus. Ribavirin and oseltamivir carboxylate were evaluated in parallel as control compounds. A pretitered aliquot of virus was removed from the freezer (−80° C.) and was rapidly thawed in a biological safety cabinet. Virus was diluted in assay medium such that the amount of virus added to each well in a volume of 100 μL was the amount determined to yield 85 to 95% cell killing at 4 days post-infection. Cell controls containing medium alone, virus-infected controls containing medium and virus, cytotoxicity controls containing medium and each Following incubation at 37° C., 5% $CO_2$ for four days, inhibition of CPE (increased cell viability) was measured by reduction of the formazan dye XTT following a 4 hour incubation at 37° C. and measured spectrophotometrically at 450 nm, with 650 nm as the reference wavelength using Softmax Pro 4.6 software. Percent CPE reduction of the virus-infected wells and the percent cell viability of uninfected drug control wells are calculated by four parameter curve fit analysis using Microsoft Excel XLfit4.

Potency against Influenza A (H1N1) $EC_{50}$ values are reported in Table B. Values are reported as follows: ++++: $EC_{50}$<0.1 μM; +++: $EC_{50}$=0.1-1 μM; ++: $EC_{50}$=1-10 μM; +: $EC_{50}$=10-100 μM; and −: $EC_{50}$>100 μM.

TABLE B

| Compound No. | Influenza H1N1 affinity, $EC_{50}$ |
|---|---|
| 1 | + |
| 2 | + |
| 4 | − |
| 5 | − |
| 6 | ++ |
| 8 | − |
| 9 | − |
| 10 | − |
| 11 | − |
| 12 | − |
| 13 | ++ |
| 17 | − |
| 18 | − |
| 19 | − |
| 20 | − |
| 21 | − |
| 22 | ++ |
| 23 | ++ |
| 24 | − |
| 25 | − |
| 26 | − |
| 27 | − |
| 28 | − |
| 29 | − |
| 30 | − |
| 31 | − |
| 32 | − |
| 33 | − |
| 34 | − |
| 35 | − |
| 36 | − |
| 37 | − |
| 38 | − |
| 39 | − |
| 40 | ++ |
| 41 | − |
| 42 | ++ |
| 43 | − |
| 44 | − |
| 45 | − |
| 46 | − |
| 47 | − |
| 48 | − |
| 49 | − |
| 50 | ++ |
| 51 | − |
| 52 | − |
| 54 | − |
| 56 | − |
| 57 | − |
| 58 | + |
| 59 | + |
| 60 | + |
| 61 | − |
| 65 | − |
| 66 | + |
| 67 | − |
| 68 | − |
| 69 | − |
| 72 | − |
| 73 | − |
| 74 | − |
| 75 | + |
| 76 | − |
| 77 | + |
| 78 | ++ |
| 79 | − |

TABLE B-continued

| Compound No. | Influenza H1N1 affinity, $EC_{50}$ |
|---|---|
| 80 | ++ |
| 82 | + |
| 86 | − |
| 87 | ++ |
| 88 | + |
| 90 | +++ |
| 93 | ++ |
| 94 | +++ |
| 95 | ++ |
| 96 | +++ |
| 97 | ++ |
| 99 | ++ |
| 100 | − |
| 102 | − |
| 103 | − |
| 104 | − |
| 105 | − |
| 106 | − |
| 107 | − |
| 108 | ++ |
| 109 | + |
| 110 | − |
| 112 | + |
| 113 | − |
| 114 | + |
| 115 | − |
| 116 | + |
| 117 | + |
| 118 | − |
| 120 | ++ |
| 121 | − |
| 122 | − |
| 123 | + |
| 126 | + |
| 127 | ++ |
| 128 | ++ |
| 129 | ++ |
| 130 | ++ |

All references provided herein are incorporated herein in its entirety by reference. As used herein, all abbreviations, symbols and conventions are consistent with those used in the contemporary scientific literature. See, e.g., Janet S. Dodd, ed., The ACS Style Guide: A Manual for Authors and Editors, 2nd Ed., Washington, D.C.: American Chemical Society, 1997.

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A compound of Formula I:

(I)

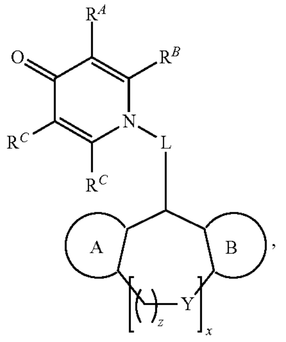

wherein:

Y is O, S, $SO_2$, or $NR^1$;

A and B are each independently null, $C_{6-10}$aryl, or 5-7 membered heteroaryl having 1-3 ring heteroatoms selected from N, O, and S, and the aryl or heteroaryl is optionally substituted with 1-4 $R^2$, L is a bond, $NR^3$, or $C(R^4)_2$;

$R^A$ is H, OH, —O—$C_{6-10}$aryl, or —O—$C_{1-6}$alkylene-O—$CO_2R^4$;

$R^B$ is H, —OH, $CO_2R^4$, C(O)$NH_2$, C(O)NHOH, C(O) $NHOR^5$, C(O)$NHR^5$, or $CON(R^5)_2$;

each $R^C$ is independently H, OH, or $CO_2R^4$;

$R^1$ is H, $C_{1-6}$alkyl, $C_{1-6}$alkylene-$C_{6-10}$aryl, or —$CO_2R^4$, and $C_{6-10}$aryl is optionally substituted with $OR^4$;

each $R^2$ is independently H, halo, —OH, $C_{1-6}$ alkyl, $C_{1-6}$alkoxy, —$NH_2$, —NH($C_{1-6}$alkyl), —N($C_{1-6}$alkyl)$_2$, —CN, —$CO_2R^4$, $C_{6-10}$aryl, or 5-10 membered heterocyclyl having 1-3 ring heteroatoms selected from N, O, and S, and each of $C_{1-6}$alkyl, $C_{1-6}$alkoxy, $C_{6-10}$aryl, and 5-10 membered heterocyclyl is optionally substituted with 1-3 halo;

$R^3$ is H, $C_{1-6}$alkyl, —C(O) $C_{1-6}$alkyl, or $C_{1-6}$alkylene-$C_{6-10}$aryl, each $R^4$ is independently H, $C_{1-6}$alkyl, or $C_{0-6}$alkylene-Ar;

each $R^5$ is independently H, —OH, —$C_{1-6}$ alkyl, $C_{1-6}$alkoxy, —$C_{1-6}$alkoxy-$C_{6-10}$aryl, or —$C_{0-6}$alkylene-$C_{6-10}$aryl, and —$C_{1-6}$ alkyl and $C_{6-10}$aryl are optionally substituted with $R^6$ or $OR^6$;

each $R^6$ is independently H, —$C_{1-6}$alkyl, —Co-6alkylene-$C_{6-10}$aryl, —$C_{1-6}$alkylene-O—$C_{1-6}$alkyl, or

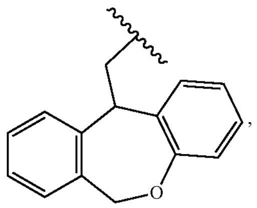 [SMILES: *CC1c2ccccc2COc2ccccc21]

and $C_{1-6}$alkyl and $C_{6-10}$aryl are optionally substituted with one or more $R^7$;

$R^7$ is H, —OH, —$CF_3$, or $C_{6-10}$aryl;

Ar is 5-10 membered heteroaryl comprising 1-3 ring heteroatoms selected from O, N, and S optionally substituted with (i) 1-3 $C_{3-8}$ cycloalkyl or (ii) 5-10 membered heteroaryl comprising 1-3 ring heteroatoms selected from O, N, and S, and each of $C_{3-8}$ cycloalkyl (i) and 5-10 membered heteroaryl (ii) is optionally substituted with 1-3 $R^2$;

x is 0 or 1; and z is 0 or 1, or a pharmaceutically acceptable salt thereof, with the proviso that when z is 0, then Y is $NR^1$, A is null, and L is $NR^3$, and with the proviso that when x is 0, L is $NR^3$.

2. The compound or salt of claim 1, wherein x is 0.

3. The compound or salt of claim 1, wherein x is 1.

4. The compound or salt of claim 1, wherein z is 1.

5. The compound or salt of claim 1, wherein at least one of A and B is Caryl.

6. The compound or salt of claim 1, wherein Y is O.

7. The compound or salt of claim 1, wherein Y is S.

8. The compound or salt of claim 1, wherein Y is $NR^1$.

9. The compound or salt of claim 1, wherein L is $NR^3$.

10. The compound of claim 1, having the structure of any one of Formulas Ia-Ih:

(Ia)

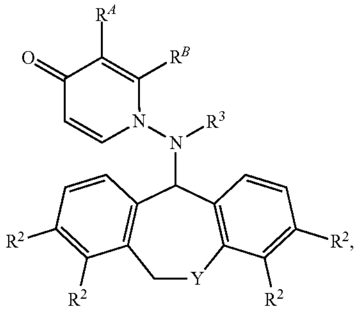

(Ib)

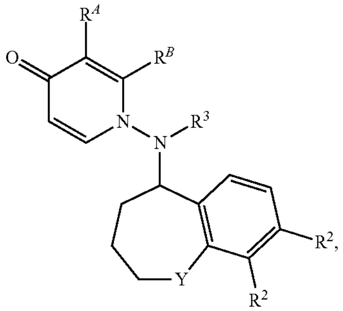

(Ic)

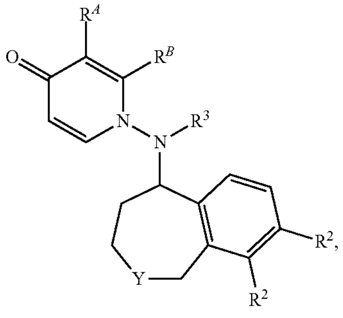

-continued (Id)

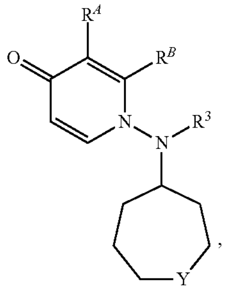

(Ir)

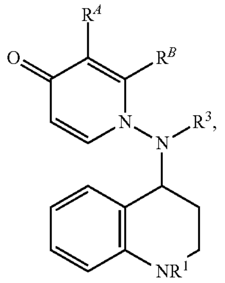

(If)

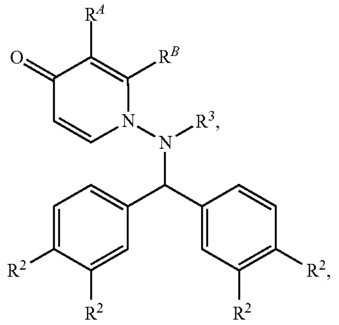

(Ig)

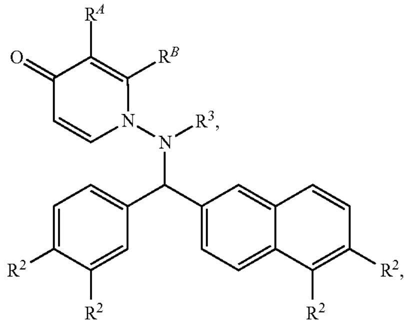

(Ih)

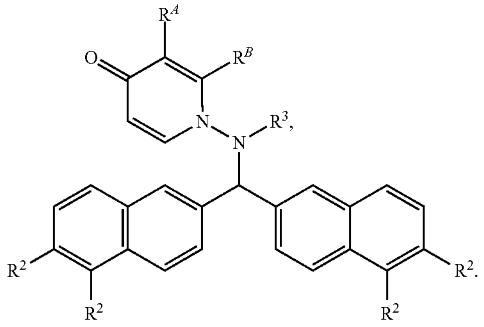

11. The compound or salt of claim 1, wherein each $R^2$ is H.

12. The compound or salt of claim 1, wherein one or two $R^2$ are halo.

13. The compound or salt of claim 1, wherein $R^5$ is H.

14. The compound or salt of claim 1, wherein $R^5$ is —$C_{1-6}$ alkyl.

15. The compound or salt of claim 1, wherein $R^5$ is —OH.

16. The compound or salt of claim 1, wherein $R^5$ is $CO_2R^4$.

17. The compound or salt of claim 16, wherein $R^4$ is H.

18. The compound or salt of claim 16, wherein $R^4$ is methyl.

19. The compound or salt of claim 1, wherein $R^6$ is —$C_{1-6}$alkyl.

20. The compound or salt of claim 1, wherein $R^6$ is —$C_{0-6}$alkylene-phenyl.

21. A compound selected from the group consisting of:

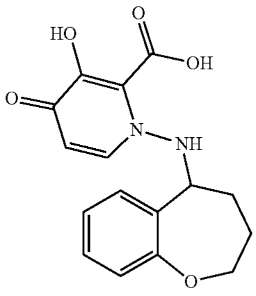,

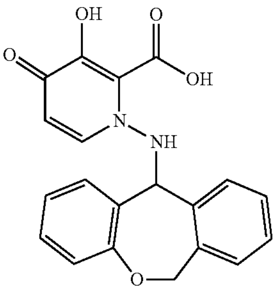,

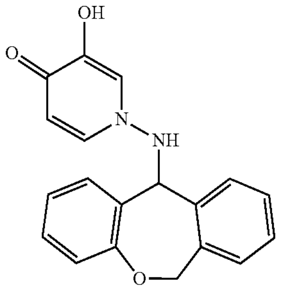,

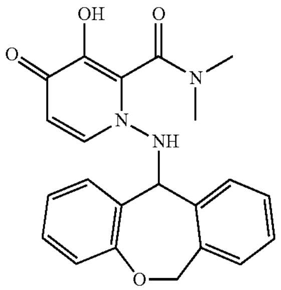,

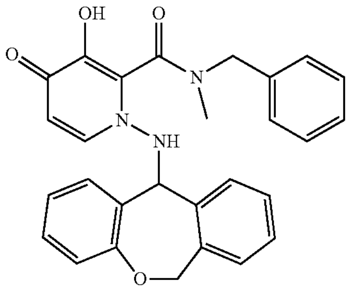,

-continued

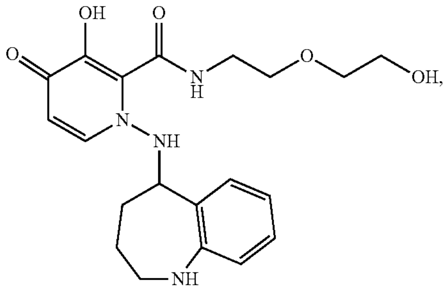,

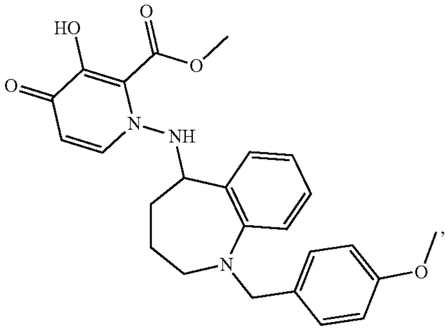,

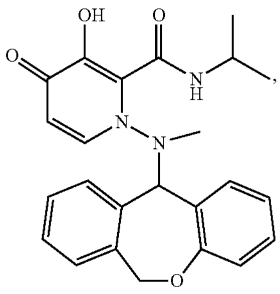,

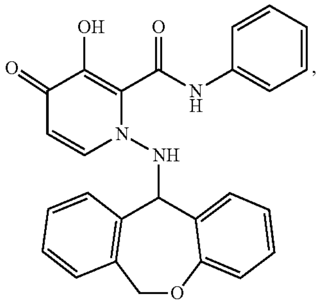,

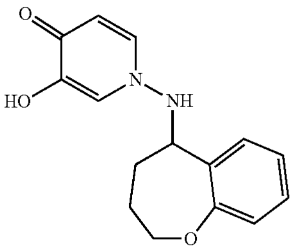,

-continued
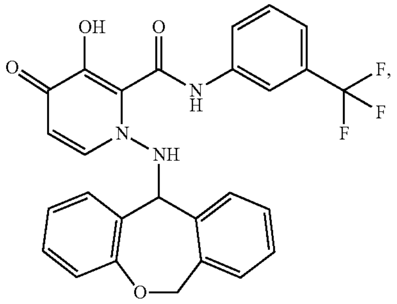
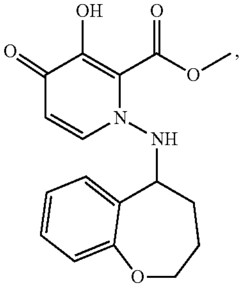
,
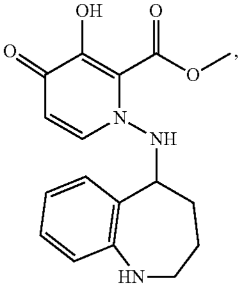
,
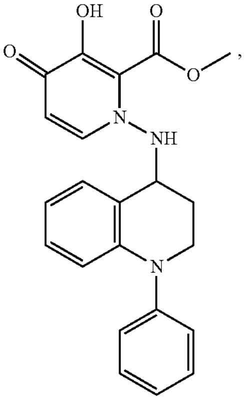
,
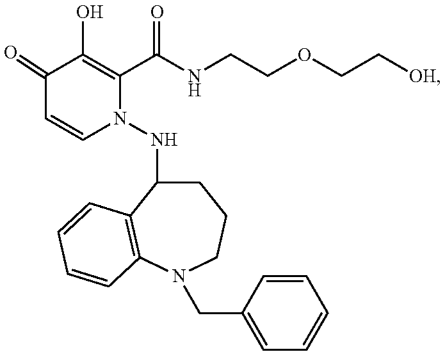
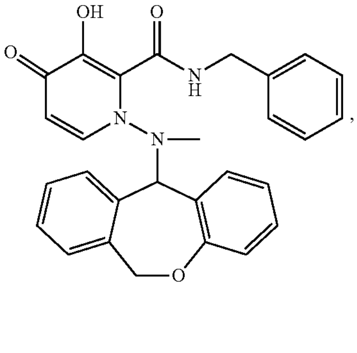
,
-continued
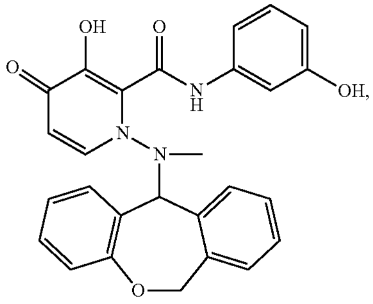
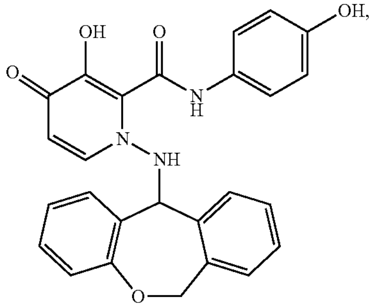
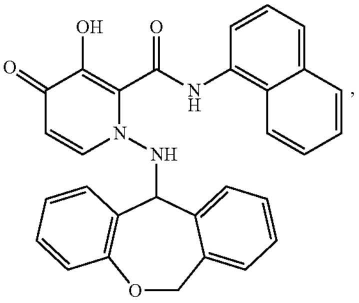
,
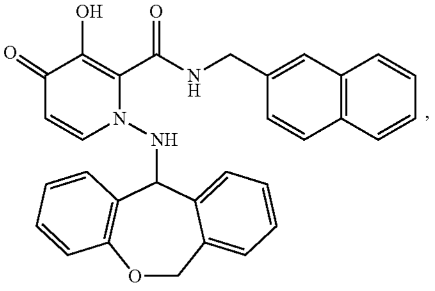
,
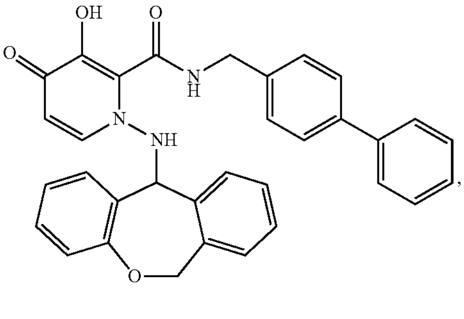
, -continued
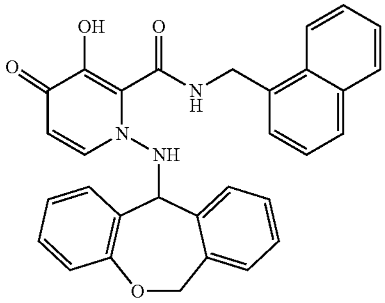
,
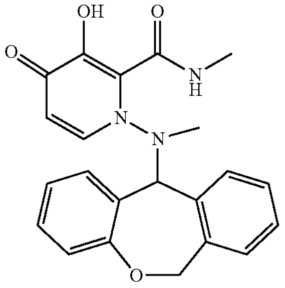
,
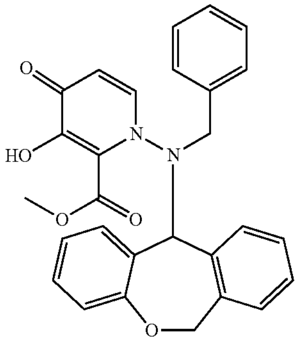
,
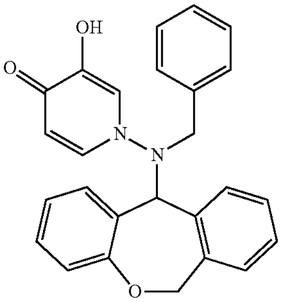
,
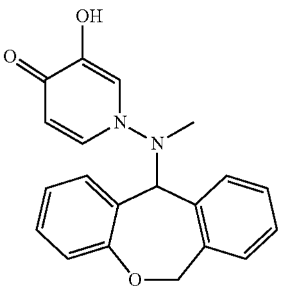
,
-continued
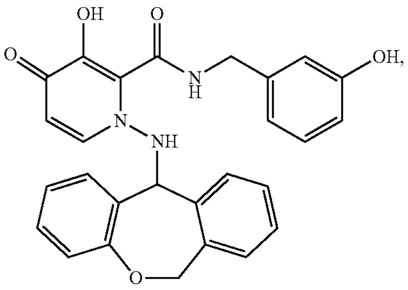
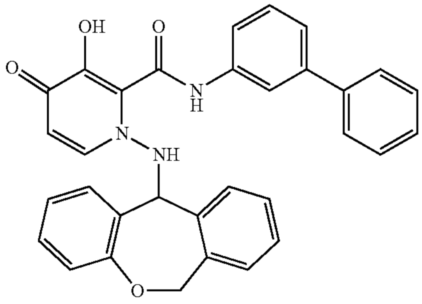
,
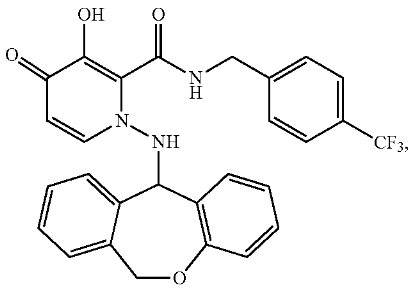
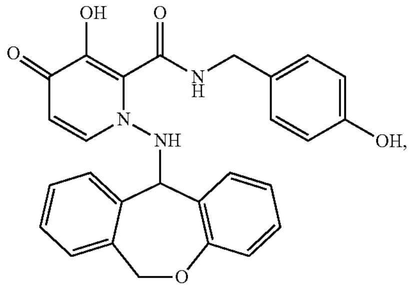
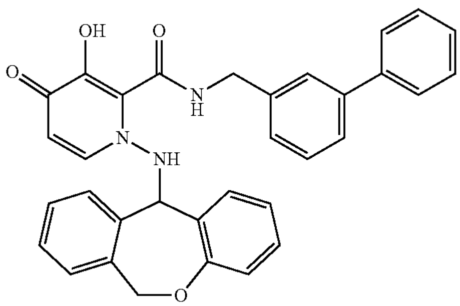
, -continued
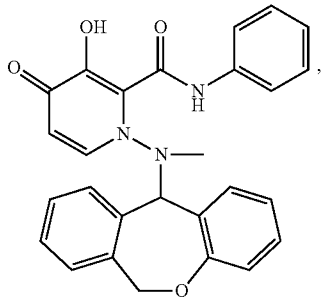
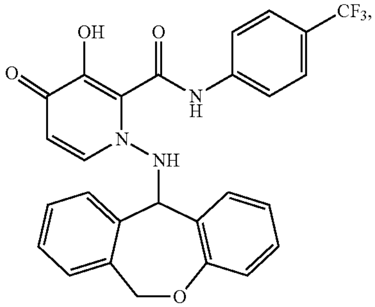
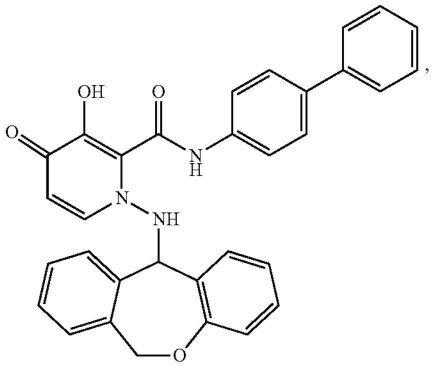
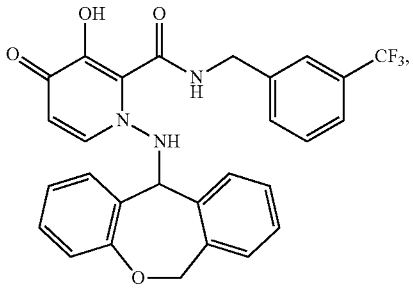
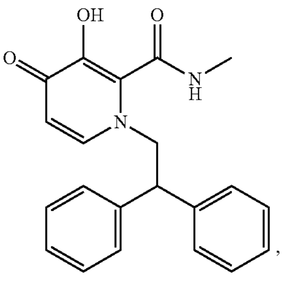
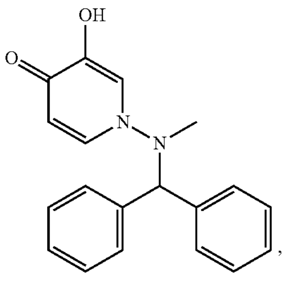
-continued
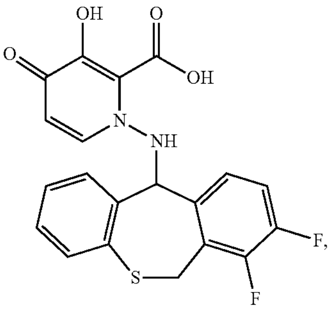
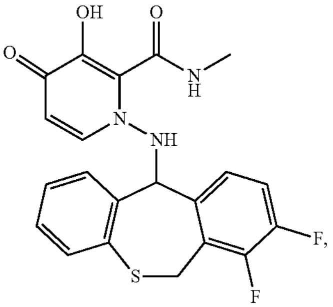
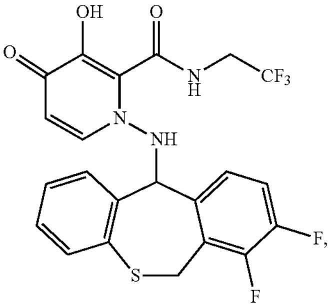
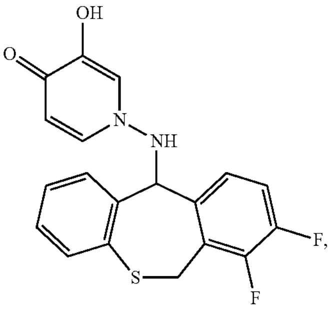
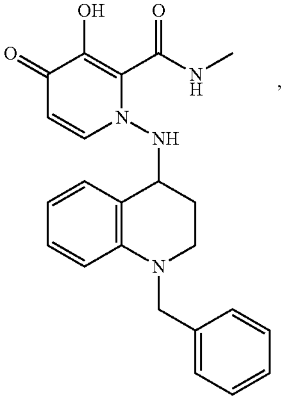
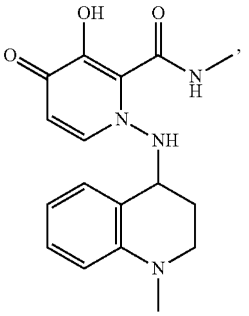

-continued
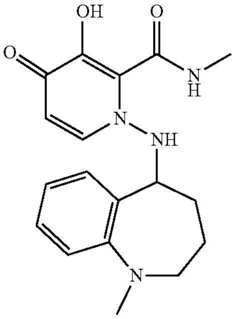,
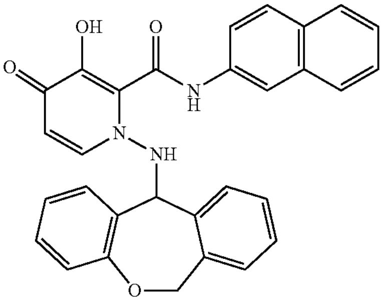,
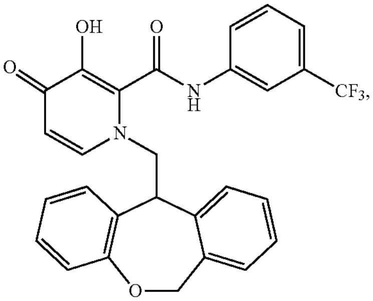
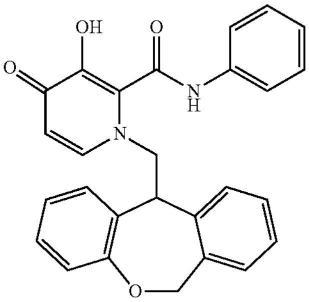,
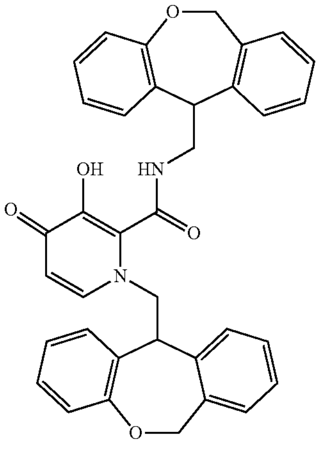
-continued
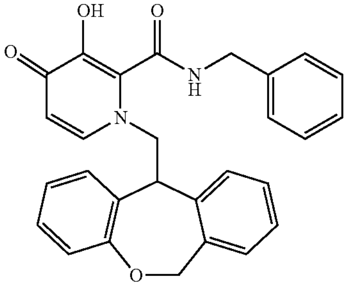,
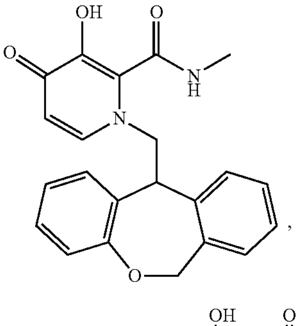,
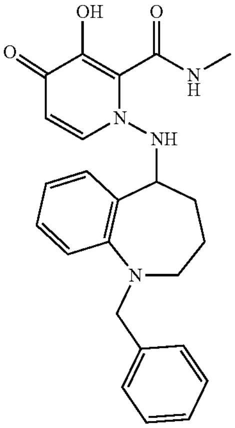,
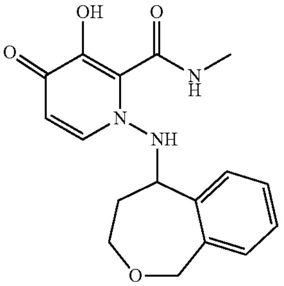,
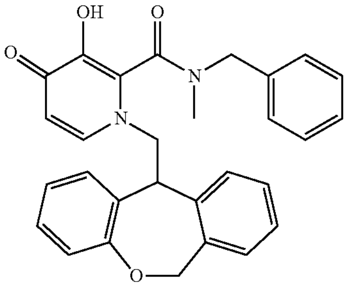,
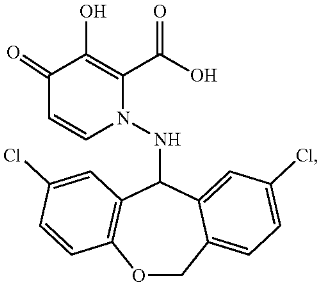

-continued
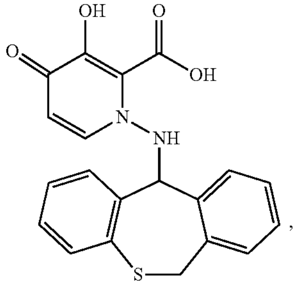,
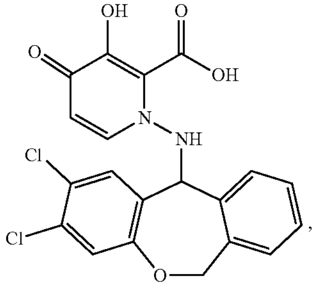,
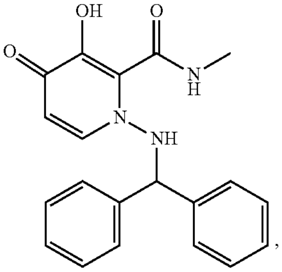,
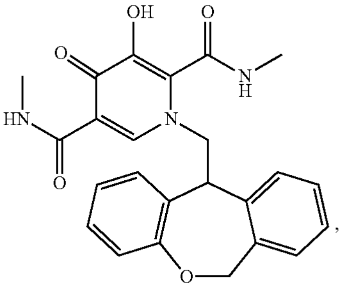,
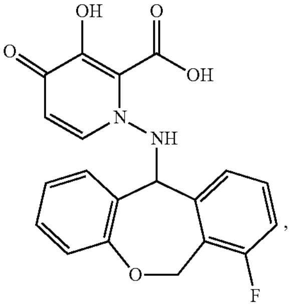,
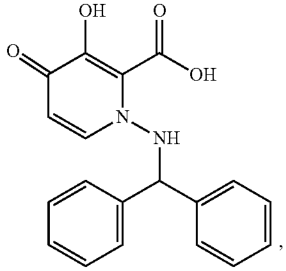,
-continued
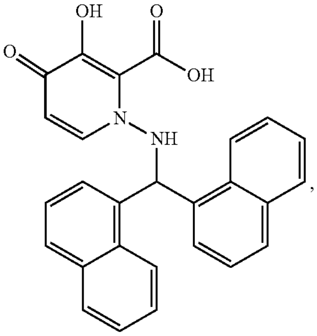,
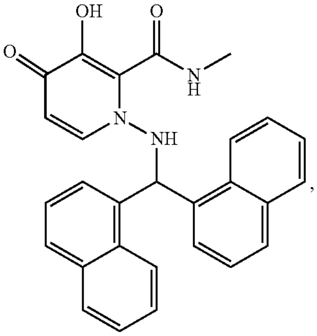,
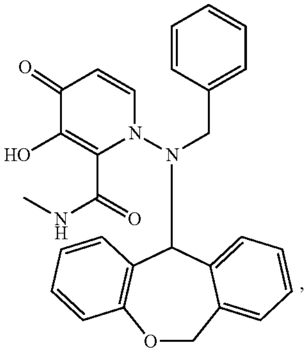,
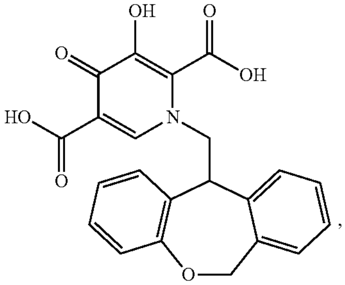,
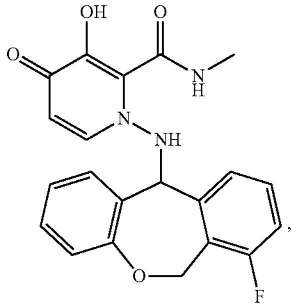, -continued
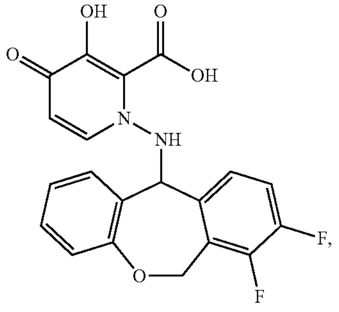
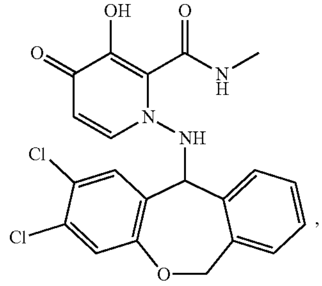
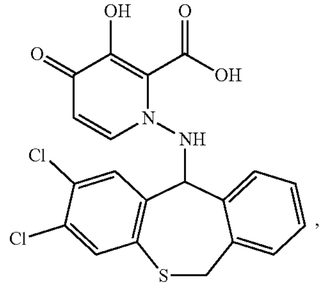
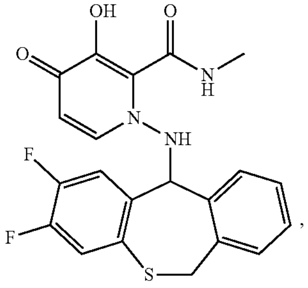
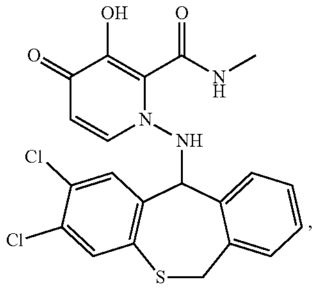
-continued
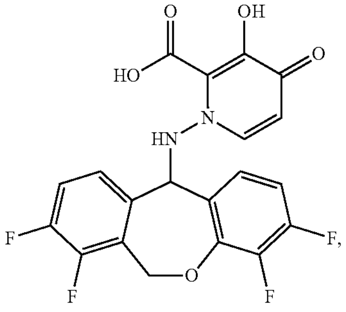
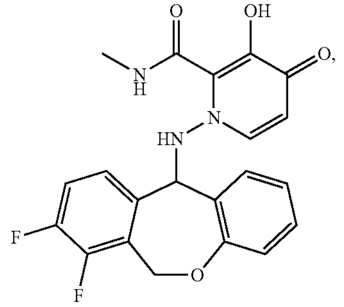
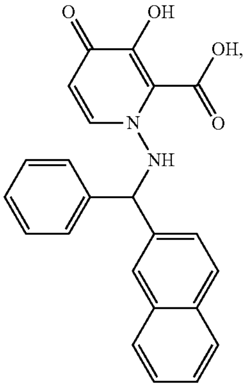
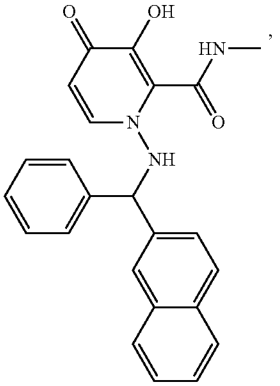
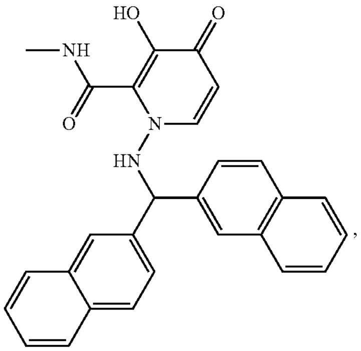
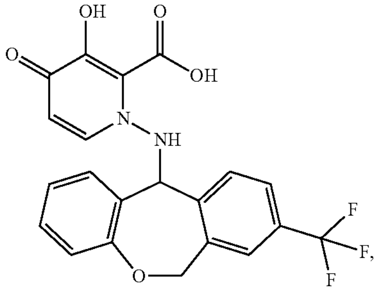

-continued
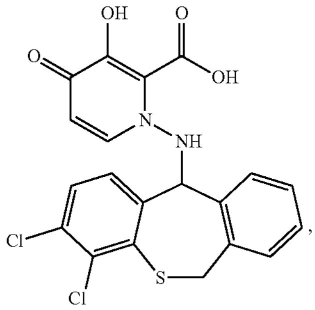
,
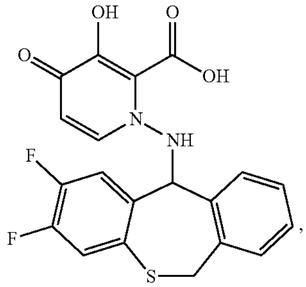
,
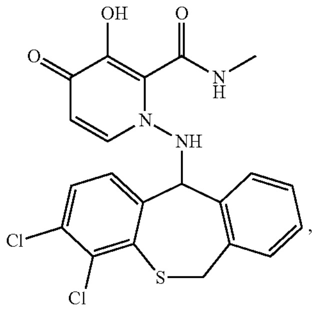
,
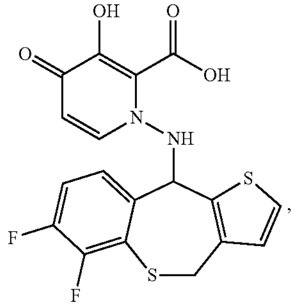
,
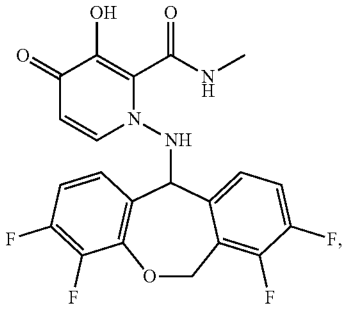
,
-continued
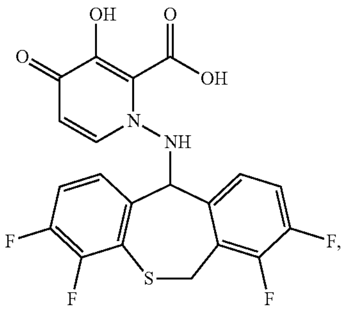
,
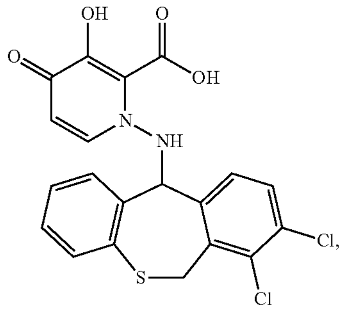
,
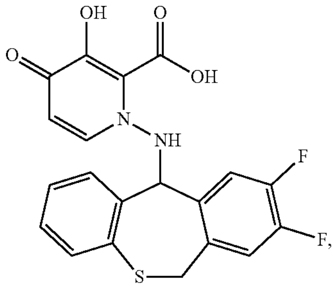
,
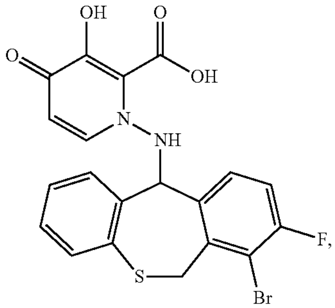
,
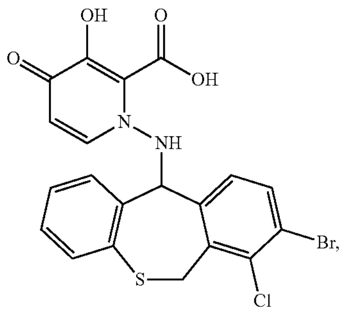
, -continued
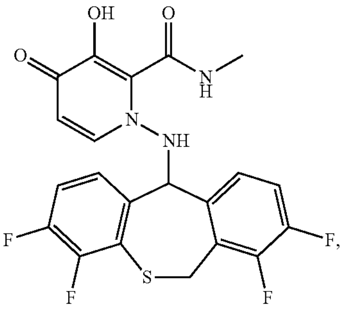
,
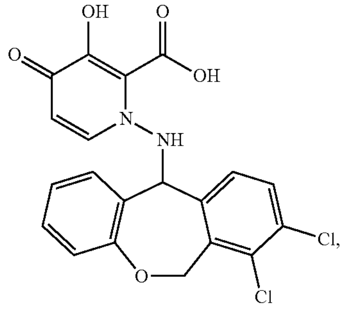
,
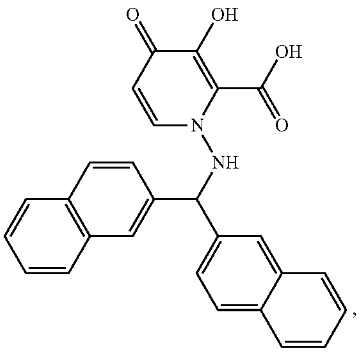
,
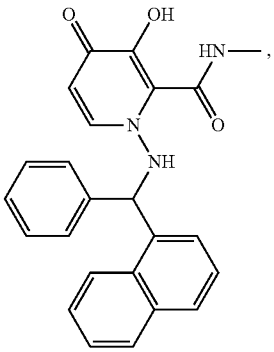
,
-continued
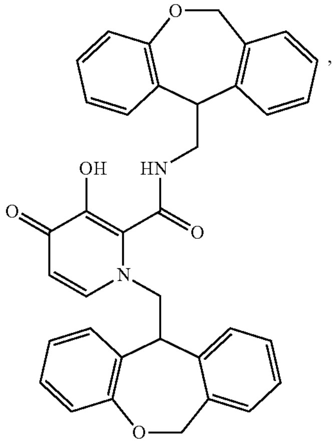
,
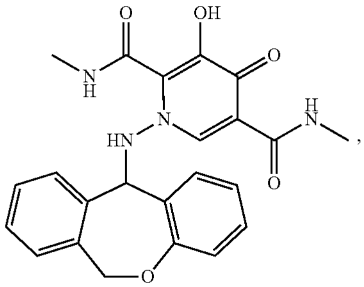
,
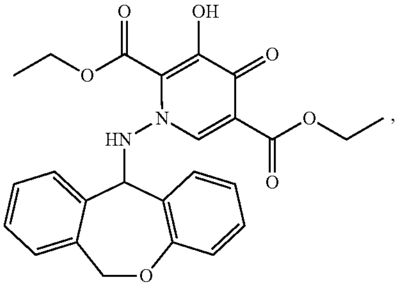
,
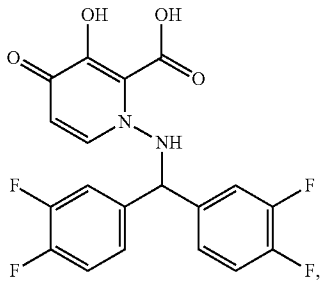
, -continued
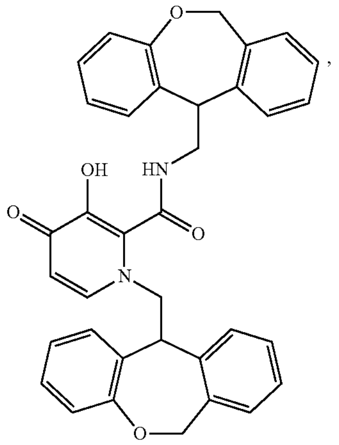
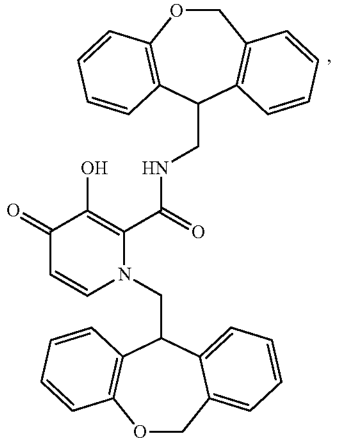
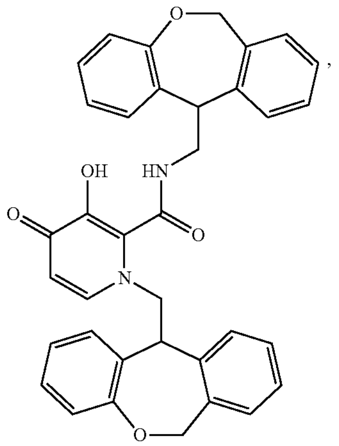
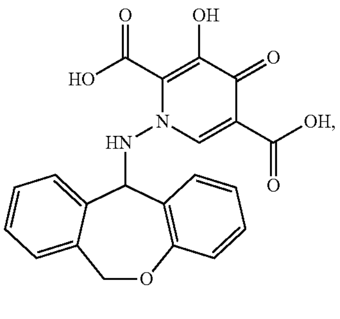
-continued
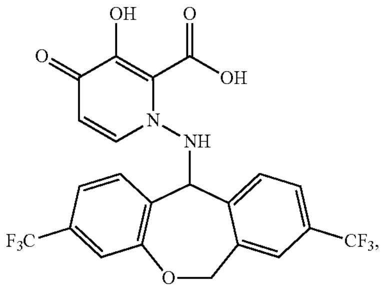
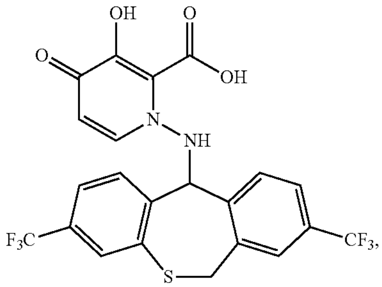
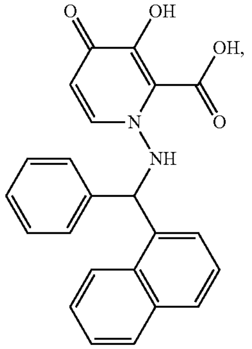
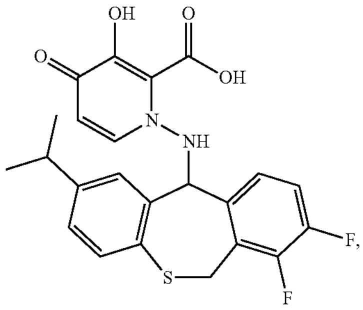
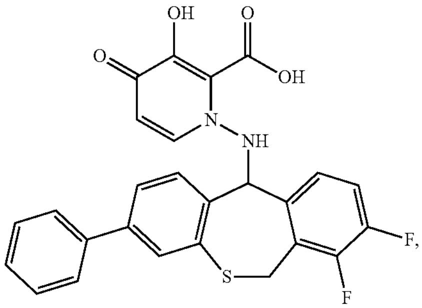

-continued
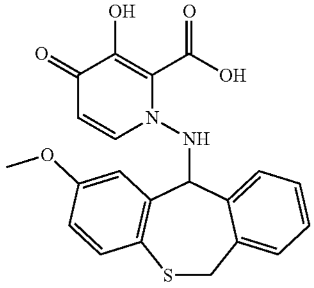
,
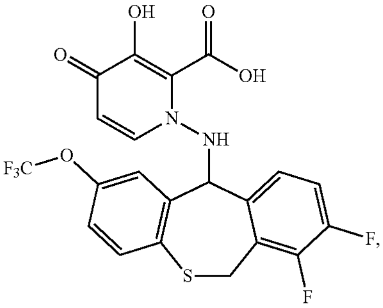
,
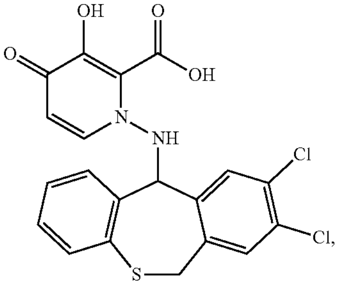
,
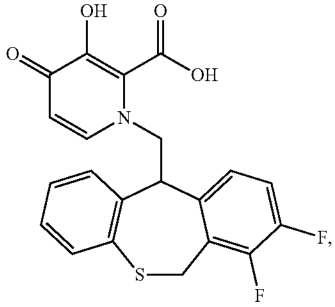 [SMILES: O=C(O)c1c(O)c(=O)ccn1CC1c2ccccc2SCc2c1ccc(F)c2F]
,
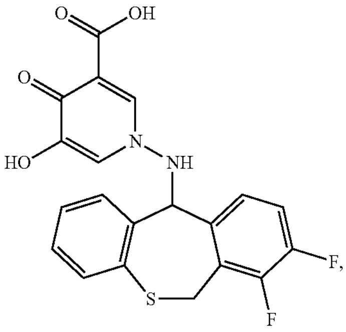
,
-continued
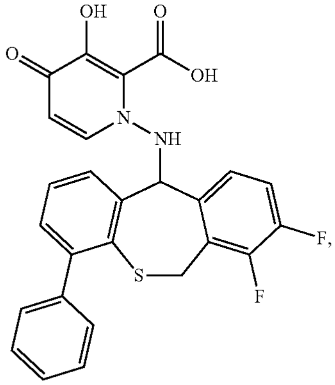
,
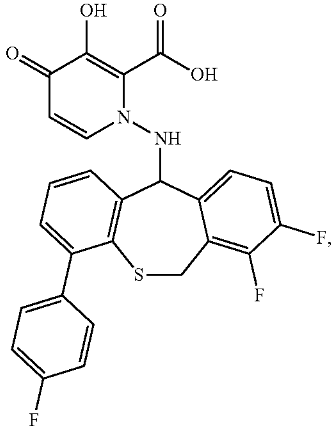
,
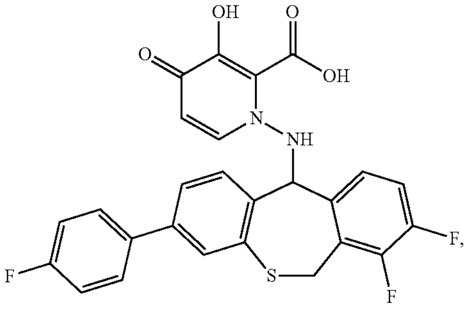
,
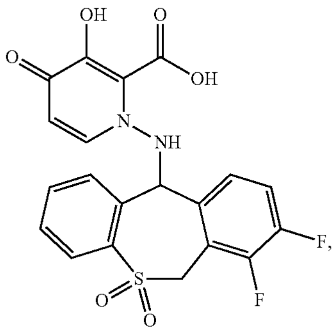
, -continued

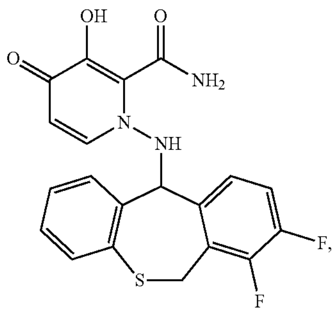

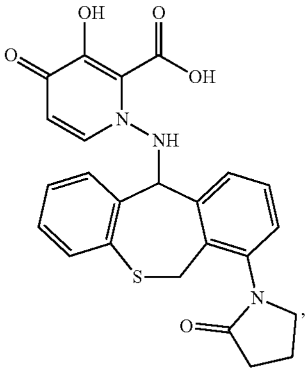

-continued

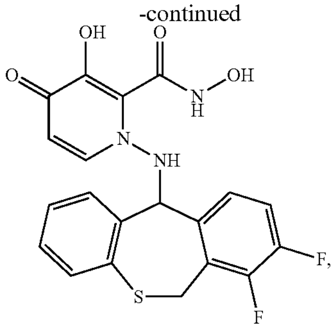

and

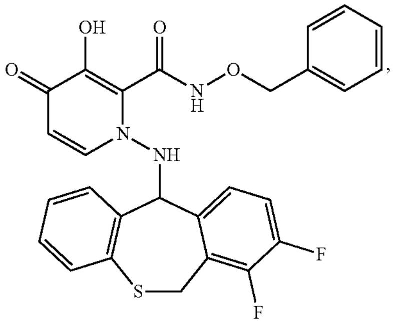

or a pharmaceutically acceptable salt thereof.

22. A pharmaceutical composition comprising the compound or salt of claim 1 and a pharmaceutically acceptable carrier, adjuvant, or vehicle.

23. A method of treating or preventing influenza in a patient, comprising administering to said patient a safe and effective amount of the compound or salt of claim 1.

24. A method of reducing the amount of influenza virus in a biological sample or in a patient, comprising administering to said biological sample or patient a safe and effective amount of the compound or salt of claim 1.

* * * * *